US007531718B2

(12) United States Patent
Fillatti

(10) Patent No.: US 7,531,718 B2
(45) Date of Patent: May 12, 2009

(54) NUCLEIC ACID SEQUENCES AND METHODS OF USE FOR THE PRODUCTION OF PLANTS WITH MODIFIED POLYUNSATURATED FATTY ACIDS

(75) Inventor: Joanne J. Fillatti, Davis, CA (US)

(73) Assignee: Monsanto Technology, L.L.C., St. Louis, MO (US)

( * ) Notice: Subject to any disclaimer, the term of this patent is extended or adjusted under 35 U.S.C. 154(b) by 401 days.

(21) Appl. No.: 10/518,753

(22) PCT Filed: Jun. 20, 2003

(86) PCT No.: PCT/US03/19445

§ 371 (c)(1),
(2), (4) Date: Jun. 30, 2005

(87) PCT Pub. No.: WO04/001001

PCT Pub. Date: Dec. 31, 2003

(65) Prior Publication Data

US 2005/0262589 A1    Nov. 24, 2005

Related U.S. Application Data

(63) Continuation-in-part of application No. 10/176,149, filed on Jun. 21, 2002, now Pat. No. 7,067,722, which is a continuation-in-part of application No. 09/638,508, filed on Aug. 11, 2000, now abandoned.

(60) Provisional application No. 60/172,128, filed on Dec. 17, 1999, provisional application No. 60/151,224, filed on Aug. 26, 1999.

(51) Int. Cl.
*A01H 5/00* (2006.01)
*C12N 15/82* (2006.01)

(52) U.S. Cl. ...................... 800/312; 800/281
(58) Field of Classification Search ........................ None
See application file for complete search history.

(56) References Cited

U.S. PATENT DOCUMENTS

| 4,557,734 | A | 12/1985 | Schwab et al. |
| 5,454,842 | A | 10/1995 | Poirier et al. |
| 5,475,099 | A | 12/1995 | Knauf et al. |
| 5,627,061 | A | 5/1997 | Barry et al. |
| 5,633,435 | A | 5/1997 | Barry et al. |
| 5,714,670 | A | 2/1998 | Fehr et al. |
| 5,723,595 | A | 3/1998 | Thompson et al. |
| 5,723,761 | A | 3/1998 | Voelker et al. |
| 5,850,026 | A | 12/1998 | Debonte et al. |
| 5,888,947 | A | 3/1999 | Lambert et al. |
| 5,891,203 | A | 4/1999 | Ball et al. |
| 5,955,329 | A | 9/1999 | Yuan et al. |
| 5,955,650 | A | 9/1999 | Hitz |
| 6,013,114 | A | 1/2000 | Hille et al. |
| 6,331,664 | B1 | 12/2001 | Rubin-Wilson et al. |
| 6,369,296 | B1 | 4/2002 | Ratcliff et al. |
| 2002/0034814 | A1 | 3/2002 | Atabekov et al. |
| 2003/0049835 | A1 | 3/2003 | Helliwell et al. |
| 2003/0135882 | A1 | 7/2003 | Metzlaff et al. |
| 2004/0107460 | A1 | 6/2004 | Fillatti et al. |
| 2004/0126845 | A1 | 7/2004 | Eenennaam et al. |
| 2005/0034190 | A9 | 2/2005 | Fillatti et al. |

FOREIGN PATENT DOCUMENTS

| EP | 0 959 133 A1 | 11/1999 |
| WO | WO 93/11245 A1 | 6/1993 |
| WO | WO 94/10189 A1 | 5/1994 |
| WO | WO 94/11516 A1 | 5/1994 |
| WO | WO 98/05770 A2 | 2/1998 |
| WO | WO 98/30083 A1 | 7/1998 |
| WO | WO 98/46776 A2 | 10/1998 |
| WO | WO 98/53083 A1 | 11/1998 |
| WO | WO 99/15682 A2 | 4/1999 |
| WO | WO 99/32619 A1 | 7/1999 |
| WO | WO 99/49029 A1 | 9/1999 |
| WO | WO 99/53050 A1 | 10/1999 |
| WO | WO 99/61631 A1 | 12/1999 |
| WO | WO 99/64579 A2 | 12/1999 |
| WO | WO 00/07432 A1 | 2/2000 |
| WO | WO 00/44895 A1 | 8/2000 |
| WO | WO 00/44914 A1 | 8/2000 |
| WO | WO 00/68374 A1 | 11/2000 |
| WO | WO 01/14538 A2 | 3/2001 |
| WO | WO 01/34822 A2 | 5/2001 |
| WO | WO 01/35726 A1 | 5/2001 |

(Continued)

OTHER PUBLICATIONS

Okuley et al. Arabidopsis FAD2 gene encodes the enzyme that is essential for polyunsaturated lipid synthesis. (1994) The Plant Cell, vol. 6, pp. 147-158.*

Levin et al., "Methods of double-standed RNA-mediated gene inactivation in *Arabidopsis* and their use to define an essential gene in methionine biosynthesis," *Plant Molecular Biology*, 44(6):759-775 (2000).

Peele et al., "Silencing of a meristematic gene using geminivirus-derived vectors," *The Plant Journal*, 2(4):357-366 (2001).

Supplementary European Search Report, European Application No. 04 78 5109 (Nov. 7, 2006).

International Search Report of Application No. PCT/US2007/003823 dated Jul. 12, 2007.

(Continued)

*Primary Examiner*—Elizabeth F McElwain
(74) *Attorney, Agent, or Firm*—Chunping Li; Arnold & Porter, LLP

(57) ABSTRACT

The present invention is directed to nucleic acid molecules and nucleic acid constructs, and other agents associated with fatty acid synthesis, particularly the ratios of saturated and unsaturated fats. Moreover, the present invention is directed to plants incorporating such agents where the plants exhibit altered ratios of saturated and unsaturated fats. In particular, the present invention is directed to plants incorporating such agents where the plants exhibit altered ratios of monounsaturated to polyunsaturated fatty acids.

17 Claims, 13 Drawing Sheets

FOREIGN PATENT DOCUMENTS

| | | |
|---|---|---|
| WO | WO 01/36598 A1 | 5/2001 |
| WO | WO 01/70949 A1 | 9/2001 |
| WO | WO 01/79499 A1 | 10/2001 |
| WO | WO 02/04581 A1 | 1/2002 |
| WO | WO 02/15675 A1 | 2/2002 |
| WO | WO 02/059336 A2 | 8/2002 |
| WO | WO 02/081711 A1 | 10/2002 |
| WO | WO 02/088301 A2 | 11/2002 |
| WO | WO 03/080802 A2 | 10/2003 |
| WO | WO 04/000871 | 12/2003 |
| WO | WO 04/001000 | 12/2003 |
| WO | WO 04/001001 | 12/2003 |

OTHER PUBLICATIONS

Stoutjesdiji et al., "hpRNA-Mediated Targeting of the Arabidopsis FAD2 Gene Gives Highly Efficient and Stable Silencing", *Plant Physiology* 129:1723-1731 (2002).

Thomas et al., "Size constraints for targeting post-transcriptional gene silencing and for RNA-directed methylation in *Nicotiana benthamiana* using a potato virus X vector", *The Plant Journal* 25(4):417-425 (2001).

Bouchon, P. et al., "Oil Distribution in Fried Potatoes Monitored by Infrared Microspectroscopy", *Journal of Food Science*, 66(7):918-923 (2001).

Buhr, T. et al., "Ribozyme Termination of RNA Transcripts Down-Regulate Seed Fatty Acid Genes in Transgenic Soybean", *The Plant Journal*, 30(2):155-163 (2002).

Cartea, M.E. et al., "Comparison of Sense and Antisense Methodologies for Modifying the Fatty Acid Composition of *Arabidopsis thaliana* Oilseed", *Plant Science*, 136, 181-194 (1998).

Clark-Walker, G.D., et al., "Location of Transcriptional Control Signals and Transfer RNA Sequences in *Torulopsis glabrata* Mitochondrial DNA", *EMBO (European Molecular Biology Organization) Journal*, 4(2):465-473 (1985).

Cogoni, C. et al., "Post-Transcriptional Gene Silencing Across Kingdoms", *Curr. Opin. Gen & Devel.*, 10(6):638-643 (2000).

Crossway, A. et al., "Integration of Foreign DNA Following Microinjection of Tobacco Mesophyll Protoplasts", *Mol. Gen. Genet.*, 202(2):179-185 (1986).

Dörmann, P. et al., "Accumulation of Palmitate in Arabidopsis Mediated by the Acyl-Acyl Carrier Protein Thioesterase FATB1", *Plant Physiology*, 123:637-643 (2000).

Database EM_GSS 'Online! EMBL Heidelberg, Germany; AC AL071390, May 29, 1999, Genoscope: "*Drosophila melanogaster* genome surface sequence TET3 end of BAC: BACR32MO5", XP002163063, abstract.

Database EMPLN 'Online! EMBL Heidelberg, Germany; AC/ID AC004705, May 21, 1998, LIN X et al.: "Sequence and analysis of chromosome 2 of the plant *Arabidopsis thaliana*" XP002163064, abstract.

Database EM_GSS 'Online! EMBL Heidelberg, Germany; AC AL105179, Jul. 26, 1999, Genoscope: "*Drosophila melanogaster* genome survey sequence T7 end of BAC: BACN13A12" XP002163065, abstract.

Database EM-New 'Online! EMBL Heidelberg, Germany; AC/ID AB022220, Jan. 15, 1999, Sato S. et al.: "*Arabidopsis thaliana* genomic DNA, chromosome 3, P1 clone: MLN21" XP002163066, abstract.

Database EM_GSS 'Online! EMBL Heidelberg, Germany; AC AL069706, May 29, 1999, Genoscope: "*Drosophila melanogaster* genome survey sequence T7 end of BAC: BACR29B23" XP002163067, abstract.

Database EM_GSS 'Online! EMBL Heidelberg, Germany; AC AL063932, May 29, 1999, Genoscope: "*Drosophila melanogaster* genome survey sequence TET3 end of BAC: BACR8010" XP002163068, abstract.

Database EM_GSS 'Online! EMBL Heidelberg, Germany; AC AL108811, Jul. 26, 1999, Genoscope: "*Drosophila melanogaster* genome survey sequence SP6 end of BAC BACN37D10" XP002163069, abstract.

Database EM_New 'Online! EMBL Heidelberg, Germany; AC/ID AB026636, May 7, 1999, Sato S. et al.: "*Arabidopsis thaliana* genomic DNA, chromosome 3, TAC clone: K14A17", XP002163070, abstract.

Database EMEST_PLN 'Online! EMBL Heidelberg, Germany; AC/ID AW297948, Feb. 8, 2000, Shoemaker R. et al.: "Public soybean EST project", XP002163071, abstract.

Database EMPLN 'Online! EMBL Heidelberg, Germany; AC AL161581, Mar. 16, 2000, Weichselgartner M. et al.: "*Arabidopsis thaliana* chromosome 4, contig fragment No. 77", XP002163072, abstract.

Duffield, J. et al., "U.S. Biodiesel Development: New Markets for Conventional and Genetically Modified Agricultural Products", *Economic Research Service USDA*, pp. 1-31 (1998).

Dunn, R.O. et al., "Recent Advances in the Development of Alternative Diesel Fuel from Vegetable Oils and Animal Fats", *Recent Res. Devel. in Oil Chem.*, 1:31-56 (1997).

Erhan, S. et al., "Lubricant Basestocks from Vegetable Oils", *Industrial Crops and Products*, 11:277-282 (2000).

Fire, A. et al., "Potent and Specific Genetic Interference by Double-Stranded RNA in *Caenorhabditis elegans*", *Nature*, 391:806-811 (1998).

Halpin, C. et al., "Enabling Technologies for Manipulating Multiple Genes on Complex Pathways", *Plant Molecular Biology*, 47:295-310 (2001).

Hamada, T. et al., "Modification of Fatty Acid Composition by Over- and Antisense-Expression of a Microsomal ω-3 Fatty Acid Desaturase Gene in Transgenic Tobacco", *Transgenic Research*, 5(2), 115-121 (1996).

International Search Report mailed Nov. 13, 2003, in PCT/US03/08610.

International Search Report mailed Jul. 12, 2005, in PCT/US04/31605.

International Search Report mailed Apr. 9, 2004, in PCT/US03/19445.

International Search Report mailed Apr. 26, 2001, in PCT/US00/22613.

Lee, Y., et al., "Antisense Expression of the CK2 α-Subunit Gene in Arabidopsis. Effects on Light-Regulated Gene Expression and Plant Growth", *Plant Physiology*, 119:989-1000 (1999).

Lewin, B., "How Did Interrupted Genes Evolve?", *Genes*, 2nd Edition, pp. 333-337.

Matzke, M.A. et al., "RNA-Based Silencing Strategies in Plants", *Curr. Opin. Gen & Devel.*, 11(2):221-227 (2001).

Mensink, R. et al., "Effect of Dietary Fatty Acids on Serum Lipids and Lipoproteins: A Meta-Analysis of 27 Trials", *Arteriosclerosis and Thrombosis*, 12(8):911-919 (1992).

Montgomery, M.K. et al., "RNA as a Target of Double-Stranded RNA-Mediated Genetic Interference in *Caenorhabditis elegans*", *Proc. Nat.l Acad. Sci. USA*, 95(96):15502-15507 (1998).

Napoli, C. et al., "Introduction of a Chimeric Chalcone Synthase Gene into Petunia Results in Reversible Co-Suppression of Homologous Genes *in trans*", *The Plant Cell*, 2:279-289 (1990).

Neff, W.E. et al., "Odor Significance of Undersirable Degradation Compounds in Heated Triolein and Trilinolein", *JAOCS*, 77(12):1303-1313 (2000).

Okuley, J., et al., "Arabidopsis FAD2 Gene Encodes the Enzyme that is Essential for Polyunsaturated Lipid Synthesis", *The Plant Cell*, 6:147-158 (1994).

Qing, L., Thesis, "The Isolation and Characterisation of Fatty Acid Desaturase Genes in Cotton", University of Sydney, Australia, pp. ii-iv, 24-26, 121-123, 142, 167-168, 172-174, and 179-181 (1998).

Sharpe, P.A., "RNAi and Double-Strand RNA", *Genes & Development*, 13:139-141 (1999).

Sharp, P.A., "RNA Interference—2001", *Genes & Development*, 15:485-490 (2001).

Supplemental European Search Report in European Application No. 03711656.3 completed Jun. 29, 2005.

Timmons, J.S. et al., "Relationships Among Dietary Roasted Soybeans, Milk Components, and Spontaneous Oxidized Flavor of Milk", *Journal of Dairy Science*, 84(11):2440-2449 (2001).

Toborek, M. et al., "Unsaturated Fatty Acids Selectively Induce an Inflammatory Environment in Human Endothelial Cells", *American Journal of Clinical Nutrition*, 75:119-125 (2002).

van der Krol, A. R. et al., "Flavonoid Genes in Petunia: Addition of a Limited Number of Gene Copies May Lead to a Suppression of Gene Expression", *The Plant Cell*, 2:291-299 (1990).

Warner, K. et al., "Effect of Oleic and Linoleic Acids on the Production of Deep-Fried Odor in Heated Triolein and Trilinolein", *Journal of Agricultural Food Chemical*, 49:899-905 (2001).

Waterhouse, P.M. et al., "Virus Resistance and Gene Silencing in Plants Can be Induced by Simultaneous Expression of Sense and Antisense RNA", *Proc. Natl. Acad. Sci. USA*, 95:13959-13964 (1998).

Wesley, S.V. et al., "Construct Design for Efficient, Effective and High-Throughput Gene Silencing in Plants", *The Plant Journal*, 27(6):581-590 (2001).

\* cited by examiner

SEQUENCE LISTING

<160> NUMBER OF SEQ ID NOS: 39

<210> SEQ ID NO 1
<211> LENGTH: 420
<212> TYPE: DNA
<213> ORGANISM: Glycine max

<400> SEQUENCE: 1

```
gtaaattaaa ttgtgcctgc acctcgggat atttcatgtg gggttcatca tatttgttga      60
ggaaaagaaa ctcccgaaat tgaattatgc atttatatat ccttttttcat ttctagattt     120 cctgaaggct taggtgtagg cacctagcta gtagctacaa tatcagcact tctctctatt     180
gataaacaat tggctgtaat gccgcagtag aggacgatca caacatttcg tgctggttac     240
```

```
tttttgtttt atggtcatga tttcactctc tctaatctct ccattcattt tgtagttgtc      300
attatcttta gattttcac tacctggttt aaaattgagg gattgtagtt ctgttggtac       360
atattacaca ttcagcaaaa caactgaaac tcaactgaac ttgtttatac tttgacacag      420
```

<210> SEQ ID NO 2
<211> LENGTH: 405
<212> TYPE: DNA
<213> ORGANISM: Glycine max

<400> SEQUENCE: 2

```
gtatgatgct aaattaaatt gtgcctgcac cccaggatat ttcatgtggg attcatcatt       60
tattgaggaa aactctccaa attgaatcgt gcatttatat ttttttttcca tttctagatt     120 tcttgaaggc ttatggtata ggcacctaca attatcagca cttctctcta ttgataaaca     180
attggctgta ataccacagt agagaacgat cacaacattt tgtgctggtt accttttgtt      240
ttatggtcat gatttcactc tctctaatct gtcacttccc tccattcatt tgtacttct       300 catattttc acttcctggt tgaaaattgt agttctcttg gtacatacta gtattagaca       360
ttcagcaaca acaactgaac tgaacttctt tatactttga cacag                      405
```

<210> SEQ ID NO 3
<211> LENGTH: 6220
<212> TYPE: DNA
<213> ORGANISM: Glycine max

<400> SEQUENCE: 3

```
agcttggtac cgagctcgga tccactagta acggccgcca gtgtgctgga attcggcttc       60
tctctcaccc tcctcttcac acattttctg tgcgctctaa caaacattct cgttcacact     120
ttcaggtact tttctctcct tatctctta tctttattct ttcctacttt attgcttaaa       180
ccaatgctat ctatgcttcg atctcgcctt cttattttcc acttcccttt tctcgcttga      240
tctaaccgtt ttcgccctcc gcgcttcgat tgactgagta catctacgat tctctgttct     300
ttcatttcat agatttcgtc tgattttggc taacttggtt tctgttgcgg ccgattctta     360
catatactga ttgtttagca taaatgaact tgcttgttta gcactatctg catattttcg     420
tcacgcatct ctttcggatc taaggatgaa tctcctattt cctccgtatt atttctcgta     480
tctcttgttc tgtgctaatg ctccagaaaa tggcagcatt gtcttcttct ttgctgtata     540
agtgtttgtg ttgtgaatct ggaagcgatt ttgcgtgagg taacttgcga cttcaactat     600
tatctttcag atctcgttaa tttattagct gctattaatt tgtgtgtgca gtgtcaaact     660
gaagcacacg actgcttaga agttagaatt tgactgactg ttcctctttg attttttttct    720 ttcttttctt tgctwactcg gcctatttaa tgatctttat aaatagatta gtggaccact     780
tggttagttg gtgagttatg aatattcgaa ttttctacca caagttgggt taaaaaaatc      840
tctgcaacta cacgaggatt ttttatttta tttagaggaa actattctgt catccttttc     900
ccgattacac ttttctatca gttgttttga aatatacacc ttaggaatat aatattaccc      960
ctttcggtct aatataaat atattttaat tatttatatt ttatttaatg aaattattt       1020 taaaatactt tcatttaata gaattttaa taaagttaaa gacttttatt gtgtagagtt      1080
taacgaagtt aattagtttt cttagtaaat gtaaaatatg ccttttttgt tgtttataat     1140
ggagattgga aaaatatac tttaattttt ttcaagtgat gaataattat ggatgttttg      1200
tcaatatttt tgtcttgcta tacaactttc agtcttgcca ttaaataatt ttgaatgtgt      1260
tattgatatc tctgaacaat atttagagac gaacataaat tttatatatt ttatataatt    1320
```

```
tcttttttatt acccttttat tatcaatttt gaaatttggt taatatctgt gtttcatttt    1380
gaggtctcaa atttgatata aggaggttca aaatgcgttg ctagccattt taaagattag    1440
caggagagga aatgtttctg gacttaaatt taaaatatgc ttatttgttt ttcaagagag    1500
agagatcaat atttatataa tacacttgaa ttaatataca ccattgttgc aaaaaaaaaa    1560
aaatattagt tgattgtgtg acaatatttt atattaaata taattagtta atttagttca    1620
agttgagtta cattttttaca taccattctt agccgccact tttttatatt tatttgtagg    1680 aataaacttttt catctgtatc aattttcccc gtctaataaa aagggtttga ctttttctta    1740
taatagagtt tttttttttt tgctttaagt tattgtaaaa taattatttt atttttttttg    1800 cctttgtaaa ttatgtatat ttaatgtttt aataggaaaa aatgttatc aaaagcacta    1860 aaagactaaa attaaacaac cataatttgc aaagatgaaa ataaaaaaat aattttgtaa    1920
agataaaaaa tgaaataaaa tagttaaatt ataggaattt aaaagctatt taaatcaaca    1980
aaagttaaag tttctgtaaa aaaagttcaa ttttttttttt tattattgaa aaagttaaag    2040
ctaatgagcg ttcgatttgg gttagtatgt agtatttatt atttttcaaga ttttggattt    2100 tattgtcgat gtttctgatt tgaatataat tattttccat tcaacttgtg attttataag    2160
aaaaaaaaag gtacagaaaa aatcaagcgc ttttttttatt tcaattagtg gaggtttcac    2220
tgaaatgggt aaagaatcta ttttgcaatc acaattatta ccggtattca actgcaacaa    2280
ggaacaaaat tcctttcgta aatatacgga gaggaatcta ttttgacttg ttgaatttat    2340
ggtaaagtag aatttagaat ttaattatga gttgaagtaa ttttgaataa tttatatgtt    2400
aaatataaaa ttttgtacta agttttattc ataactttga ttctataata caaacataca    2460
taagttcaaa aataattttta attaaaatta atttttatcaa ttttttattca aacacgagtc    2520 taatttgctt gatgaattaa gaaaataagg aagaaaatat taaaaactag gagagaagtt    2580
aaagagaatt tcatctttat tattctcagt tgtttcaaaa ataatgaaag gatagctata    2640
taatactgta actgagccaa gaacatattt gccgtccgag taaccttttc ttttcttgtt    2700
ccgttttctc cgccgatgaa gagagggaag ggaatgtatc tttgtattta tgttttcaaa    2760
gagttcgtgc ataaaattgg tttaatcaaa ttttttcataa gattattatt ttatgatttt    2820
ttaaaataaa ttagtaacta tattccgtaa gtcgtacaca gttatatgta gtaagtaaat    2880
tatattttaa taattattat cttaaaattt tcttaagaac ttggttaaaa tattttttgtt    2940 tgaaaaagtt tatgataact tttttttgtt gaaaaaagt ttacgattat ctaactcgta    3000
cttagattat ttctaattgg gatttattga agggttttttt aagtaaagaa attgtttctt    3060
atggtttctt ttttattgga caaatttacg tagcaaagag tgtttcttaa aaacaagaca    3120
tgtatccttt gaaaaaaaac tatttctttg aaataaaaaa taatatttat ctggcacata    3180
ataatgttaa aattaaaatca taattaggta aaaataaaat aaatataaaa gtatgagttt    3240
gttaagtttt ttataatttt ttattattaa agtaaaatta tgtatgattt ttttataatg    3300
atatgatatt ttagggatca caaaaaataa tgtggtgaat acaaaagtaa ctcaaaaaat    3360
tcatttagta aattttcatt ggagatgcta ttattatgct ttctgattgc tttgtccaaa    3420
aaataaagaa tgttttttta tttgaaaatt gaaaatttct gggtcatgtt aagatcttgt    3480
agacggtaac gtcggcctaa agttgtgtga ggggtgttgc atgcaccgat cattaattac    3540
tcgatatgga aaacgactga aataatttaa tttgatgttg ctaatattgg ccatccctct    3600
catcattatt gttttttttat ttgtaacatg acatattctt gtgggtccgc tacgattgg    3660 gtgtttgttg ccaaaaaata caaaatatct gtggaacaag gataaacagt cttgtttgtt    3720
```

-continued

```
taattgattg attgatgagt tgcaagcta tatttttaat ttatttaat taaacttttg    3780
tgttttagtt ctacaatttt attcatcttg atttttttt tacttggcaa aatcatgatt   3840
ttttaatttt tacttatgtt gaaaacaaat ttattgctaa aaaaacattt attctttttt   3900
tagagaaaaa acaaatttgt gatatgtagt gaatcaaatg aaaattttaa acataatata   3960
gaatactcta caaatcaatt ttgagtttct ttatcatttt atttatttat tgacatactt   4020
ctactttctg caaagaccct gactcgtgga agatatagg aaggttatgg aagttagtgt   4080
attgtcatat ctagctatct ttgctaattg aaaaagcctt ccctttgttt acagatctgg   4140
ataaggttgc atgtttattc ttttcaactg tgaatggttc tttgcatctt ttttagtata   4200
tgagattaat gttttaatta ggaagaagct tttagaacat cacccgaatc caattcgttt   4260
tggtttctgt gatcttgatg taaatctata ctaatttggt ttgggcagaa gaaaatgttc   4320
tttgctcaag tcctctagga cgaaaatata aatataacag ggtatatcag atctctattc   4380
ttctgtgggt aatgatagca tgtttctgtt gttttcttat tcttcattgg tcatgataac   4440
ctgctaattc tatttgccac gattgagatg aaaaggtaat gaactagtaa acaataatga   4500
gaagaatatg tcgctactat tgttgaaacg gttacgccag gcacttgagt atgatgcact   4560
attttaatta atgcattttt tttgctttga tgagaacgca cattgttcat tctgattcgg   4620
tgagtttaga aactattgct gataatcctt gatttaagat tttagtcttg ttcatgttca   4680
ttaaaagtgt tgtaaaaaa tgcactgata tgtcatgtgc agattgtgtg aagatggggg   4740
cgggtggccg aactgatgtt cctcctgcca acaggaagtc agaggttgac cctttgaagc   4800
gggtgccatt tgaaaaacct ccatttagtc tcagccaaat caagaaggtc attccacctc   4860
actgtttcca gcgttctgtt ttccgctcat tctcctatgt tgtttacgac ctcaccatag   4920
ccttctgcct ctattatgtt gccacccatt acttccacct ccttcccagc cctctctctt   4980
tcttggcatg gccaatctac tgggctgtcc aaggttgcat ccttactgga gtttgggtca   5040
ttgcccatga gtgtggccac catgcattca gtgactacca gttgcttgat gatattgttg   5100
gccttgtcct ccactccggt ctcctagtcc catactttc atggaaatac agccatcgcc   5160
gtcaccactc caacactggt tctcttgagc gggatgaagt atttgtgcca aagcagaagt   5220
cctgtatcaa gtggtactct aaataccta acaatcctcc aggcagagtc ctcactcttg   5280
ctgtcaccct cacacttggt tggcccttgt acttggcttt aaatgtttct ggaaggcctt   5340
atgatagatt tgcttgccac tatgacccat atggtcccat ttactctgat cgtgaacgac   5400
ttcaaatata tatatcagat gcaggagtac ttgcagtatg ctatgccctt ttccgtcttg   5460
ccatggcaaa aggacttgcc tgggtggtgt gtgtttatgg agttccattg ctagtggtca   5520
atggatttt ggtgttgatt acattcttgc agcatactca ccctgcattg ccacattaca   5580
cttcctctga gtgggactgg ttgagaggag ctttagcaac agtggataga gattatggaa   5640
tcctgaacaa ggtcttccat aatattacag acactcatgt agcacatcac ttgttctcca   5700
caatgccaca ttatcatgca atggaggcta caaaggcaat aaaacccatt tgggagagt    5760
attatcggtt tgatgagact ccatttgtca aggcaatgtg gagagaggca agagagtgta   5820
tttatgtgga gccagatcaa agtaccgaga gcaaaggtgt attttggtac aacaataagt   5880
tgtgatgatt aatgtagccg aggcttcttt gaactttccc ttgtgactgt ttagtatcat   5940
ggttgcttat tgggaataat tttgttgaac cctgatgttg gtagtaagta tctagacagt   6000
tgcatagcgg ttttgtttac agaataagat atagcctctc tgaacagttt gattattgca   6060
ccatggtttg caatcggtgc atgtcgacca agtttctcaa gactgtggag aagcttattc   6120
```

-continued

| | |
|---|---|
| ttgttccagt tcttgaatcc aagttgttac cgtattctgt aagccgaatt ctgcagatat | 6180 |
| ccatcacact ggcggccgct cgagcatgca tctagagggc | 6220 |

<210> SEQ ID NO 4
<211> LENGTH: 4597
<212> TYPE: DNA
<213> ORGANISM: Glycine max

<400> SEQUENCE: 4

| | |
|---|---|
| gtacttttct ctccttatct ctttatcttt attctttcct actttattgc ttaaaccaat | 60 |
| gctatctatg cttcgatctc gccttcttat tttccacttc ccttttctcg cttgatctaa | 120 |
| ccgttttcgc cctccgcgct tcgattgact gagtacatct acgattctct gttctttcat | 180 |
| ttcatagatt tcgtctgatt ttggctaact tggtttctgt tgcggccgat tcttacatat | 240 |
| actgattgtt tagcataaat gaacttgctt gtttagcact atctgcatat tttcgtcacg | 300 |
| catctctttc ggatctaagg atgaatctcc tatttcctcc gtattatttc tcgtatctct | 360 |
| tgttctgtgc taatgctcca gaaaatggca gcattgtctt cttctttgct gtataagtgt | 420 |
| ttgtgttgtg aatctggaag cgattttgcg tgaggtaact tgcgacttca actattatct | 480 |
| ttcagatctc gttaatttat tagctgctat taatttgtgt gtgcagtgtc aaactgaagc | 540 |
| acacgactgc ttagaagtta gaatttgact gactgttcct ctttgatttt ttctttctt | 600 |
| ttctttgctw actcggccta tttaatgatc tttataaata gattagtgga ccacttggtt | 660 |
| agttggtgag ttatgaatat tcgaattttc taccacaagt tgggttaaaa aaatctctgc | 720 |
| aactacacga ggattttta ttttatttag aggaaactat tctgtcatcc ttttccgat | 780 |
| tacacttttc tatcagttgt tttgaaatat acaccttagg aatataatat tacccctttc | 840 |
| ggtcttaata taaatatatt ttaattattt atatttatt taatgaaatt attttaaaa | 900 |
| tactttcatt taatagaatt tttaataaag ttaaagactt ttattgtgta gagtttaacg | 960 |
| aagttaatta gttttcttag taaatgtaaa atatgccttt tttgttgttt ataatggaga | 1020 |
| ttggaaaaaa tatactttaa ttttttttcaa gtgatgaata attatggatg ttttgtcaat | 1080 |
| atttttgtct tgctatacaa ctttcagtct tgccattaaa taattttgaa tgtgttattg | 1140 |
| atatctctga acaatattta gagacgaaca taaattttat atattttata taatttcttt | 1200 |
| ttattacccct tttattatca attttgaaat ttggttaata tctgtgtttc attttgaggt | 1260 |
| ctcaaatttg atataaggag gttcaaaatg cgttgctagc catttaaag attagcagga | 1320 |
| gaggaaatgt ttctggactt aaatttaaaa tatgcttatt tgttttcaa gagagagaga | 1380 |
| tcaatattta tataatacac ttgaattaat atacaccatt gttgcaaaaa aaaaaaaata | 1440 |
| ttagttgatt gtgtgacaat attttatatt aaatataatt agttaattta gttcaagttg | 1500 |
| agttacattt ttacatacca ttcttagccg ccactttttt atatttattt gtaggaataa | 1560 |
| cttttcatct gtatcaattt tccccgtcta ataaaaggg tttgactttt tcttataata | 1620 |
| gagttttttt tttttttgctt taagttattg taaaataatt atttatttt ttttgccttt | 1680 |
| gtaaattatg tatatttaat gttttaatag gaaaaaaatg ttatcaaaag cactaaaaga | 1740 |
| ctaaaattaa acaaccataa tttgcaaaga tgaaaataaa aaaataattt tgtaaagata | 1800 |
| aaaaatgaaa taaaatagtt aaattatagg aatttaaaag ctatttaaat caacaaaagt | 1860 |
| taaagtttct gtaaaaaaag ttcaattttt tttttatta ttgaaaaagt taaagctaat | 1920 |
| gagcgttcga tttgggttag tatgtagtat ttattatttt caagatttg gatttttatg | 1980 |
| tcgatgtttc tgatttgaat ataattattt tccattcaac ttgtgatttt ataagaaaaa | 2040 |

```
aaaaggtaca gaaaaaatca agcgcttttt ttatttcaat tagtggaggt ttcactgaaa    2100
tgggtaaaga atctatttg caatcacaat tattaccggt attcaactgc aacaaggaac     2160
aaaattcctt tcgtaaatat acggagagga atctatttg acttgttgaa tttatggtaa     2220
agtagaattt agaatttaat tatgagttga agtaattttg aataatttat atgttaaata    2280
taaaattttg tactaagttt tattcataac tttgattcta aatacaaac atacataagt     2340 tcaaaaataa ttttaattaa aattaatttt atcaattttt attcaacac gagtctaatt     2400 tgcttgatga attaagaaaa taaggaagaa aatattaaaa actaggagag aagttaaaga    2460
gaatttcatc tttattattc tcagttgttt caaaaataat gaaaggatag ctatataata    2520
ctgtaactga gccaagaaca tatttgccgt ccgagtaacc ttttctttc ttgttccgtt     2580 ttctccgccg atgaagagag ggaagggaat gtatctttgt atttatgttt tcaaagagtt    2640
cgtgcataaa attggtttaa tcaaattttt cataagatta ttattttatg attttttaaa    2700
ataaattagt aactatattc cgtaagtcgt acacagttat atgtagtaag taaattatat    2760
tttaataatt attatcttaa aattttctta agaacttggt taaaatattt ttgtttgaaa    2820
aagtttatga taactttttt ttgttgaaaa aaagtttacg attatctaac tcgtacttag    2880
attatttcta attgggattt attgaagggt tttttaagta aagaaattgt ttcttatggt    2940 ttcttttta ttggacaaat ttacgtagca aagagtgttt cttaaaaaca agacatgtat     3000
cctttgaaaa aaaactattt ctttgaaata aaaaataata tttatctggc acataataat    3060
gttaaaatta aatcataatt aggtaaaaat aaaaataata taaagtatg agtttgttaa     3120 gtttttata attttttatt attaaagtaa aattatgtat gattttttta taatgatatg     3180
atattttagg gatcacaaaa aataatgtgg tgaatacaaa agtaactcaa aaaattcatt    3240
tagtaaattt tcattggaga tgctattatt atgctttctg attgctttgt ccaaaaaata    3300
aagaatgttt ttttatttga aaattgaaaa tttctgggtc atgttaagat cttgtagacg    3360
gtaacgtcgg cctaaagttg tgtgagggt gttgcatgca ccgatcatta attactcgat     3420
atggaaaacg actgaaataa tttaatttga tgttgctaat attggccatc cctctcatca    3480
ttattgtttt tttatttgta acatgacata ttcttgtggg tccgctacgg attgggtgtt    3540
tgttgccaaa aaatacaaaa tatctgtgga acaaggataa acagtcttgt ttgtttaatt    3600
gattgattga tgagtttgca agctatattt ttaatttatt ttaattaaac ttttgtgttt    3660
tagttctaca attttattca tcttgatttt tttttttactt ggcaaaatca tgatttttta   3720
atttttactt atgttgaaaa caaatttatt gctaaaaaaa catttattct tttttagag    3780 aaaaaacaaa tttgtgatat gtagtgaatc aaatgaaaat tttaaacata atatagaata    3840
ctctacaaat caattttgag tttctttatc attttatta tttattgaca tacttctact    3900
ttctgcaaag accctgactc gtggaagata tagggaaggt tatggaagtt agtgtattgt    3960
catatctagc tatctttgct aattgaaaaa gccttccctt tgtttacaga tctggataag    4020
gttgcatgtt tattctttc aactgtgaat ggttctttgc atctttttta gtatatgaga     4080 ttaatgttt aattaggaag aagcttttag aacatcaccc gaatccaatt cgttttggtt     4140
tctgtgatct tgatgtaaat ctatactaat ttggtttggg cagaagaaaa tgttctttgc    4200
tcaagtcctc taggacgaaa atataaatat aacagggtat atcagatctc tattcttctg    4260
tgggtaatga tagcatgttt ctgttgtttt cttattcttc attggtcatg ataacctgct    4320
aattctattt gccacgattg agatgaaaag gtaatgaact agtaaacaat aatgagaaga    4380
atatgtcgct actattgttg aaacggttac gccaggcact tgagtatgat gcactatttt    4440
```

```
aattaatgca ttttttttgc tttgatgaga acgcacattg ttcattctga ttcggtgagt    4500
ttagaaacta ttgctgataa tccttgattt aagattttag tcttgttcat gttcattaaa    4560
agtgttgtaa aaaatgcac tgatatgtca tgtgcag                              4597

<210> SEQ ID NO 5
<211> LENGTH: 191
<212> TYPE: DNA
<213> ORGANISM: Glycine max

<400> SEQUENCE: 5
gtaataattt ttgtgtttct tactcttttt tttttttttt tgtttatgat atgaatctca      60
cacattgttc tgttatgtca tttcttcttc atttggcttt agacaactta aatttgagat     120
ctttattatg tttttgctta tatggtaaag tgattcttca ttatttcatt cttcattgat     180
tgaattgaac a                                                          191

<210> SEQ ID NO 6
<211> LENGTH: 346
<212> TYPE: DNA
<213> ORGANISM: Glycine max

<400> SEQUENCE: 6
ttagttcata ctggcttttt tgtttgttca tttgtcattg aaaaaaaatc ttttgttgat      60
tcaattattt ttatagtgtg tttggaagcc cgtttgagaa aataagaaat cgcatctgga     120
atgtgaaagt tataactatt tagcttcatc tgtcgttgca agttctttta ttggttaaat     180
ttttatagcg tgctaggaaa cccattcgag aaaataagaa atcacatctg gaatgtgaaa     240
gttataactg ttagcttctg agtaaacgtg gaaaaaccac attttggatt tggaaccaaa     300
ttttatttga taaatgacaa ccaaattgat tttgatggat tttgca                   346

<210> SEQ ID NO 7
<211> LENGTH: 142
<212> TYPE: DNA
<213> ORGANISM: Glycine max

<400> SEQUENCE: 7
gtatgtgatt aattgcttct cctatagttg ttcttgattc aattacattt tatttatttg      60
gtaggtccaa gaaaaaaggg aatctttatg cttcctgagg ctgttcttga acatggctct     120 ttttatgtg tcattatctt ag                                              142

<210> SEQ ID NO 8
<211> LENGTH: 1228
<212> TYPE: DNA
<213> ORGANISM: Glycine max

<400> SEQUENCE: 8
taacaaaaat aaatagaaaa tagtgggtga acacttaaat gcgagatagt aatacctaaa      60 aaagaaaaa aatataggta taataaataa tataactttc aaaataaaaa gaaatcatag     120
agtctagcgt agtgtttgga gtgaaatgat gttcacctac cattactcaa agattttgtt     180 gtgtcccta gttcattctt attattttac atatcttact tgaaaagact ttttaattat     240
tcattgagat cttaaagtga ctgttaaatt aaaataaaaa acaagtttgt taaaacttca     300
aataaataag agtgaaggga gtgtcatttg tcttctttct tttattgcgt tattaatcac     360
gtttctcttc tctttttttt tttcttctc tgctttccac ccattatcaa gttcatgtga     420
agcagtggcg gatctatgta aatgagtggg gggcaattgc acccacaaga ttttattttt     480
```

-continued

```
tatttgtaca ggaataataa aataaaactt tgcccccata aaaataaaat atttttctt       540 aaaataatgc aaaataaata taagaaataa aagagaata aattattatt aattttatta       600
ttttgtactt tttatttagt ttttttagcg gttagatttt tttttcatga cattatgtaa      660
tcttttaaaa gcatgtaata ttttttatttt gtgaaaataa atataaatga tcatattagt    720
ctcagaatgt ataaactaat aataatttta tcactaaaag aaattctaat ttagtccata     780
aataagtaaa acaagtgaca attatatttt atatttactt aatgtgaaat aatacttgaa    840
cattataata aaacttaatg acaggagata ttacatagtg ccataaagat attttaaaaa   900
ataaaatcat aatacactg tactactata taatattcga tatatatttt taacatgatt      960
ctcaatagaa aaattgtatt gattatattt tattagacat gaatttacaa gccccgtttt    1020
tcatttatag ctcttacctg tgatctattg ttttgcttcg ctgttttgt tggtcaaggg     1080 acttagatgt cacaatatta atactagaag taaatatttta tgaaaacatg taccttacct   1140
caacaaagaa agtgtggtaa gtggcaacac acgtgttgca ttttttggccc agcaataaca   1200 cgtgtttttg tggtgtacta aaatggac                                        1228
```

<210> SEQ ID NO 9
<211> LENGTH: 625
<212> TYPE: DNA
<213> ORGANISM: Glycine max

<400> SEQUENCE: 9

```
gtacatttta ttgcttattc acctaaaaac aatacaatta gtacatttgt tttatctctt     60
ggaagttagt cattttcagt tgcatgattc taatgctctc tccattctta aatcatgttt    120
tcacacccac ttcatttaaa ataagaacgt gggtgttatt ttaatttcta ttcactaaca   180
tgagaaatta acttatttca agtaataatt ttaaaatatt tttatgctat tatttttatta   240 caaataatta tgtatattaa gtttattgat tttataataa ttatattaaa attatatcga    300 tattaattt tgattcactg atagtgtttt atattgttag tactgtgcat ttatttttaaa   360 attggcataa ataatatatg taaccagctc actatactat actgggagct tggtggtgaa    420
aggggttccc aaccctcctt tctaggtgta catgctttga tacttctggt accttcttat    480
atcaatataa attatatttt gctgataaaa aaacatggtt aaccattaaa ttctttttt     540 aaaaaaaaaa ctgtatctaa actttgtatt attaaaaaga agtctgagat taacaataaa    600
ctaacactca tttggattca ctgca                                          625
```

<210> SEQ ID NO 10
<211> LENGTH: 98
<212> TYPE: DNA
<213> ORGANISM: Glycine max

<400> SEQUENCE: 10

```
ggtgagtgat ttttgactt ggaagacaac aacacattat tattataata tggttcaaaa      60
caatgacttt ttctttatga tgtgaactcc atttttta                              98
```

<210> SEQ ID NO 11
<211> LENGTH: 115
<212> TYPE: DNA
<213> ORGANISM: Glycine max

<400> SEQUENCE: 11

```
ggtaactaaa ttactcctac attgttactt tttcctcctt ttttttatta tttcaattct      60
ccaattggaa atttgaaata gttaccataa ttatgtaatt gtttgatcat gtgca          115
```

```
<210> SEQ ID NO 12
<211> LENGTH: 148
<212> TYPE: DNA
<213> ORGANISM: Glycine max
<220> FEATURE:
<223> OTHER INFORMATION: FAD3-1B intron 3c

<400> SEQUENCE: 12
gtaatctcac tctcacactt tctttataca tcgcacgcca gtgtgggtta tttgcaacct      60
acaccgaagt aatgccctat aattaatgag gttaacacat gtccaagtcc aatatttttgt   120 tcacttattt gaacttgaac atgtgtag                                       148

<210> SEQ ID NO 13
<211> LENGTH: 361
<212> TYPE: DNA
<213> ORGANISM: Glycine max
<220> FEATURE:
<223> OTHER INFORMATION: FAD3-1B intron 4

<400> SEQUENCE: 13
gtatcccatt taacacaatt tgtttcatta acattttaag agaattttttt tttcaaaata    60 gttttcgaaa ttaagcaaat accaagcaaa ttgttagatc tacgcttgta cttgttttaa   120
agtcaaattc atgaccaaat tgtcctcaca agtccaaacc gtccactatt ttattttcac   180
ctactttata gcccaatttg ccatttggtt acttcagaaa agagaacccc atttgtagta   240
aatatattat ttatgaatta tggtagtttc aacataaaac atacttatgt gcagttttgc   300
catccttcaa aagaaggtag aaacttactc catgttactc tgtctatatg taatttcaca   360
g                                                                    361

<210> SEQ ID NO 14
<211> LENGTH: 1037
<212> TYPE: DNA
<213> ORGANISM: Glycine max

<400> SEQUENCE: 14
gtaacaaaaa taaatagaaa atagtgagtg aacacttaaa tgttagatac taccttcttc     60 ttctttttt tttttttttt gaggttaatg ctagataata gctagaaaga gaagaaaga    120 caaatatagg taaaaataaa taatataacc tgggaagaag aaaacataaa aaagaaata   180 atagagtcta cgtaatgttt ggattttttga gtgaaatggt gttcacctac cattactcaa   240
agattctgtt gtctacgtag tgtttggact ttggagtgaa atggtgttca cctaccatta   300
ctcagattct gttgtgtccc ttagttactg tcttatattc ttagggtata ttctttatttt  360 tacatccttt tcacatctta cttgaaaaga ttttaattat tcattgaaat attaacgtga   420
cagttaaatt aaaataataa aaaattcgtt aaaacttcaa ataaataaga gtgaaaggat   480
catcattttt cttctttctt ttattgcgtt attaatcatg cttctcttct ttttttttctt  540 cgctttccac ccatatcaaa ttcatgtgaa gtatgagaaa atcacgattc aatggaaagc   600
tacaggaacy tttttttgttt tgttttttata atcggaatta atttatactc catttttttca 660 caataaatgt tacttagtgc cttaaagata atatttgaaa aattaaaaaa attattaata   720
cactgtacta ctatataata tttgacatat atttaacatg attttctatt gaaaatttgt   780
atttattatt tttaatcaa aacccataag gcattaattt acaagaccca ttttcattt     840 atagctttac ctgtgatcat ttatagcttt aagggacttta gatgttacaa tcttaattac   900
aagtaaatat ttatgaaaaa catgtgtctt accccttaac cttacctcaa caagaaagt    960
```

-continued

```
gtgataagtg gcaacacacg tgttgctttt ttggcccagc aataacacgt gttttttgtgg    1020 tgtacaaaaa tggacag                                                     1037

<210> SEQ ID NO 15
<211> LENGTH: 4497
<212> TYPE: DNA
<213> ORGANISM: Glycine max

<400> SEQUENCE: 15
cttgcttggt aacaacgtcg tcaagttatt attttgttct ttttttttt atcatatttc     60 ttattttgtt ccaagtatgt catattttga tccatcttga caagtagatt gtcatgtagg   120
aataggaata tcactttaaa ttttaaagca ttgattagtc tgtaggcaat attgtcttct   180
tcttcctcct tattaatatt ttttattctg ccttcaatca ccagtatggg agatggatg    240 taatactaaa taccatagtt gttctgcttg aagtttagtt gtatagttgt tctgcttgaa   300
gtttagttgt gtgtaatgtt tcagcgttgg cttccctgt aactgctaca atggtactga   360
atatatattt tttgcattgt tcatttttt cttttactta atcttcattg ctttgaaatt    420
aataaaacaa aaagaaggac cgaatagttt gaagtttgaa ctattgccta ttcatgtaac   480
ttattcaccc aatcttatat agttttctg gtagagatca ttttaaattg aaggatataa   540
attaagagga aatacttgta tgtgatgtgt ggcaatttgg aagatcatgc gtagagagtt   600
taatggcagg ttttgcaaat tgacctgtag tcataattac actgggccct ctcggagttt   660 tgtgccttt tgttgtcgct gtgtttggtt ctgcatgtta gcctcacaca gatatttagt    720
agttgttgtt ctgcatataa gcctcacacg tatactaaac gagtgaacct caaaatcatg   780
gccttacacc tattgagtga aattaatgaa cagtgcatgt gagtatgtga ctgtgacaca   840 accccggtt tcatattgc aatgtgctac tgtggtgatt aaccttgcta cactgtcgtc    900
cttgtttgtt tccttatgta tattgatacc ataaattatt actagtatat cattttatat   960
tgtccatacc attacgtgtt tatagtctct ttatgacatg taattgaatt ttttaattat   1020
aaaaaataat aaaacttaat tacgtactat aaagagatgc tcttgactag aattgtgatc   1080
tcctagtttc ctaaccatat actaatattt gcttgtattg atagcccctc cgttcccaag   1140
agtataaaac tgcatcgaat aatacaagcc actaggcatg gtaaattaaa ttgtgcctgc   1200
acctcgggat atttcatgtg gggttcatca tatttgttga ggaaaagaaa ctcccgaaat   1260
tgaattatgc atttatatat cctttttcat ttctagattt cctgaaggct taggtgtagg   1320
cacctagcta gtagctacaa tatcagcact tctctctatt gataaacaat tggctgtaat   1380
gccgcagtag aggacgatca caacatttcg tgctggttac ttttttgtttt atggtcatga   1440 tttcactctc tctaatctct ccattcattt tgtagttgtc attatcttta gattttttcac   1500 tacctggttt aaaattgagg gattgtagtt ctgttggtac atattacaca ttcagcaaaa   1560
caactgaaac tcaactgaac ttgtttatac tttgacacag gtctagcaa aggaaacaac    1620 aatgggaggt agaggtcgtg tggcaaagtg gaagttcaag ggaagaagcc tctctcaagg   1680
gttccaaaca caaagccacc attcactgtt ggccaactca agaaagcaat tccaccacac   1740
tgctttcagc gctccctcct cacttcattc tcctatgttg tttatgacct tcatttgcc    1800 ttcattttct acattgccac cacctacttc cacctcctc ctcaaccctt tccctcatt     1860 gcatggccaa tctattgggt tctccaaggt tgccttctca ctggtgtgtg ggtgattgct   1920
cacgagtgtg gtcaccatgc cttcagcaag taccaatggg ttgatgatgt tgtgggtttg   1980
acccttcact caacactttt agtcccttat ttctcatgga aaataagcca tcgccgccat   2040
```

```
cactccaaca caggttccct tgaccgtgat gaagtgtttg tcccaaaacc aaaatccaaa    2100
gttgcatggt tttccaagta cttaaacaac cctctaggaa gggctgtttc tcttctcgtc    2160
acactcacaa tagggtggcc tatgtattta gccttcaatg tctctggtag accctatgat    2220
agttttgcaa gccactacca cccttatgct cccatatatt ctaaccgtga gaggcttctg    2280
atctatgtct ctgatgttgc tttgttttct gtgacttact ctctctaccg tgttgcaacc    2340
ctgaaagggt tggtttggct gctatgtgtt tatggggtgc ctttgctcat tgtgaacggt    2400
tttcttgtga ctatcacata tttgcagcac acacactttg ccttgcctca ttacgattca    2460
tcagaatggg actggctgaa gggagctttg gcaactatgg acagagatta tgggattctg    2520
aacaaggtgt tcatcacat aactgatact catgtggctc accatctctt ctctacaatg    2580
ccacattacc atgcaatgga ggcaaccaat gcaatcaagc caatattggg tgagtactac    2640
caatttgatg acacaccatt ttacaaggca ctgtggagag aagcgagaga gtgcctctat    2700
gtggagccag atgaaggaac atccgagaag ggcgtgtatt ggtacaggaa caagtattga    2760
tggagcaacc aatgggccat agtgggagtt atggaagttt tgtcatgtat tagtacataa    2820
ttagtagaat gttataaata agtggatttg ccgcgtaatg actttgtgtg tattgtgaaa    2880
cagcttgttg cgatcatggt tataatgtaa aaataattct ggtattaatt acatgtggaa    2940
agtgttctgc ttatagcttt ctgcctaaaa tgcacgctgc acgggacaat atcattggta    3000 attttttttaa aatctgaatt gaggctactc ataatactat ccataggaca tcaaagacat    3060
gttgcattga ctttaagcag aggttcatct agaggattac tgcataggct tgaactacaa    3120
gtaatttaag ggacgagagc aactttagct ctaccacgtc gttttacaag gttattaaaa    3180
tcaaattgat cttattaaaa ctgaaaattt gtaataaaat gctattgaaa aattaaaata    3240
tagcaaacac ctaaattgga ctgattttta gattcaaatt taataattaa tctaaattaa    3300
acttaaattt tataatatat gtcttgtaat atatcaagtt ttttttttta ttattgagtt    3360
tggaaacata taataaggaa cattagttaa tattgataat ccactaagat cgacttagta    3420
ttacagtatt tggatgattt gtatgagata ttcaaacttc actcttatca taatagagac    3480
aaaagttaat actgatggtg gagaaaaaaa aatgttattg ggagcatatg gtaagataag    3540
acggataaaa atatgctgca gcctggagag ctaatgtatt ttttggtgaa gttttcaagt    3600
gacaactatt catgatgaga acacaataat attttctact tacctatccc acataaaata    3660 ctgatttttaa taatgatgat aaataatgat taaaatattt gattctttgt taagagaaat    3720
aaggaaaaca taaatattct catggaaaaa tcagcttgta ggagtagaaa ctttctgatt    3780
ataattttaa tcaagtttaa ttcattcttt taatttt att attagtacaa aatcattctc    3840
ttgaatttag agatgtatgt tgtagcttaa tagtaatttt ttattttat aataaaattc    3900 aagcagtcaa atttcatcca aataatcgtg ttcgtgggtg taagtcagtt attccttctt    3960
atcttaatat acacgcaaag gaaaaaataa aaataaaatt cgaggaagcg cagcagcagc    4020
tgataccacg ttggttgacg aaactgataa aaagcgctgt cattgtgtct tgtttgatc    4080 atcttcacaa tcacatctcc agaacacaaa gaagagtgac ccttcttctt gttattccac    4140
ttgcgttagg tttctacttt cttctctctc tctctctctc tcttcattcc tcattttcc    4200 ctcaaacaat caatcaattt tcattcagat tcgtaaattt ctcgattaga tcacggggtt    4260
aggtctccca ctttatcttt tcccaagcct ttctcttttcc cctttccct gtctgcccca    4320 taaaattcag gatcggaaac gaactggggtt cttgaatttc actctagatt ttgacaaatt    4380
```

```
cgaagtgtgc atgcactgat gcgacccact cccccttttt tgcattaaac aattatgaat    4440
tgaggttttt cttgcgatca tcattgcttg aattgaatca tattaggttt agattct      4497

<210> SEQ ID NO 16
<211> LENGTH: 18
<212> TYPE: DNA
<213> ORGANISM: Artificial sequence
<220> FEATURE:
<223> OTHER INFORMATION: PCR primer

<400> SEQUENCE: 16
atacaagcca ctaggcat                                                    18

<210> SEQ ID NO 17
<211> LENGTH: 26
<212> TYPE: DNA
<213> ORGANISM: Artificial sequence
<220> FEATURE:
<223> OTHER INFORMATION: PCR primer

<400> SEQUENCE: 17
gattggccat gcaatgaggg aaaagg                                           26

<210> SEQ ID NO 18
<211> LENGTH: 778
<212> TYPE: DNA
<213> ORGANISM: Artificial sequence
<220> FEATURE:
<221> NAME/KEY: misc_feature
<222> LOCATION: (1)..(778)
<223> OTHER INFORMATION: unsure at all n locations
<220> FEATURE:
<223> OTHER INFORMATION: PCR primer

<400> SEQUENCE: 18
atacaagcca ctaggcatgg taaattaaat tgtgcctgca cctcgggata tttcatgtgg     60
ggttcatcat atttgttgag gaaaagaaac tcccgaaatt gaattatgca tttatatatc    120 cttttttcatt tctagatttc ctgaaggctt aggtgtaggc acctagctag tagctacaat   180
atcagcactt ctctctattg ataaacaatt ggctgtaatg ccgcagtaga ggacgatcac    240
aacatttcgt gctggttact ttttgtttta tggtcatgat ttcactctct ctaatctctc    300
cattcatttt gtagttgtca ttatctttag attttttcact acctggttta aaattgaggg   360
attgtagttc tgttggtaca tattacacat tcagcaaaac aactgaaact caactgaact    420
tgtttatact ttgacacagg gtctagcaaa ggaaacaaca atgggaggta gaggtcgtgt    480
ggccaaagtg gaagttcaag ggaagaagcc tctctcaagg gttccaaaca caaagccacc    540
attcactgtt ggccaactca agaaagcaat tccaccacac tgctttcagc gctccctcct    600
cacttcattc tcctatgttg tttatgacct tcatttgcc ttcatttcct acattgccac     660
cacctacttc cacctccttc ctcaacccctt ttccctcatt gcatggccaa tcaagccgaa   720
ttctgcagat atccatcaca tggcggcggn tgngngaggn ntntanaggg cccaattc      778

<210> SEQ ID NO 19
<211> LENGTH: 2463
<212> TYPE: DNA
<213> ORGANISM: Glycine max

<400> SEQUENCE: 19
actatagggc acgcgtggtc gacggcccgg gctggtcctc ggtgtgactc agccccaagt     60
gacgccaacc aaacgcgtcc taactaaggt gtagaagaaa cagatagtat ataagtatac    120
```

```
catataagag gagagtgagt ggagaagcac ttctcctttt tttttctctg ttgaaattga      180
aagtgttttc cgggaaataa ataaaataaa ttaaaatctt acacactcta ggtaggtact      240
tctaatttaa tccacacttt gactctatat atgttttaaa aataattata atgcgtactt      300
acttcctcat tatactaaat ttaacatcga tgattttatt ttctgtttct cttctttcca      360
cctacataca tcccaaaatt tagggtgcaa ttttaagttt attaacacat gtttttagct      420
gcatgctgcc tttgtgtgtg ctcaccaaat tgcattcttc tctttatatg ttgtatttga      480
attttcacac catatgtaaa caagattacg tacgtgtcca tgatcaaata caaatgctgt      540
cttatactgg caatttgata aacagccgtc cattttttct ttttctcttt aactatatat      600
gctctagaat ctctgaagat tcctctgcca tcgaatttct ttcttggtaa caacgtcgtc      660
gttatgttat tattttattc tatttttatt ttatcatata tatttcttat tttgttcgaa      720
gtatgtcata ttttgatcgt gacaattaga ttgtcatgta ggagtaggaa tatcacttta      780
aaacattgat tagtctgtag gcaatattgt cttcttttc ctcctttatt aatatatttt       840
gtcgaagttt taccacaagg ttgattcgct ttttttgtcc cttctctcttg ttctttttac     900 ctcaggtatt ttagtctttc atggattata agatcactga gaagtgtatg catgtaatac      960
taagcaccat agctgttctg cttgaattta tttgtgtgta aattgtaatg tttcagcgtt     1020
ggctttccct gtagctgcta caatggtact gtatatctat tttttgcatt gttttcattt     1080
tttcttttac ttaatcttca ttgctttgaa attaataaaa caatataata tagtttgaac     1140
tttgaactat tgcctattca tgtaattaac ttattcactg actcttattg ttttctggt     1200 agaattcatt ttaaattgaa ggataaatta agaggcaata cttgtaaatt gacctgtcat     1260
aattacacag gaccctgttt tgtgcctttt tgtctctgtc tttggttttg catgttagcc     1320
tcacacagat atttagtagt tgttctgcat acaagcctca cacgtatact aaaccagtgg     1380
acctcaaagt catggcctta cacctattgc atgcgagtct gtgacacaac ccctggtttc     1440
catattgcaa tgtgctacgc cgtcgtcctt gtttgtttcc atatgtatat tgataccatc     1500
aaattattat atcatttata tggtctggac cattacgtgt actctttatg acatgtaatt     1560 gagttttta attaaaaaaa tcaatgaaat ttaactacgt agcatcatat agagataatt      1620
gactagaaat ttgatgactt attctttcct aatcatattt tcttgtattg atagccccgc     1680
tgtccctttt aaactcccga gagagtataa aactgcatcg aatattacaa gatgcactct     1740
tgtcaaatga agggggggaa atgatactac aagccactag gcatggtatg atgctaaatt     1800
aaattgtgcc tgcaccccag gatatttcat gtgggattca tcatttattg aggaaaactc     1860
tccaaattga atcgtgcatt tatatttttt ttccatttct agatttcttg aaggcttatg     1920
gtataggcac ctacaattat cagcacttct ctctattgat aaacaattgg ctgtaatacc     1980
acagtagaga acgatcacaa cattttgtgc tggttacctt ttgttttatg gtcatgattt     2040
cactctctct aatctgtcac ttccctccat tcattttgta cttctcatat ttttcacttc     2100
ctggttgaaa attgtagttc tcttggtaca tactagtatt agacattcag caacaacaac     2160
tgaactgaac ttctttatac tttgacacag ggtctagcaa aggaaacaat aatgggaggt     2220
ggaggccgtg tggccaaagt tgaaattcag cagaagaagc ctctctcaag ggttccaaac     2280
acaaagccac cattcactgt tggccaactc aagaaagcca ttccaccgca ctgctttcag     2340
cgttccctcc tcacttcatt gtcctatgtt gtttatgacc tttcattggc tttcattttc     2400
tacattgcca ccacctactt ccacctcctc cctcacccct tttccctcat tgcatggcca     2460
atc                                                                    2463
```

```
<210> SEQ ID NO 20
<211> LENGTH: 44
<212> TYPE: DNA
<213> ORGANISM: Artificial sequence
<220> FEATURE:
<223> OTHER INFORMATION: PCR primer

<400> SEQUENCE: 20
cuacuacuac uactcgagac aaagccttta gcctttagcc tatg          44

<210> SEQ ID NO 21
<211> LENGTH: 36
<212> TYPE: DNA
<213> ORGANISM: Artificial sequence
<220> FEATURE:
<223> OTHER INFORMATION: PCR primer

<400> SEQUENCE: 21
caucaucauc auggatccca tgtctctcta tgcaag                   36

<210> SEQ ID NO 22
<211> LENGTH: 1704
<212> TYPE: DNA
<213> ORGANISM: Glycine max

<400> SEQUENCE: 22
actatagggc acgcgtggtc gacggcccgg gctggtcctc ggtgtgactc agccccaagt    60
gacgccaacc aaacgcgtcc taactaaggt gtagaagaaa cagatagtat ataagtatac   120
catataagag gagagtgagt ggagaagcac ttctcctttt ttttttctctg ttgaaattga  180 aagtgttttc cgggaaataa ataaaataaa ttaaaatctt acacactcta ggtaggtact   240
tctaatttaa tccacacttt gactctatat atgttttaaa aataattata atgcgtactt   300
acttcctcat tatactaaat ttaacatcga tgatttatt ttctgtttct cttctttcca    360
cctacataca tcccaaaatt tagggtgcaa ttttaagttt attaacacat gttttagct    420 gcatgctgcc tttgtgtgtg ctcaccaaat tgcattcttc tctttatatg ttgtatttga   480
attttcacac catatgtaaa caagattacg tacgtgtcca tgatcaaata caaatgctgt   540
cttatactgg caatttgata aacagccgtc cattttttct ttttctcttt aactatatat   600
gctctagaat ctctgaagat tcctctgcca tcgaatttct tcttggtaa caacgtcgtc    660 gttatgttat tatttttattc tatttttatt ttatcatata tatttcttat tttgttcgaa   720
gtatgtcata ttttgatcgt gacaattaga ttgtcatgta ggagtaggaa atcactttta   780
aaacattgat tagtctgtag gcaatattgt cttcttttc ctccttttatt aatatattt    840 gtcgaagttt taccacaagg ttgattcgct ttttttgtcc cttttctctg ttctttttac    900
ctcaggtatt ttagtctttc atggattata agatcactga gaagtgtatg catgtaatac    960
taagcaccat agctgttctg cttgaattta tttgtgtgta aattgtaatg tttcagcgtt   1020
ggctttccct gtagctgcta caatggtact gtatatctat tttttgcatt gttttcattt   1080
tttcttttac ttaatcttca ttgctttgaa attaataaaa caatataata tagtttgaac   1140
tttgaactat tgcctattca tgtaattaac ttattcactg actcttattg ttttttctggt  1200 agaattcatt ttaaattgaa ggataaatta agaggcaata cttgtaaatt gacctgtcat   1260
aattacacag gaccctgttt tgtgccttt tgtctctgtc tttggttttg catgttagcc    1320
tcacacagat atttagtagt tgttctgcat acaagcctca cacgtatact aaaccagtgg   1380
acctcaaagt catggcctta cacctattgc atgcgagtct gtgacacaac ccctggtttc   1440
```

```
catattgcaa tgtgctacgc cgtcgtcctt gtttgtttcc atatgtatat tgataccatc    1500
aaattattat atcatttata tggtctggac cattacgtgt actctttatg acatgtaatt    1560
gagtttttta attaaaaaaa tcaatgaaat ttaactacgt agcatcatat agagataatt    1620
gactagaaat ttgatgactt attctttcct aatcatattt tcttgtattg atagccccgc    1680
tgtccctttt aaactcccga gaga                                           1704
```

<210> SEQ ID NO 23
<211> LENGTH: 4010
<212> TYPE: DNA
<213> ORGANISM: Glycine max

<400> SEQUENCE: 23

```
acaaagcctt tagcctatgc tgccaataat ggataccaac aaaagggttc ttcttttgat      60
tttgatccta gcgctcctcc accgtttaag attgcagaaa tcagagcttc aataccaaaa     120
cattgctggg tcaagaatcc atggagatcc ctcagttatg ttctcaggga gtgcttgta      180 attgctgcat tggtggctgc agcaattcac ttcgacaact ggcttctctg ctaatctat      240 tgccccattc aaggcacaat gttctgggct ctctttgttc ttggacatga ttggtaataa     300 ttttgtgtt tcttactctt ttttttttt ttttgtttat gatatgaatc tcacacattg      360
ttctgttatg tcatttcttc ttcatttggc tttagacaac ttaaatttga gatctttatt     420 atgttttgc ttatatggta aagtgattct tcattatttc attcttcatt gattgaattg     480
aacagtggcc atgaagcttt tcagatagc cctttgctga atagcctggt gggacacatc      540
ttgcattcct caattcttgt gccataccat ggatggtag ttcatactgg ctttttgtt       600 tgttcatttg tcattgaaaa aaaatctttt gttgattcaa ttatttttat agtgtgtttg     660
gaagcccgtt tgagaaaata gaaatcgca tctggaatgt gaaagttata actatttagc      720
ttcatctgtc gttgcaagtt cttttattgg ttaaattttt atagcgtgct aggaaaccca     780
ttcgagaaaa taagaaatca catctggaat gtgaaagtta aactgttag cttctgagta      840 aacgtggaaa aaccacattt tggatttgga accaaatttt atttgataaa tgacaaccaa     900
attgattttg atggatttg caggagaatt agccacagaa ctcaccatga aaaccatgga     960
cacattgaga aggatgagtc atgggttcca gtatgtgatt aattgcttct cctatagttg    1020
ttcttgattc aattacattt tatttatttg gtaggtccaa gaaaaagggg aatctttatg    1080
cttcctgagg ctgttcttga acatggctct ttttttatgtg tcattatctt agttaacaga    1140
gaagatttac aagaatctag acagcatgac aagactcatt agattcactg tgccatttcc    1200 atgttttgtgt atccaattta tttggtgagt gattttttga cttggaagac aacaacacat    1260
tattattata atatggttca aaacaatgac ttttctttta tgatgtgaac tccattttt     1320 agttttcaag aagccccgga aggaaggct ctcacttcaa tccctacagc aatctgtttc      1380
cacccagtga gagaaaagga atagcaatat caacactgtg ttgggctacc atgttttctc    1440
tgcttatcta tctctcattc attaactagt ccacttctag tgctcaagct ctatggaatt    1500
ccatattggg taactaaatt actcctacat tgttactttt tcctcctttt ttttattatt    1560
tcaattctcc aattggaaat ttgaaatagt taccataatt atgtaattgt ttgatcatgt    1620
gcagatgttt gttatgtggc tggacttttgt cacatacttg catcaccatg gtcaccacca    1680
gaaactgcct tggtaccgcg gcaaggtaac aaaaataaat agaaatagt gggtgaacac      1740 ttaaatgcga gatagtaata cctaaaaaaa gaaaaaata taggtataat aaataatata     1800
actttcaaaa taaaaagaaa tcatagagtc tagcgtagtg tttggagtga aatgatgttc    1860
```

```
acctaccatt actcaaagat tttgttgtgt cccttagttc attcttatta ttttacatat   1920
cttacttgaa aagactttt  aattattcat tgagatctta aagtgactgt taaattaaaa   1980
taaaaaacaa gtttgttaaa acttcaaata aataagagtg aagggagtgt catttgtctt   2040
ctttctttta ttgcgttatt aatcacgttt ctcttctctt tttttttttt cttctctgct   2100
ttccacccat tatcaagttc atgtgaagca gtggcggatc tatgtaaatg agtgggggggc  2160
aattgcaccc acaagatttt attttttatt tgtacaggaa taataaaata aaactttgcc   2220
cccataaaaa ataaatattt tttcttaaaa taatgcaaaa taaatataag aaataaaaag   2280
agaataaatt attattaatt ttattatttt gtacttttta tttagttttt ttagcggtta   2340
gattttttt  tcatgacatt atgtaatctt ttaaaagcat gtaatatttt tattttgtga   2400
aaataaatat aaatgatcat attagtctca gaatgtataa actaataata attttatcac   2460
taaaagaaat tctaatttag tccataaata agtaaaacaa gtgacaatta tattttatat   2520
ttacttaatg tgaaataata cttgaacatt ataataaaac ttaatgacag gagatattac   2580
atagtgccat aaagatattt taaaaaataa atcattaat  acactgtact actatataat   2640
attcgatata tattttttaac atgattctca atagaaaaat tgtattgatt atattttatt  2700
agacatgaat ttacaagccc cgttttttcat ttatagctct tacctgtgat ctattgtttt  2760
gcttcgctgt ttttgttggt caagggactt agatgtcaca atattaatac tagaagtaaa   2820
tatttatgaa aacatgtacc ttacctcaac aaagaaagtg tggtaagtgg caacacacgt   2880
gttgcatttt tggcccagca ataacacgtg tttttgtggt gtactaaaat ggacaggaat   2940
ggagttattt aagaggtggc ctcaccactg tggatcgtga ctatggttgg atcaataaca   3000
ttcaccatga cattggcacc catgttatcc accatctttt cccccaaatt cctcattatc   3060
acctcgttga agcggtacat tttattgctt attcacctaa aaacaataca attagtacat   3120
ttgttttatc tcttggaagt tagtcatttt cagttgcatg attctaatgc tctctccatt   3180
cttaaatcat gttttcacac ccacttcatt taaaataaga acgtgggtgt tattttaatt   3240
tctattcact aacatgagaa attaacttat ttcaagtaat aattttaaaa tattttttatg  3300
ctattatttt attacaaata attatgtata ttaagtttat tgatttata ataattatat   3360
taaaattata tcgatattaa ttttttgattc actgatagtg ttttatattg ttagtactgt  3420
gcatttattt taaaattggc ataaataata tatgtaacca gctcactata ctatactggg   3480
agcttggtgg tgaaaggggt tcccaaccct cctttctagg tgtacatgct ttgatacttc   3540
tggtaccttc ttatatcaat ataaattata ttttgctgat aaaaaaacat ggttaaccat   3600
taaattcttt ttttaaaaaa aaactgtat  ctaaactttg tattattaaa aagaagtctg   3660
agattaacaa taaactaaca ctcatttgga ttcactgcag acacaagcag caaaaccagt   3720
tcttggagat tactaccgtg agccagaaag atctgcgcca ttaccatttc atctaataaa   3780
gtatttaatt cagagtatga gacaagacca cttcgtaagt gacactggag atgttgttta   3840
ttatcagact gattctctgc tcctccactc gcaacgagac tgagtttcaa acttttttggg  3900
ttattattta ttgattctag ctactcaaat tacttttttt ttaatgttat gttttttgga   3960
gtttaacgtt ttctgaacaa cttgcaaatt acttgcatag agagacatgg              4010
```

<210> SEQ ID NO 24
<211> LENGTH: 34
<212> TYPE: DNA
<213> ORGANISM: Artificial sequence
<220> FEATURE:
<223> OTHER INFORMATION: PCR primer

<400> SEQUENCE: 24
acgaattcct cgaggtaaat taaattgtgc ctgc                         34

<210> SEQ ID NO 25
<211> LENGTH: 33
<212> TYPE: DNA
<213> ORGANISM: Artificial sequence
<220> FEATURE:
<223> OTHER INFORMATION: PCR primer

<400> SEQUENCE: 25
gcgagatcta tcgatctgtg tcaaagtata aac                          33

<210> SEQ ID NO 26
<211> LENGTH: 19
<212> TYPE: DNA
<213> ORGANISM: Artificial sequence
<220> FEATURE:
<223> OTHER INFORMATION: PCR primer

<400> SEQUENCE: 26
catgctttct gtgcttctc                                          19

<210> SEQ ID NO 27
<211> LENGTH: 19
<212> TYPE: DNA
<213> ORGANISM: Artificial sequence
<220> FEATURE:
<223> OTHER INFORMATION: PCR primer

<400> SEQUENCE: 27
gttgatccaa ccatagtcg                                          19

<210> SEQ ID NO 28
<211> LENGTH: 36
<212> TYPE: DNA
<213> ORGANISM: Artificial sequence
<220> FEATURE:
<223> OTHER INFORMATION: PCR primer

<400> SEQUENCE: 28
gcgatcgatg tatgatgcta aattaaattg tgcctg                       36

<210> SEQ ID NO 29
<211> LENGTH: 30
<212> TYPE: DNA
<213> ORGANISM: Artificial sequence
<220> FEATURE:
<223> OTHER INFORMATION: PCR primer

<400> SEQUENCE: 29
gcggaattcc tgtgtcaaag tataaagaag                              30

<210> SEQ ID NO 30
<211> LENGTH: 30
<212> TYPE: DNA
<213> ORGANISM: Artificial sequence
<220> FEATURE:
<223> OTHER INFORMATION: PCR primer

<400> SEQUENCE: 30
gatcgatgcc cggggtaata atttttgtgt                              30

<210> SEQ ID NO 31
<211> LENGTH: 29
<212> TYPE: DNA
<213> ORGANISM: Artificial sequence
<220> FEATURE:
<223> OTHER INFORMATION: PCR primer

<400> SEQUENCE: 31
cacgcctcga gtgttcaatt caatcaatg                            29

<210> SEQ ID NO 32
<211> LENGTH: 24
<212> TYPE: DNA
<213> ORGANISM: Artificial sequence
<220> FEATURE:
<223> OTHER INFORMATION: PCR primer

<400> SEQUENCE: 32
cactcgagtt agttcatact ggct                                 24

<210> SEQ ID NO 33
<211> LENGTH: 25
<212> TYPE: DNA
<213> ORGANISM: Artificial sequence
<220> FEATURE:
<223> OTHER INFORMATION: PCR primer

<400> SEQUENCE: 33
cgcatcgatt gcaaaatcca tcaaa                                25

<210> SEQ ID NO 34
<211> LENGTH: 38
<212> TYPE: DNA
<213> ORGANISM: Artificial sequence
<220> FEATURE:
<223> OTHER INFORMATION: PCR primer

<400> SEQUENCE: 34
cuacuacuac uactcgagcg taaatagtgg gtgaacac                  38

<210> SEQ ID NO 35
<211> LENGTH: 41
<212> TYPE: DNA
<213> ORGANISM: Artificial sequence
<220> FEATURE:
<223> OTHER INFORMATION: PCR primer

<400> SEQUENCE: 35
caucaucauc auctcgagga attcgtccat tttagtacac c              41

<210> SEQ ID NO 36
<211> LENGTH: 39
<212> TYPE: DNA
<213> ORGANISM: Artificial sequence
<220> FEATURE:
<223> OTHER INFORMATION: PCR primer

<400> SEQUENCE: 36
cuacuacuac uactcgaggc gcgtacattt tattgctta                 39

<210> SEQ ID NO 37
<211> LENGTH: 41
<212> TYPE: DNA
<213> ORGANISM: Artificial sequence
<220> FEATURE:
<223> OTHER INFORMATION: PCR primer

```
<400> SEQUENCE: 37
caucaucauc auctcgagga attctgcagt gaatccaaat g                          41

<210> SEQ ID NO 38
<211> LENGTH: 22
<212> TYPE: DNA
<213> ORGANISM: Artificial sequence
<220> FEATURE:
<223> OTHER INFORMATION: PCR primer

<400> SEQUENCE: 38
caccatggtc atcatcagaa ac                                               22

<210> SEQ ID NO 39
<211> LENGTH: 22
<212> TYPE: DNA
<213> ORGANISM: Artificial sequence
<220> FEATURE:
<223> OTHER INFORMATION: PCR primer

<400> SEQUENCE: 39
tcacgatcca cagttgtgag ac                                               22
```

NUCLEIC ACID SEQUENCES AND METHODS OF USE FOR THE PRODUCTION OF PLANTS WITH MODIFIED POLYUNSATURATED FATTY ACIDS

CROSS-REFERENCE TO RELATED APPLICATIONS

This national stage application is a continuation of International Application PCT/US03/19445, filed Jun. 20, 2003, which is a continuation-in-part of U.S. patent application Ser. No. 10/176,149, filed Jun. 21, 2002, now U.S. Pat. No. 7,067,722, which is a continuation-in-part of U.S. patent application Ser. No. 09/638,508, filed Aug. 11, 2000, now abandoned, which claims the benefit under 35 U.S.C. §119(e) of U.S. Provisional Application Ser. No. 60/172,128, filed Dec. 17, 1999, and U.S. Provisional Application Ser. No. 60/151,224, filed Aug. 26, 1999.

FIELD OF THE INVENTION

The present invention is directed to nucleic acid molecules and nucleic acid constructs, and other agents associated with fatty acid synthesis. Moreover, the present invention is directed to plants incorporating such agents where the plants exhibit altered ratios of saturated and unsaturated fats. In particular, the present invention is directed to plants incorporating such agents where the plants exhibit altered ratios of monounsaturated to polyunsaturated fatty acids.

BACKGROUND

Plant oils are used in a variety of applications. Novel vegetable oil compositions and improved means to obtain oil compositions, from biosynthetic or natural plant sources, are needed. Depending upon the intended oil use, various different fatty acid compositions are desired.

Higher plants appear to synthesize fatty acids via a common metabolic pathway—the fatty acid synthetase (FAS) pathway. In developing seeds, where fatty acids are attached to glycerol backbones, forming triacylglycerides, for storage as a source of energy for further germination, the FAS pathway is located in the plastids. The first committed step is the formation of acetyl-ACP (acyl carrier protein) from acetyl-CoA and ACP catalyzed by the enzyme, acetyl-CoA:ACP transacylase (ATA). Elongation of acetyl-ACP to 16- and 18-carbon fatty acids involves the cyclical action of the following sequence of reactions: condensation with a two-carbon unit from malonyl-ACP to form a β-ketoacyl-ACP (β-ketoacyl-ACP synthase), reduction of the keto-function to an alcohol (β-ketoacyl-ACP reductase), dehydration to form an enoyl-ACP (β-ketoacyl-ACP dehydratase), and finally reduction of the enoyl-ACP to form the elongated saturated acyl-ACP (enoyl-ACP reductase). β-ketoacyl-ACP synthase I catalyzes elongation from C4:0 up to palmitoyl-ACP (C16:0), whereas β-ketoacyl-ACP synthase II catalyzes the final elongation to stearoyl-ACP (C18:0). Common plant unsaturated fatty acids, such as oleic, linoleic and linolenic acids found in storage triacylglycerides, originate from the desaturation of stearoyl-ACP to form oleoyl-ACP (C18:1) in a reaction catalyzed by a soluble plastid Δ-9 desaturase (also often referred to as "stearoyl-ACP desaturase"). Molecular oxygen is required for desaturation in which reduced ferredoxin serves as an electron co-donor. Additional desaturation is effected sequentially by the actions of membrane bound Δ-12 desaturase and Δ-15 desaturase. These "desaturases" thus create polyunsaturated fatty acids.

Obtaining nucleic acid sequences capable of producing a phenotypic result in FAS, desaturation and/or incorporation of fatty acids into a glycerol backbone to produce an oil is subject to various obstacles including but not limited to the identification of metabolic factors of interest, choice and characterization of an enzyme source with useful kinetic properties, purification of the protein of interest to a level which will allow for its amino acid sequencing, utilizing amino acid sequence data to obtain a nucleic acid sequence capable to use as a probe to retrieve the desired DNA sequence, and the preparation of constructs, transformation and analysis of the resulting plants.

Thus, additional nucleic acid targets and methods for modifying fatty acid compositions are needed. In particular, constructs and methods to produce a range of different fatty acid compositions are needed.

SUMMARY OF THE INVENTION

The present invention provides a substantially purified nucleic acid molecule comprising a nucleic acid sequence with at least 70% sequence identity to a nucleic acid sequence selected from the group consisting of SEQ ID NO:12, SEQ ID NO: 13, SEQ ID NO: 14, SEQ ID NO: 4, complements thereof, and fragments of either.

Further provided by the present invention are a nucleic acid molecule comprising at least 15 consecutive nucleotides of a nucleic acid molecule having the sequence of SEQ ID NO:12; a nucleic acid molecule comprising at least 15 consecutive nucleotides of a nucleic acid molecule having the sequence of SEQ ID NO:13; a nucleic acid molecule comprising at least 15 consecutive nucleotides of a nucleic acid molecule having the sequence of SEQ ID NO:14; and a nucleic acid molecule comprising at least 15 consecutive nucleotides of a nucleic acid molecule having the sequence of SEQ ID NO:4.

Also provided by the present invention is a recombinant nucleic acid molecule comprising as operably linked components: (A) a promoter that functions in a plant cell to cause production of an mRNA molecule; and (B) a nucleic acid sequence that hybridizes under high stringency conditions to a nucleic acid sequence selected from the group consisting of SEQ ID NO:12, SEQ ID NO: 13, SEQ ID NO: 14, SEQ ID NO: 4, complements thereof, and fragments of either.

Further provided by the present invention is a transformed soybean plant having a nucleic acid molecule that comprises (a) a first promoter operably linked to a first nucleic acid molecule having a first nucleic acid sequence that has 85% or greater identity to a nucleic acid sequence selected from the group consisting of SEQ ID NO:1 through SEQ ID NO:2, complements thereof, and fragments of either, and (b) a second nucleic acid molecule having a second nucleic acid sequence that has 85% or greater identity to a nucleic acid sequence selected from the group consisting of SEQ ID NOs:4 through SEQ ID NO:14, complements thereof, and fragments of either, wherein the second nucleic acid molecule is operably linked to the first promoter in a polycistronic configuration or to a second promoter.

Further provided by the present invention is a transformed soybean plant comprising a double-strand RNAi construct where a first promoter is operably linked to a first nucleic acid molecule, having a first nucleic acid sequence that has 85% or greater identity to a nucleic acid sequence selected from the group consisting of SEQ ID NO:1 through SEQ ID NO:2, complements thereof, and fragments of either, wherein a second nucleic acid molecule having a second nucleic acid sequence that has 85% or greater identity to a nucleic acid sequence selected from the group consisting of SEQ ID NO:4 through SEQ ID NO:14, complements thereof, and fragments of either, is operably linked to the first nucleic acid molecule.

Also provided by the present invention is a transformed soybean plant comprising a double-strand RNAi construct where a first promoter is operably linked to a first nucleic acid molecule, having a first nucleic acid sequence that has 85% or greater identity to a nucleic acid sequence selected from the group consisting of SEQ ID NO:1 through SEQ ID NO:2, complements thereof, and fragments of either, wherein a second nucleic acid molecule having a second nucleic acid sequence that has 85% or greater identity to a nucleic acid sequence selected from the group consisting of SEQ ID NO:4 through SEQ ID NO:14, complements thereof, and fragments of either is operably linked to a second promoter in a dsRNAi configuration.

Also provided by the present invention is a transformed soybean plant having two or more nucleic acid molecules wherein each nucleic acid molecule is operably linked to a promoter and wherein each nucleic acid molecule has a nucleic acid sequence that has 85% or greater identity to a nucleic acid sequence selected from the group consisting of SEQ ID NOs:1, 2, 4-14, complements thereof, and fragments of either.

The present invention provides a transformed soybean plant, wherein the level of a transcript encoded by a gene selected from the group consisting of FAD2-1A, FAD2-1B, FAD2-2B, FAD3-1A, FAD3-1B, FAD3-1C is selectively reduced while leaving the level of a transcript encoded by a different gene selected from the group consisting of FAD2-1A, FAD2-1B, FAD2-2B, FAD3-1A, FAD3-1B, FAD3-1C at least partially unaffected.

The present invention also provides a method of producing a soybean plant having a seed with reduced linolenic acid content comprising: transforming a soybean plant with a nucleic acid molecule that comprises (a) a first promoter operably linked to a first nucleic acid molecule having a first nucleic acid sequence that has 85% or greater identity to a nucleic acid sequence selected from the group consisting of SEQ ID NO:1 through SEQ ID NO:2, complements thereof, and fragments of either, and (b) a second nucleic acid molecule having a second nucleic acid sequence that has 85% or greater identity to a nucleic acid sequence selected from the group consisting of SEQ ID NO:4 through SEQ ID NO:14, complements thereof, and fragments of either, wherein the second nucleic acid molecule is operably linked to the first promoter or a second promoter; and growing said plant, wherein said plant produces seed with less linolenic acid than a plant having a similar genetic background but lacking said nucleic acid molecule.

The present invention also provides a method of producing a soybean plant having a seed with increased oleic acid content comprising: transforming a soybean plant with a nucleic acid molecule that comprises (a) a promoter operably linked to a first nucleic acid molecule having a first nucleic acid sequence that has 85% or greater identity to a nucleic acid sequence selected from the group consisting of SEQ ID NO:1 through SEQ ID NO:2, complements thereof, acid fragments of either, and (b) a second nucleic acid molecule having a second nucleic acid sequence that has 85% or greater identity to a nucleic acid sequence selected from the group consisting of SEQ ID NO:4 through SEQ ID NO:14, complements thereof, and fragments of either, wherein the second nucleic acid molecule is operably linked to the first promoter or a second promoter; and growing said plant, wherein said plant produces seed with more oleic acid than a plant having a similar genetic background but lacking said nucleic acid molecule.

The present invention also provides a method of producing a plant having a seed with a modified oil composition comprising: transforming a plant with a nucleic acid molecule that comprises, as operably linked components, a first promoter and a first nucleic acid molecule having a first nucleic acid sequence that has 85% or greater identity to a nucleic acid sequence selected from the group consisting of SEQ ID NO: 1, 2, 4 through 14, complements thereof, and fragments of either; and, growing said plant, wherein said plant produces seed with a modified oil composition compared to a plant having a similar genetic background but lacking said nucleic acid molecule.

The present invention further provides a method of producing a plant having a seed with an altered ratio of monounsaturated to polyunsaturated fatty acids comprising: transforming a plant with a construct that comprises, as operably linked components, two or more nucleic acid molecules, each having a nucleic acid sequence that has 85% or greater identity to a nucleic acid sequence selected from the group consisting of SEQ ID NO: 1, 2, 4 through 14, complements thereof, and fragments of either, wherein each nucleic acid molecule is operably linked to a promoter; and, growing said plant, wherein said plant produces seed with an altered ratio of monounsaturated to polyunsaturated fatty acids compared to a plant having a similar genetic background but lacking said two or more nucleic acid molecules.

DETAILED DESCRIPTION OF THE INVENTION

Figure 1:
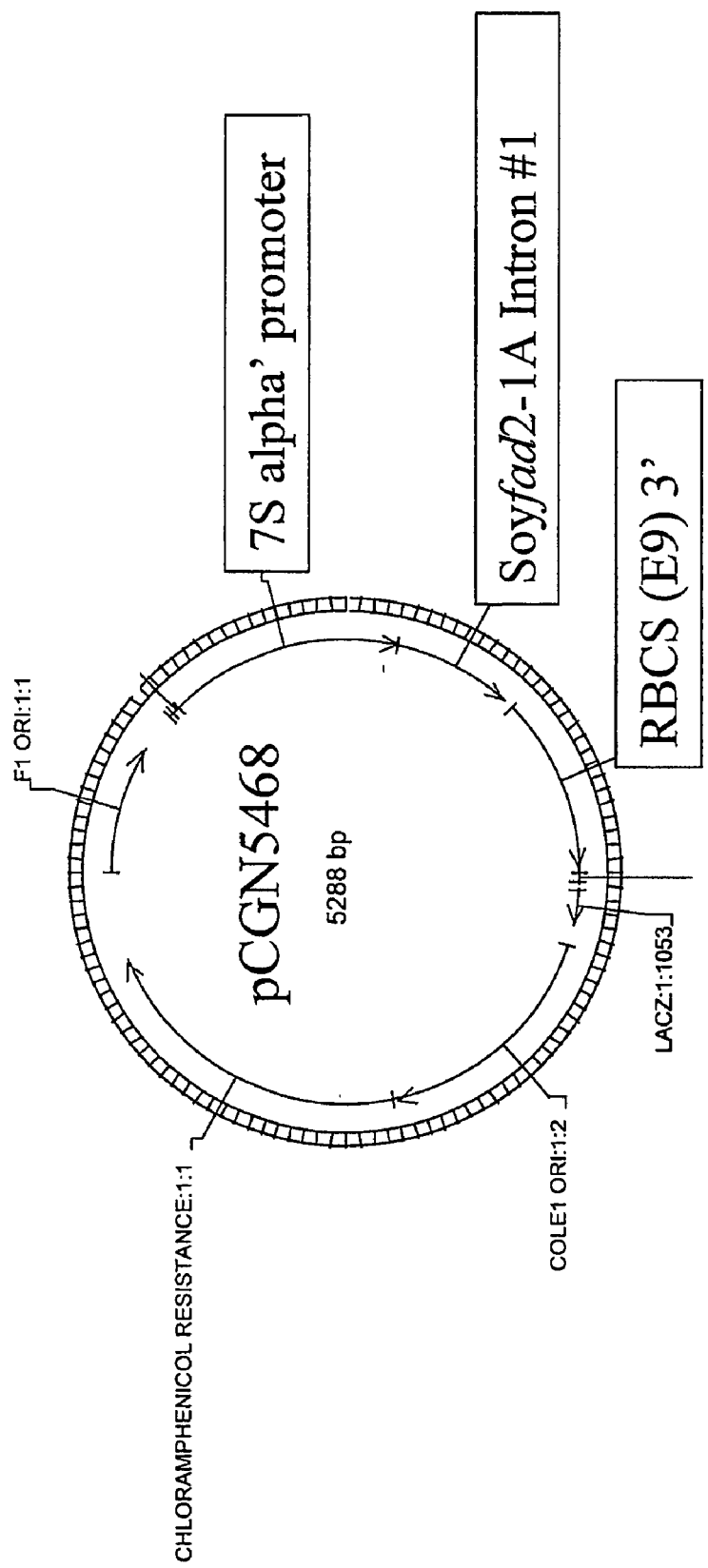
FIG. 1 is a schematic of construct pCGN5468.

Description of the Nucleic Acid Sequences
SEQ ID NO:1 sets forth a nucleic acid sequence of a FAD2-1A intron 1.
SEQ ID NO:2 sets forth a nucleic acid sequence of a FAD2-1B intron 1.
SEQ ID NO:3 sets forth a nucleic acid sequence of a partial FAD2-2 genomic clone.
SEQ ID NO:4 sets forth a nucleic acid sequence of a FAD2-2B intron 1.
SEQ ID NO:5 sets forth a nucleic acid sequence of a FAD3-1A intron 1.
SEQ ID NO:6 sets forth a nucleic acid sequence of a FAD3-1A intron 2.
SEQ ID NO:7 sets forth a nucleic acid sequence of a FAD3-1A intron 3A.
SEQ ID NO:8 sets forth a nucleic acid sequence of a FAD3-1A intron 4.
SEQ ID NO:9 sets forth a nucleic acid sequence of a FAD3-1A intron 5.
SEQ ID NO:10 sets forth a nucleic acid sequence of a FAD3-1A intron 3B.

SEQ ID NO:11 sets forth a nucleic acid sequence of a FAD3-1A intron 3C.

SEQ ID NO:12 sets forth a nucleic acid sequence of a FAD3-1B intron 3C.

SEQ ID NO:13 sets forth a nucleic acid sequence of a FAD3-1B intron 4.

SEQ ID NO:14 sets forth a nucleic acid sequence of a FAD3-1C intron 4.

SEQ ID NO:15 sets forth a cDNA sequence of a FAD2-1A gene sequence.

SEQ ID NOs:16 and 17 set forth nucleic acid sequences of FAD2-1A PCR primers.

SEQ ID NO:18 sets forth a nucleic acid sequence of a partial FAD2-1A genomic clone.

SEQ ID NO:19 sets forth a nucleic acid sequence of a partial FAD2-1B genomic clone.

SEQ ID NOs:20 and 21 set forth nucleic acid sequences of FAD3-1A PCR primers.

SEQ ID NO:22 sets forth a nucleic acid sequence of a FAD2-1B promoter.

SEQ ID NO:23 sets forth a nucleic acid sequence of a partial FAD3-1A genomic clone.

SEQ ID NOs:24 through 39 set forth nucleic acid sequences of PCR primers.

Definitions

As used herein, the term "gene" is used to refer to the nucleic acid sequence that encompasses the 5' untranslated region, including promoter region, associated with the expression of the gene product, any intron and exon regions and 5' or 3' untranslated regions associated with the expression of the gene product.

As used herein, a "FAD2", "Δ12 desaturase" or "omega-6 desaturase" gene is a gene that encodes an enzyme capable of catalyzing the insertion of a double bond into a fatty acyl moiety at the twelfth position counted from the carboxyl terminus.

When referring to proteins and nucleic acids herein, the use of plain capitals, e.g., "FAD2", indicates a reference to an enzyme, protein, polypeptide, or peptide, and the use of italicized capitals, e.g., "FAD2", indicates a reference to nucleic acids, including without limitation genes, cDNAs, and mRNAs.

As used herein the terminology "FAD2-1" is used to refer to a FAD2 gene that is naturally expressed in a specific manner in seed tissue.

As used herein the terminology "FAD2-2" is used to refer a FAD2 gene that is (a) a different gene from a FAD2-1 gene and (b) is naturally expressed in multiple tissues, including the seed.

As used herein, a "FAD3", "Δ15 desaturase" or "omega-3 desaturase" gene is a gene that encodes an enzyme capable of catalyzing the insertion of a double bond into a fatty acyl moiety at the fifteenth position counted from the carboxyl terminus.

As used herein the terminology "FAD3-1" is used to refer a FAD3 gene that is naturally expressed in multiple tissues, including the seed.

As used herein the capital letter that follows the gene terminology (A, B, C) is used to designate the family member, i.e. FAD2-1A is a different gene family member from FAD2-1B.

As used herein, a "mid-oleic soybean seed" is a seed having between 50% and 75% oleic acid present in the oil composition of the seed.

As used herein, a "high oleic soybean seed" is a seed with oil having greater than 75% oleic acid present in the oil composition of the seed.

The term "non-coding" refers to sequences of nucleic acid molecules that do not encode part or all of an expressed protein. Non-coding sequences include but are not limited to introns, promoter regions, 3' untranslated regions, and 5' untranslated regions.

The term "intron" as used herein refers to the normal sense of the term as meaning a segment of nucleic acid molecules, usually DNA, that does not encode part of or all of an expressed protein, and which, in endogenous conditions, is transcribed into RNA molecules, but which is spliced out of the endogenous RNA before the RNA is translated into a protein.

The term "exon" as used herein refers to the normal sense of the term as meaning a segment of nucleic acid molecules, usually DNA, that encodes part of or all of an expressed protein.

As used herein, a promoter that is "operably linked" to one or more nucleic acid sequences is capable of driving expression of one or more nucleic acid sequences, including multiple coding or non-coding nucleic acid sequences arranged in a polycistronic configuration.

A "polycistronic gene" or "polycistronic mRNA" is any gene or mRNA that contains transcribed nucleic acid sequences which correspond to nucleic acid sequences of more than one gene targeted for expression. It is understood that such polycistronic genes or mRNAs may contain sequences that correspond to introns, 5'UTRs, 3'UTRs, or combinations thereof, and that a recombinant polycistronic gene or mRNA might, for example without limitation, contain sequences that correspond to one or more UTRs from one gene and one or more introns from a second gene.

As used herein, the term complement of a nucleic acid sequence refers to the complement of the sequence along its complete length.

As used herein, any range set forth is inclusive of the end points of the range unless otherwise stated.

Agents

The agents of the invention will preferably be "biologically active" with respect to either a structural attribute, such as the capacity of a nucleic acid molecule to hybridize to another nucleic acid molecule, or the ability of a protein to be bound by an antibody (or to compete with another molecule for such binding). Alternatively, such an attribute may be catalytic and thus involve the capacity of the agent to mediate a chemical reaction or response. The agents will preferably be "substantially purified." The term "substantially purified," as used herein, refers to a molecule separated from substantially all other molecules normally associated with it in its native environmental conditions. More preferably a substantially purified molecule is the predominant species present in a preparation. A substantially purified molecule may be greater than 60% free, greater than 75% free, preferably greater than 90% free, and most preferably greater than 95% free from the other molecules (exclusive of solvent) present in the natural mixture. The term "substantially purified" is not intended to encompass molecules present in their native envirorunental conditions.

The agents of the invention may also be recombinant. As used herein, the term "recombinant" means any agent (e.g., including but limited to DNA, peptide), that is, or results, however indirectly, from human manipulation of a nucleic acid molecule.

It is understood that the agents of the invention may be labeled with reagents that facilitate detection of the agent (e.g., fluorescent labels, Prober et al., *Science* 238:336-340 (1987); Albarella et al., EP 144914; chemical labels, Sheldon et al., U.S. Pat. No. 4,582,789; Albarella et al., U.S. Pat. No. 4,563,417; modified bases, Miyoshi et al., EP 119448).

Nucleic Acid Molecules

Agents of the invention include nucleic acid molecules. In an aspect of the present invention, the nucleic acid molecule comprises a nucleic acid sequence, which when introduced into a cell or organism, is capable of selectively reducing the level of a protein and/or transcript encoded by a FAD2 or FAD3 gene while leaving the level of a protein and/or transcript encoded by a second FAD2 or FAD3 gene partially unaffected. In a preferred aspect of the present invention, the nucleic acid molecule comprises a nucleic acid sequence, which when introduced into a cell or organism, is capable of selectively reducing the level of a protein and/or transcript encoded by a FAD2 or FAD3 gene while leaving the level of a protein and/or transcript encoded by a second FAD2 or FAD3 gene substantially unaffected. In a highly preferred aspect of the present invention, the nucleic acid molecule comprises a nucleic acid sequence, which when introduced into a cell or organism, is capable of selectively reducing the level of a protein and/or transcript encoded by a FAD2 or FAD3 gene while leaving the level of a protein and/or transcript encoded by a second FAD2 or FAD3 gene essentially unaffected.

In a preferred aspect, the capability of a nucleic acid molecule to selectively reduce the level of a gene relative to another gene is carried out by a comparison of levels of mRNA transcripts. In another preferred aspect of the present invention, the nucleic acid molecule of the invention comprises a nucleic acid sequence selected from the group consisting of SEQ ID NOs:1 through 15, 18, 19, 22, 23, complements thereof, and fragments of either. In another preferred aspect of the present invention the nucleic acid molecule of the invention comprises a nucleic acid sequence selected from the group consisting of SEQ ID NOs:16, 17, 20, 21, 24 through 39, complements thereof, and fragments of either.

In one aspect of the present invention the nucleic acids of the present invention are said to be introduced nucleic acid molecules. A nucleic acid molecule is said to be "introduced" if it is inserted into a cell or organism as a result of human manipulation, no matter how indirect. Examples of introduced nucleic acid molecules include, but are not limited to, nucleic acids that have been introduced into cells via transformation, transfection, injection, and projection, and those that have been introduced into an organism via methods including, but not limited to, conjugation, endocytosis, and phagocytosis. The cell or organism can be, or can be derived from, a plant, plant cell, algae cell, algae, fungal cell, fungus, or bacterial cell.

As used herein, "essentially unaffected" refers to a level of an agent such as a protein or mRNA transcript that is either not altered by a particular event or altered only to an extent that does not affect the physiological function of that agent. In a preferred aspect, the level of the agent that is essentially unaffected is within 20%, more preferably within 10%, and even more preferably within 5% of the level at which it is found in a cell or organism that lacks a nucleic acid molecule capable of selectively reducing another agent.

As used herein, "substantially unaffected" refers to a level of an agent such as a protein or mRNA transcript in which the level of the agent that is substantially unaffected is within 49%, more preferably within 35%, and even more preferably within 24% of the level at which it is found in a cell or organism that lacks a nucleic acid molecule capable of selectively reducing another agent.

As used herein, "partially unaffected" refers to a level of an agent such as a protein or mRNA transcript in which the level of the agent that is partially unaffected is within 80%, more preferably within 65%, and even more preferably within 50% of the level at which it is found in a cell or organism that lacks a nucleic acid molecule capable of selectively reducing another agent.

As used herein, "a selective reduction" of an agent such as a protein or mRNA is relative to a cell or organism lacking a nucleic acid molecule capable of selectively reducing the agent. In a preferred aspect, the level of the agent is selectively reduced by at least 50%, preferably at least more than 75%, and even more preferably by at least more than 90% or 95%.

When levels of an agent are compared, such a comparison is preferably carried out between organisms with a similar genetic background. In a preferred aspect, a similar genetic background is a background where the organisms being compared share 50% or greater of their nuclear genetic material. In a more preferred aspect a similar genetic background is a background where the organisms being compared share 75% or greater, even more preferably 90% or greater of their nuclear genetic material. In another even more preferable aspect, a similar genetic background is a background where the organisms being compared are plants, and the plants are isogenic except for any genetic material originally introduced using plant transformation techniques.

In an embodiment of the present invention, a nucleic acid molecule, when introduced into a cell or organism, is capable of selectively reducing the level of a protein and/or transcript encoded by a FAD2 gene while leaving the level of a protein and/or transcript encoded by a second FAD2 gene partially unaffected, substantially unaffected, or essentially unaffected. In a preferred aspect, the capability of a nucleic acid molecule to selectively reduce the level of a gene relative to another gene is carried out by a comparison of levels of mRNA transcripts. As used herein, mRNA transcripts include processed and non-processed mRNA transcripts.

In another embodiment, a nucleic acid molecule, when introduced into a cell or organism, is capable of selectively reducing the level of a protein and/or transcript encoded by a FAD2-1 gene while leaving the level of a protein and/or transcript encoded by a FAD2-2 gene partially unaffected, substantially unaffected, or essentially unaffected. In a different embodiment, a nucleic acid molecule, when introduced into a cell or organism, is capable of selectively reducing the level of a protein and/or transcript encoded by a FAD2-2 gene while leaving the level of a protein and/or transcript encoded by a FAD2-1 gene partially unaffected, substantially unaffected, or essentially unaffected.

In a further embodiment, a nucleic acid molecule, when introduced into a cell or organism, is capable of selectively reducing the level of a protein and/or transcript encoded by a FAD2 gene while leaving the level of a protein and/or transcript encoded by a FAD3 gene partially unaffected, substantially unaffected, or essentially unaffected. In a preferred embodiment, a nucleic acid molecule, when introduced into a cell or organism, is capable of selectively reducing the level of a protein and/or transcript encoded by a FAD2-1 gene while leaving the level of a protein and/or transcript encoded by a FAD3 gene partially unaffected, substantially unaffected, or essentially unaffected.

In a different embodiment, a nucleic acid molecule, when introduced into a cell or organism, is capable of selectively reducing the level of a protein and/or transcript encoded by a FAD3 gene while leaving the level of a protein and/or transcript encoded by another FAD3 gene partially unaffected, substantially unaffected, or essentially unaffected.

In an additional embodiment, a nucleic acid molecule, when introduced into a cell or organism, is capable of selectively reducing the level of a protein and/or transcript encoded by a FAD3-1C gene while leaving the level of a protein and/or transcript encoded by a FAD3-1B gene partially unaffected, substantially unaffected, or essentially unaffected. In an additional embodiment, a nucleic acid molecule, when introduced into a cell or organism, is capable of selectively reducing the level of a protein and/or transcript encoded by a FAD3-1C gene while leaving the level of a protein and/or transcript encoded by a FAD3-1A gene partially unaffected, substantially unaffected, or essentially unaffected.

In a different embodiment, a nucleic acid molecule, when introduced into a cell or organism, is capable of selectively reducing the level of a protein and/or transcript encoded by a FAD3-1B gene while leaving the level of a protein and/or transcript encoded by a FAD3-1C gene partially unaffected, substantially unaffected, or essentially unaffected. In a different embodiment, a nucleic acid molecule, when introduced into a cell or organism, is capable of selectively reducing the level of a protein and/or transcript encoded by a FAD3-1B gene while leaving the level of a protein and/or transcript encoded by a FAD3-1A gene partially unaffected, substantially unaffected, or essentially unaffected.

In a further embodiment, a nucleic acid molecule, when introduced into a cell or organism, is capable of selectively reducing the level of a protein and/or transcript encoded by a FAD3-1A gene while leaving the level of a protein and/or transcript encoded by a FAD3-1B gene partially unaffected, substantially unaffected, or essentially unaffected. In an additional embodiment, a nucleic acid molecule, when introduced into a cell or organism, is capable of selectively reducing the level of a protein and/or transcript encoded by a FAD3-1A gene while leaving the level of a protein and/or transcript encoded by a FAD3-1C gene partially unaffected, substantially unaffected, or essentially unaffected.

Further preferred embodiments of the invention are nucleic acid molecules that are at least 50%, 60%, or 70% identical over their entire length to a nucleic acid molecule of the invention, and nucleic acid molecules that are complementary to such nucleic acid molecules. More preferable are nucleic acid molecules that comprise a region that is at least 80% or 85% identical over its entire length to a nucleic acid molecule of the invention and nucleic acid molecules that are complementary thereto. In this regard, nucleic acid molecules at least 90% identical over their entire length are particularly preferred, those at least 95% identical are especially preferred. Further, those with at least 97% identity are highly preferred and those with at least 98% and 99% identity are particularly highly preferred, with those at least 99% being the most highly preferred.

The invention also provides a nucleic acid molecule comprising a nucleic acia molecule sequence obtainable by screening an appropriate library containing the complete gene for a nucleic acid molecule sequence set forth in the Sequence Listing under stringent hybridization conditions with a probe having the sequence of said nucleic acid molecule sequence or a fragment thereof; and isolating said nucleic acid molecule sequence. Fragments useful for obtaining such a nucleic acid molecule include, for example, probes and primers as described herein.

Nucleic acid molecules of the invention can be used as a hybridization probe for RNA, cDNA, or genomic DNA to isolate full length cDNAs or genomic clones and to isolate cDNA or genomic clones of other genes that have a high sequence similarity to the sequence of a nucleic acid molecule set forth in the Sequence Listing.

The nucleic acid molecules of the present invention can be readily obtained by using the herein described nucleic acid molecules or fragments thereof to screen cDNA or genomic libraries obtained from plant species or other appropriate organisms. These methods are known to those of skill in the art, as are methods for forming such libraries. In one embodiment, such sequences are obtained by incubating nucleic acid molecules of the present invention with members of genomic libraries and recovering clones that hybridize to such nucleic acid molecules thereof. In a second embodiment, methods of chromosome walking or inverse PCR may be used to obtain such sequences. In a third embodiment, the sequence of a nucleic acid molecule of the present invention may be used to screen a library or database, using bioinformatics techniques known in the art. See, e.g., *Bioinformatics*, Baxevanis & Ouellette, eds., Wiley-Interscience (1998).

Any of a variety of methods may be used to obtain one or more of the nucleic acid molecules of the present invention. Automated nucleic acid synthesizers may be employed for this purpose, and to make a nucleic acid molecule that has a sequence also found in a cell or organism. In lieu of such synthesis, the disclosed nucleic acid molecules may be used to define a pair of primers that can be used with the polymerase chain reaction to amplify and obtain any desired nucleic acid molecule or fragment.

"Identity," as is well understood in the art, is a relationship between two or more polypeptide sequences or two or more nucleic acid molecule sequences, as determined by comparing the sequences. In the art, "identity" also means the degree of sequence relatedness between polypeptide or nucleic acid molecule sequences, as determined by the match between strings of such sequences. "Identity" can be readily calculated by known methods including, but not limited to, those described in *Computational Molecular Biology*, Lesk, A. M., ed., Oxford University Press, New York (1988); *Biocomputing: Informatics and Genome Projects*, Smith, D. W., ed., Academic Press, New York, 1993; *Computer Analysis of Sequence Data, Part I*, Griffin, A. M. and Griffin, H. G., eds., Humana Press, New Jersey (1994); *Sequence Analysis in Molecular Biology*, von Heinje, G., Academic Press (1987); *Sequence Analysis Primer*, Gribskov, M. and Devereux, J., eds., Stockton Press, New York (1991); and Carillo, H., and Lipman, D., SIAM J. *Applied Math*, 48:1073 (1988). Methods to determine identity are designed to give the largest match between the sequences tested. Moreover, methods to determine identity are codified in publicly available programs. Computer programs which can be used to determine identity between two sequences include, but are not limited to, GCG (Devereux, J., et al., *Nucleic Acids Research* 12(1): 387 (1984); suite of five BLAST programs, three designed for nucleotide sequences queries (BLASTN, BLASTX, and TBLASTX) and two designed for protein sequence queries (BLASTP and TBLASTN) (Coulson, *Trends in Biotechnology*, 12:76-80 (1994); Birren et al., *Genome Analysis*, 1:543-559 (1997)). The BLASTX program is publicly available from NCBI and other sources (*BLAST Manual*, Altschul, S., et al., NCBI NLM NIH, Bethesda, Md. 20894; Altschul, S., et al., *J. Mol. Biol.*, 215:403-410 (1990)). The well-known Smith Waterman algorithm can also be used to determine identity.

Parameters for polypeptide sequence comparison typically include the following:

Algorithm: Needleman and Wunsch, *J. Mol. Biol.*, 48:443-453 (1970)

Comparison matrix: BLOSSUM62 from Hentikoff and Hentikoff, *Proc. Natl. Acad. Sci. USA,* 89:10915-10919 (1992)

Gap Penalty: 12

Gap Length Penalty: 4

A program which can be used with these parameters is publicly available as the "gap" program from Genetics Computer Group, Madison, Wis. The above parameters along with no penalty for end gap are the default parameters for peptide comparisons.

Parameters for nucleic acid molecule sequence comparison include the following:

Algorithm: Needleman and Wunsch, *J. Mol. Bio.,* 48:443-453 (1970)

Comparison matrix: matches—+10; mismatches=0

Gap Penalty: 50

Gap Length Penalty: 3

As used herein, "% identity" is determined using the above parameters as the default parameters for nucleic acid molecule sequence comparisons and the "gap" program from GCG, version 10.2.

The invention further relates to nucleic acid molecules that hybridize to nucleic acid molecules of the present invention. In particular, the invention relates to nucleic acid molecules that hybridize under stringent conditions to the above-described nucleic acid molecules. As used herein, the terms "stringent conditions" and "stringent hybridization conditions" mean that hybridization will generally occur if there is at least 95% and preferably at least 97% identity between the sequences. An example of stringent hybridization conditions is overnight incubation at 42° C. in a solution comprising 50% formamide, 5×SSC (150 mM NaCl, 15 mM trisodium citrate), 50 mM sodium phosphate (pH 7.6), 5× Denhardt's solution, 10% dextran sulfate, and 20 micrograms/milliliter denatured, sheared salmon sperm DNA, followed by washing the hybridization support in 0.1×SSC at approximately 65° C. Other hybridization and wash conditions are well known and are exemplified in Sambrook et al., Molecular Cloning: A Laboratory Manual, Second Edition, Cold Spring Harbor, N.Y. (1989), particularly Chapter 11.

In embodiments where nucleic acid sequences which when expressed are capable of selectively reducing the level of a protein and/or transcript encoded by a FAD2-1 gene and the level of a protein and/or transcript encoded by at least one FAD3 gene while leaving the level of a protein and/or transcript of a FAD2-2 gene in the plant partially, substantially or essentially unaffected, preferred FAD2-1 nucleic acid sequences are selected from the groups consisting of (1) nucleic acid sequences with at least 50%, 60%, 70%, 80%, 90%, 95%, 97%, 98%, 99% or 100% sequence identity over the entire length of the nucleic acid molecule with a nucleotide sequence selected from the group consisting of SEQ ID NO:1, SEQ ID NO:2 and fragments thereof, where such a nucleic acid sequence does not hybridize under stringent conditions to a nucleic acid molecule with a nucleotide sequence of SEQ ID NO:4; (2) nucleic acid molecules which contain sequences that are also found in a soybean FAD2-1 gene intron; and (3) nucleic acid molecules that exhibit sequences with at least 50%, 60%, 70%, 80%, 90%, 95%, 97%, 98%, 99% or 100% sequence identity over the entire length of the nucleic acid molecule with a nucleic acid molecule of (2).

In embodiments where nucleic acid sequences which when expressed are capable of selectively reducing the level of a protein and/or transcript encoded by a FAD2-2 gene and the level of a protein and/or transcript encoded by at least one FAD3 gene while leaving the level of a protein and/or transcript of a FAD2-1 gene in the plant partially, substantially or essentially unaffected, preferred FAD2-2 nucleic acid sequences are selected from the groups consisting of (1) nucleic acid sequences with at least 50%, 60%, 70%, 80%, 90%, 95%, 97%, 98%, 99% or 100% sequence identity over the entire length of the nucleic acid molecule with a nucleotide sequence of SEQ ID NO: 4 and fragments thereof, where such a nucleic acid sequence does not hybridize under stringent conditions to a nucleic acid molecule with a nucleotide sequence selected from the group consisting of SEQ ID NO: 1 and SEQ ID NO: 2; (2) nucleic acid molecules which contain sequences that are also found in a soybean FAD2-2 gene intron; and (3) nucleic acid molecules that exhibit sequences with at least 50%, 60%, 70%, 80%, 90%, 95%, 97%, 98%, 99% or 100% sequence identity over the entire length of the nucleic acid molecule with a nucleic acid molecule of (2).

In embodiments where nucleic acid sequences which when expressed are capable of selectively reducing a FAD3 gene, preferred FAD3 nucleic acid sequences are selected from the groups consisting of (1) nucleic acid sequences with at least 50%, 60%, 70%, 80%, 90%, 95%, 97%, 98%, 99% or 100% sequence identity over the entire length of the nucleic acid molecule with a nucleotide sequence selected from the group consisting of SEQ ID NOs:5-14, and fragments thereof, where such a nucleic acid sequence does not hybridize under stringent conditions to a nucleic acid molecule with a nucleotide sequence selected from the group consisting of SEQ ID NO:1, SEQ ID NO:2, and SEQ ID NO:4; (2) nucleic acid molecules which contain sequences that are also found in a soybean FAD3 gene intron; and (3) nucleic acid molecules that exhibit sequences with at least 50%, 60%, 70%, 80%, 90%, 95%, 97%, 98%, 99% or 100% sequence identity over the entire length of the nucleic acid molecule with a nucleic acid molecule of (2).

One subset of the nucleic acid molecules of the invention includes fragment nucleic acid molecules. Fragment nucleic acid molecules may consist of significant portion(s) of, or indeed most of, the nucleic acid molecules of the invention, such as those specifically disclosed. Alternatively, the fragments may comprise smaller oligonucleotides (having from about 15 to about 400 contiguous nucleotide residues and more preferably, about 15 to about 30 contiguous nucleotide residues, or about 50 to about 100 contiguous nucleotide residues, or about 100 to about 200 contiguous nucleotide residues, or about 200 to about 400 contiguous nucleotide residues, or about 275 to about 350 contiguous nucleotide residues).

In another aspect, a fragment nucleic acid molecule has a nucleic acid sequence that is at least 15, 25, 50, or 100 contiguous nucleotides of a nucleic acid molecule of the present invention. In a preferred embodiment, the nucleic acid molecule has a nucleic acid sequence that is at least 15, 25, 50, or 100 contiguous nucleotides of a nucleic acid molecule having a nucleic acid sequence selected from the group consisting of SEQ ID NO:1 through SEQ ID NO:14 and complements thereof.

A fragment of one or more of the nucleic acid molecules of the present invention may be a probe and specifically a PCR probe. A PCR probe is a nucleic acid molecule capable of initiating a polymerase activity while in a double-stranded structure with another nucleic acid molecule. Various methods for determining the structure of PCR probes and PCR techniques exist in the art. Computer generated searches using programs such as Primer3 (www-genome.wi.mit.edu/cgi-bin/primer/primer3.cgi), STSPipeline (www-genome.wi.mit.edu/cgi-bin/www-STS_Pipeline), or GeneUp (Pesole et al., *BioTechniques* 25:112-123 (1998)), for example, can be used to identify potential PCR primers.

Nucleic acid molecules or fragments thereof of the present invention are capable of specifically hybridizing to other nucleic acid molecules under certain circumstances. Nucleic acid molecules of the present invention include those that specifically hybridize to nucleic acid molecules having a nucleic acid sequence selected from the group consisting of SEQ ID NO:1 through SEQ ID NO:14, complements thereof, and fragments of either.

As used herein, two nucleic acid molecules are said to be capable of specifically hybridizing to one another if the two molecules are capable of forming an anti-parallel, double-stranded nucleic acid structure.

A nucleic acid molecule of the invention can also encode a homolog nucleic acid molecule. As used herein, a homolog nucleic acid molecule or fragment thereof is a counterpart nucleic acid molecule or fragment thereof in a second species (e.g., corn FAD2-1 intron nucleic acid molecule is a homolog of *Arabidopsis* FAD2-1 intron nucleic acid molecule). A homolog can also be generated by molecular evolution or DNA shuffling techniques, so that the molecule retains at least one functional or structure characteristic of the original polypeptide (see, for example, U.S. Pat. No. 5,811,238).

In another embodiment, the homolog is obtained from a plant selected from the group consisting of alfalfa, *Arabidopsis*, barley, *Brassica campestris*, oilseed rape, broccoli, cabbage, canola, citrus, cotton, garlic, oat, *Allium*, flax, an ornamental plant, jojoba, corn, peanut, pepper, potato, rapeseed, rice, rye, sorghum, strawberry, sugarcane, sugarbeet, tomato, wheat, poplar, pine, fir, eucalyptus, apple, lettuce, lentils, grape, banana, tea, turf grasses, sunflower, *Phaseolus*, crambe, mustard, castor bean, sesame, cottonseed, linseed, safflower, and oil palm. More particularly, a preferred homolog is obtained from a plant selected from the group consisting of canola, corn, *Brassica campestris*, oilseed rape, soybean, crambe, mustard, castor bean, peanut, sesame, cottonseed, linseed, rapeseed, safflower, oil palm, flax, and sunflower. In an even more preferred embodiment, the homolog is obtained from a plant selected from the group consisting of canola, rapeseed, corn, *Brassica campestris*, oilseed rape, soybean, sunflower, safflower, oil palm, and peanut.

Plant Constructs and Plant Transformants

One or more of the nucleic acid molecules of the invention may be used in plant transformation or transfection. Exogenous genetic material may be transferred into a plant cell and the plant cell regenerated into a whole, fertile or sterile plant or plant part. Exogenous genetic material is any genetic material, whether naturally occurring or otherwise, from any source that is capable of being inserted into any organism.

A plant can have a family of more than one FAD2 or FAD3 genes (i.e., genes which encode an enzyme with the specified activity present at different locations within the genome of the plants). As used herein, a "FAD2 gene family member" is any FAD2 gene found within the genetic material of the plant. As used herein, a "FAD3 gene family member" is any FAD3 gene found within the genetic material of the plant. In one embodiment, a gene family can be additionally classified by the similarity of the nucleic acid sequences. In a preferred aspect of this embodiment, a gene family member exhibits at least 60%, more preferably at least 70%, more preferably at least 80% nucleic acid sequence identity in the coding sequence portion of the gene.

In one aspect of the present invention, a plant contains a double-stranded RNAi construct where a first promoter is operably linked to a first nucleic acid molecule, having a first nucleic acid sequence that has at least about 85% identity to a nucleic acid sequence selected from the group consisting of SEQ ID NO:1 through SEQ ID NO:2, complements thereof, and fragments of either, and a second nucleic acid molecule that has a second nucleic acid sequence with at least about 85% identity to a nucleic acid sequence selected from the group consisting of SEQ ID NO:4 through SEQ ID NO:14, complements thereof, and fragments of either, is operably linked to the first nucleic acid molecule.

Also provided by the present invention is a plant comprising a double-stranded RNAi construct where a first promoter is operably linked to a first nucleic acid molecule, having a first nucleic acid sequence that has at least about 85% identity to a nucleic acid sequence selected from the group consisting of SEQ ID NO:1 through SEQ ID NO:2, complements thereof, and fragments of either, wherein a second nucleic acid molecule having a second nucleic acid sequence that has at least about 85% identity to a nucleic acid sequence selected from the group consisting of SEQ ID NO:4 through SEQ ID NO:14, complements thereof, and fragments of either is operably linked to a second promoter in a dsRNAi configuration.

In one embodiment of the invention, the expression level of a protein or transcript in one family member of that gene is selectively reduced while leaving the level of a protein or transcript of a second family member partially unaffected. In a preferred embodiment of the invention, the expression level of a protein or transcript in one family member of that gene is selectively reduced while leaving the level of a protein or transcript of a second family member substantially unaffected. In a highly preferred embodiment of the invention, the expression level of a protein or transcript in one family member of that gene is selectively reduced while leaving the level of a protein or transcript of a second family member essentially unaffected.

In a particularly preferred embodiment, a plant of the present invention includes nucleic acid sequences which when expressed are capable of selectively reducing the expression level of a protein and/or transcript encoded by certain FAD2 and FAD3 genes while leaving the level of a protein and/or transcript of at least one other FAD2 or FAD3 gene in the plant partially unaffected. In a particularly preferred embodiment, a plant of the present invention includes nucleic acid sequences which when expressed are capable of selectively reducing the expression level of a protein and/or transcript encoded by certain FAD2 and FAD3 genes while leaving the level of a protein and/or transcript of at least one other FAD2 or FAD3 gene in the plant substantially unaffected. In a particularly preferred embodiment, a plant of the present invention includes nucleic acid sequences which when expressed are capable of selectively reducing the expression level of a protein and/or transcript encoded by certain FAD2 and FAD3 genes while leaving the level of a protein and/or transcript of at least one other FAD2 or FAD3 gene in the plant essentially unaffected.

In a more particularly preferred embodiment, a soybean plant of the present invention includes nucleic acid sequences which when expressed are capable of selectively reducing the expression level of a protein and/or transcript encoded by a FAD2-1 gene and at least one FAD3 gene while leaving the level of a protein and/or transcript of a FAD2-2 gene in the plant partially unaffected. In a more particularly preferred embodiment, a soybean plant of the present invention includes nucleic acid sequences which when expressed are capable of selectively reducing the expression level of a protein and/or transcript encoded by a FAD2-1 gene and at least one FAD3 gene while leaving the level of a protein and/or transcript of a FAD2-2 gene in the plant substantially unaffected. In a more particularly preferred embodiment, a soybean plant of the present invention includes nucleic acid sequences which when expressed are capable of selectively reducing the expression level of a protein and/or transcript encoded by a FAD2-1 gene and at least one FAD3 gene while leaving the level of a protein and/or transcript of a FAD2-2 gene in the plant essentially unaffected.

In another more particularly preferred embodiment, a soybean plant of the present invention includes nucleic acid sequences which when expressed are capable of selectively reducing the expression level of a protein and/or transcript encoded by a FAD2-1 gene and at least two, three or more FAD3 genes while leaving the level of a protein and/or transcript of a FAD2-2 gene in the plant partially unaffected. In another more particularly preferred embodiment, a soybean plant of the present invention includes nucleic acid sequences which when expressed are capable of selectively reducing the expression level of a protein and/or transcript encoded by a FAD2-1 gene and at least two, three or more FAD3 genes while leaving the level of a protein and/or transcript of a FAD2-2 gene in the plant substantially unaffected. In another more particularly preferred embodiment, a soybean plant of the present invention includes nucleic acid sequences which when expressed are capable of selectively reducing the expression level of a protein and/or transcript encoded by a FAD2-1 gene and at least two, three or more FAD3 genes while leaving the level of a protein and/or transcript of a FAD2-2 gene in the plant essentially unaffected.

In a preferred embodiment, a soybean of the present invention includes exogenous nucleic acid sequences selected from the groups consisting of a FAD3 intron or fragment thereof, more preferably from a nucleic acid molecule selected from the group consisting of SEQ ID NOs:5-14, or fragments thereof.

In a particularly preferred embodiment, a soybean of the present invention includes a nucleic acid sequence which when expressed is capable of reducing the expression level of a protein and/or transcript encoded by a FAD3-1C gene while leaving the level of a protein and/or transcript of a FAD3-1B gene in the plant partially unaffected. In a particularly preferred embodiment, a soybean of the present invention includes a nucleic acid sequence which when expressed is capable of reducing the expression level of a protein and/or transcript encoded by a FAD3-1C gene while leaving the level of a protein and/or transcript of a FAD3-1B gene in the plant substantially unaffected. In a particularly preferred embodiment, a soybean of the present invention includes a nucleic acid sequence which when expressed is capable of reducing the expression level of a protein and/or transcript encoded by a FAD3-1C gene while leaving the level of a protein and/or transcript of a FAD3-1B gene in the plant essentially unaffected.

In embodiments where nucleic acid sequences which when expressed are capable of selectively reducing the expression level of a protein and/or transcript encoded by a FAD2-1 gene and at least one FAD3 genes while leaving the level of a protein and/or transcript of a FAD2-2 gene in the plant partially unaffected, substantially unaffected, or essentially unaffected, preferred FAD2-1 nucleic acid sequences are selected from the groups consisting of (1) nucleic acid sequences with at least 50%, 60%, 70%, 80%, 90%, 95%, 97%, 98%, 99% or 100% sequence identity over the entire length of the nucleic acid molecule with a nucleotide sequence selected from the group consisting of SEQ ID NO:1, SEQ ID NO:2 and fragments thereof, where such a nucleic acid sequence does not hybridize under stringent conditions to a nucleic acid molecule with a nucleotide sequence of SEQ ID NO:4; (2) nucleic acid molecules which contain sequences that are also found in a soybean FAD2-1 gene intron; and (3) nucleic acid molecules that exhibit sequences with at least 50%, 60%, 70%, 80%, 90%, 95%, 97%, 98%, 99% or 100% sequence identity over the entire length of the nucleic acid molecule with a nucleic acid molecule of (2).

In embodiments where nucleic acid sequences which when expressed are capable of selectively reducing the expression level of a protein and/or transcript encoded by a FAD3 gene, preferred FAD3 nucleic acid sequences are selected from the groups consisting of (1) nucleic acid sequences with at least 50%, 60%, 70%, 80%, 90%, 95%, 97%, 98%, 99% or 100% sequence identity over the entire length of the nucleic acid molecule with a nucleotide sequence selected from the group consisting of SEQ ID NOs:5-14, and fragments thereof, where such a nucleic acid sequence does not hybridize under stringent conditions to a nucleic acid molecule with a nucleotide sequence selected from the group consisting of SEQ ID NO:1, SEQ ID NO:2, and SEQ ID NO:4; (2) nucleic acid molecules which contain sequences that are also found in a soybean FAD3 gene intron; and (3) nucleic acid molecules that exhibit sequences with at least 50%, 60%, 70%, 80%, 90%, 95%, 97%, 98%, 99% or 100% sequence identity over the entire length of the nucleic acid molecule with a nucleic acid molecule of (2).

In a preferred embodiment, a soybean seed of the present invention has an oil composition that is 50% or greater oleic acid and 10% or less linolenic acid. In a more preferred embodiment, a soybean seed of the present invention has an oil composition that is 60% or greater oleic acid and 7% or less linolenic acid. In a particular preferred embodiment, a soybean seed of the present invention has an oil composition that is 65% or greater oleic acid and 5% or less linolenic acid, preferably 4% or less linolenic acid, and more preferably 3% or less linolenic acid. As used herein, all % composition of oils within a plant or plant part such as a seed are determined by relative mole percent.

In another preferred embodiment a soybean seed of the present invention has an oil composition that is between 50% and 90% oleic acid, and 10% or less linolenic acid. In a more preferred embodiment, a soybean seed of the present invention has an oil composition that is between 60% and 80% oleic acid, and 7% or less linolenic acid. In a particular preferred embodiment, a soybean seed of the present invention has an oil composition that is between 65% and 75% oleic acid, and 5% or less linolenic acid, preferably 4% or less linolenic acid, and more preferably 3% or less linolenic acid.

In another preferred embodiment a soybean seed of the present invention has an oil composition that is between 50% and 90% oleic acid, between 8% and 16% palmitic acid and 10% or less linolenic acid. In a more preferred embodiment, a soybean seed of the present invention has an oil composition that is between 60% and 80% oleic acid, between 6% and 12% palmitic acid and 7% or less linolenic acid. In a particularly preferred embodiment, a soybean seed of the present invention has an oil composition that is between 65% and 75% oleic acid, between 8% and 11% palmitic acid and 5% or less linolenic acid, preferably 4% or less linolenic acid, and more preferably 3% or less linolenic acid.

In a particularly preferred embodiment, a soybean seed of the present invention has an oil composition that is between 65% and 75% oleic acid, and 5% or less linolenic acid, preferably 4% or less linolenic acid, and more preferably 3% or less linolenic acid, where nucleic acid sequences which when expressed are capable of selectively reducing the expression level of a protein and/or transcript encoded by a FAD2-1 gene and at least one FAD3 gene while leaving the level of a protein and/or transcript of a FAD2-2 gene in the plant partially unaffected, substantially unaffected, or essentially unaffected, the FAD2-1 nucleic acid sequences are selected from the groups consisting of: (1) nucleic acid sequences with at least 50%, 60%, 70%, 80%, 90%, 95%, 97%, 98%, 99% or 100% sequence identity over the entire length of the nucleic acid molecule with a nucleotide sequence selected from the group consisting of SEQ ID NO:1, SEQ ID NO:2 and fragments thereof, where such a nucleic acid sequence does not hybridize under stringent conditions to a nucleic acid molecule with a nucleotide sequence of SEQ ID NO:4; (2) nucleic acid molecules which contain sequences that are also found in a soybean FAD2-1 gene intron; and (3) nucleic acid molecules that exhibit sequences with at least 50%, 60%, 70%, 80%, 90%, 95%, 97%, 98%, 99% or 100% sequence identity over the entire length of the nucleic acid molecule with a nucleic acid molecule of (2); and the FAD3 nucleic acid sequences are selected from the groups consisting of (1) nucleic acid sequences with at least 50%, 60%, 70%, 80%, 90%, 95%, 97%, 98%, 99% or 100% sequence identity over the entire length of the nucleic acid molecule with a nucleotide sequence selected from the group consisting of SEQ ID NOs:5-14, and fragments thereof, where such a nucleic acid sequence does not hybridize under stringent conditions to a nucleic acid molecule with a nucleotide sequence selected from the group consisting of SEQ ID NO:1, SEQ ID NO:2 and SEQ ID NO:4; (2) nucleic acid molecules which contain sequences that are also found in a soybean FAD3 gene intron; and (3) nucleic acid molecules that exhibit sequences with at least 50%, 60%, 70%, 80%, 90%, 95%, 97%, 98%, 99% or 100% sequence identity over the entire length of the nucleic acid molecule with a nucleic acid molecule of (2).

In another embodiment, a soybean seed of the present invention has an oil composition that is 80% or greater, more preferably 90% or greater oleic acid and 5% or less linolenic acid, preferably 4% or less linolenic acid, and more preferably 3% or less linolenic acid.

In a preferred embodiment, a soybean seed of the present invention has an oil composition that is 80% or greater, more preferably 90% or greater oleic acid and 5% or less linolenic acid, preferably 4% or less linolenic acid, and more preferably 3% or less linolenic acid, where the nucleic acid sequences are capable of reducing the expression of FAD2-1, FAD2-2 and at least one FAD3 genes. In a particularly preferred embodiment of this aspect, the nucleic acid sequences are selected from the group consisting of SEQ ID NO:1 through SEQ ID NO:14, complements thereof, and fragments of either.

In a preferred embodiment of the present invention, a soybean seed of the present invention has an oil composition of 50% or greater oleic acid, more preferably 60% or greater, 70% or greater, 80% or greater, or 90% or greater oleic acid.

In another preferred embodiment of the present invention, a soybean seed of the present invention has an oil composition that is 10% or less linolenic acid, more preferably 5% or less, 4% or less, or 3% or less linolenic acid.

Analogous genetic material may also be obtained from other species, for example monocotyledons or dicotyledons, including, but not limited to canola, corn, soybean, *Arabidopsis, Phaseolus*, peanut, alfalfa, wheat, rice, oat, sorghum, rapeseed, rye, barley, millet, fescue, perennial ryegrass, sugarcane, cranberry, papaya, banana, safflower, oil palm, flax, muskmelon, apple, cucumber, dendrobium, gladiolus, chrysanthemum, liliacea, cotton, eucalyptus, sunflower, *Brassica campestris*, oilseed rape, turfgrass, sugarbeet, coffee and dioscorea (Christou, INO: *Particle Bombardment Genetic Engineering of Plants*, Biotechnology Intelligence Unit. Academic Press, San Diego, Calif. (1996)), with canola, corn, *Brassica campestris*, oilseed rape, rapeseed, soybean, crambe, mustard, castor bean, peanut, sesame, cottonseed, linseed, safflower, oil palm, flax, and sunflower preferred, and canola, rapeseed, corn, *Brassica campestris*, oilseed rape, soybean, sunflower, safflower, oil palms, and peanut more preferred. In a more preferred embodiment, the genetic material is transferred into canola. In another more preferred embodiment, the genetic material is transferred into oilseed rape. In another particularly preferred embodiment, the genetic material is transferred into soybean.

The levels of products such as transcripts or proteins may be increased or decreased throughout an organism such as a plant or localized in one or more specific organs or tissues of the organism. For example the levels of products may be increased or decreased in one or more of the tissues and organs of a plant including without limitation: roots, tubers, stems, leaves, stalks, fruit, berries, nuts, bark, pods, seeds and flowers. A preferred organ is a seed.

Exogenous genetic material may be transferred into a host cell by the use of a DNA vector or construct designed for such a purpose. Design of such a vector is generally within the skill of the art (See, *Plant Molecular Biology: A Laboratory Manual*, Clark (ed.), Springer, N.Y. (1997)).

A construct or vector may include a plant promoter to express the nucleic acid molecule of choice. In a preferred embodiment, any nucleic acid molecules described herein can be operably linked to a promoter region which functions in a plant cell to cause the production of an mRNA molecule. For example, any promoter that functions in a plant cell to cause the production of an mRNA molecule, such as those promoters described herein, without limitation, can be used. In a preferred embodiment, the promoter is a plant promoter.

A number of promoters that are active in plant cells have been described in the literature. These include, but are not limited to, the nopaline synthase (NOS) promoter (Ebert et al., *Proc. Natl. Acad. Sci. (U.S.A.)* 84:5745-5749 (1987)), the octopine synthase (OCS) promoter (which is carried on tumor-inducing plasmids of *Agrobacterium turnefaciens*), the caulimovirus promoters such as the cauliflower mosaic virus (CaMV) 19S promoter (Lawton et al., *Plant Mol. Biol.* 9: 315-324 (1987)) and the CaMV 35S promoter (Odell et al., *Nature* 313:810-812 (1985)), the figwort mosaic virus 35S-promoter (U.S. Pat. No. 5,378,619), the light-inducible promoter from the small subunit of ribulose-1,5-bis-phosphate carboxylase (ssRUBISCO), the Adh promoter (Walker et al., *Proc. Natl. Acad. Sci. (U.S.A.)* 84:6624-6628 (1987)), the sucrose synthase promoter (Yang et al., *Proc. Natl. Acad. Sci. (U.S.A)* 87:4144-4148 (1990)), the R gene complex promoter (Chandler et al., *The Plant Cell* 1:1175-1183 (1989)) and the chlorophyll a/b binding protein gene promoter. These promoters have been used to create DNA constructs that have been expressed in plants; see, e.g., PCT publication WO 84/02913. The CaMV 35S promoters are preferred for use in plants. Promoters known or found to cause transcription of DNA in plant cells can be used in the invention.

Particularly preferred promoters can also be used to express a nucleic acid molecule of the present invention in seeds or fruits. Indeed, in a preferred embodiment, the promoter used is a seed specific promoter. Examples of such promoters include the 5' regulatory regions from such genes as napin (Kridl et al., *Seed Sci. Res.* 1:209:219 (1991)), phaseolin (Bustos, et al., *Plant Cell*, 1(9):839-853 (1989)), soybean trypsin inhibitor (Riggs, et al., *Plant Cell* 1(6):609-621 (1989)), ACP (Baerson, et al., *Plant Mol. Biol.*, 22(2): 255-267 (1993)), stearoyl-ACP desaturase (Slocombe, et al.,

*Plant Physiol.* 104(4):167-176 (1994)), soybean a subunit of b-conglycinin (soy 7s, (Chen et al., *Proc. Natl. Acad. Sci.,* 83:8560-8564 (1986))), and oleosin (see, for example, Hong, et al., *Plant Mol. Biol.,* 34(3):549-555 (1997)). Further examples include the promoter for β-conglycinin (Chen et al., *Dev. Genet.* 10:112-122 (1989)) and the promoter for FAE (PCT Publication WO 01/11061). Preferred promoters for expression in the seed are 7S and napin promoters.

Additional promoters that may be utilized are described, for example, in U.S. Pat. Nos. 5,378,619; 5,391,725; 5,428,147; 5,447,858; 5,608,144; 5,608,144; 5,614,399; 5,633,441; 5,633,435; and 4,633,436. In addition, a tissue specific enhancer may be used (Fromm et al., *The Plant Cell* 1:977-984 (1989)).

Constructs or vectors may also include, with the region of interest, a nucleic acid sequence that acts, in whole or in part, to terminate transcription of that region. A number of such sequences have been isolated, including the Tr7 3' sequence and the NOS 3' sequence (Ingelbrecht et al., *The Plant Cell* 1:671-680 (1989); Bevan et al., *Nucleic Acids Res.* 11:369-385 (1983)). Regulatory transcript termination regions can be provided in plant expression constructs of this invention as well. Transcript termination regions can be provided by the DNA sequence encoding the gene of interest or a convenient transcription termination region derived from a different gene source, for example, the transcript termination region that is naturally associated with the transcript initiation region. The skilled artisan will recognize that any convenient transcript termination region that is capable of terminating transcription in a plant cell can be employed in the constructs of the present invention.

A vector or construct may also include regulatory elements. Examples of such include the Adh intron 1 (Callis et al., *Genes and Develop.* 1:1183-1200 (1987)), the sucrose synthase intron (Vasil et al., *Plant Physiol.* 91:1575-1579 (1989)) and the TMV omega element (Gallie et al., *The Plant Cell* 1:301-311 (1989)). These and other regulatory elements may be included when appropriate.

A vector or construct may also include a selectable marker. Selectable markers may also be used to select for plants or plant cells that contain the exogenous genetic material. Examples of such include, but are not limited to: a neo gene (Potrykus et al., *Mol. Gen. Genet.* 199:183-188 (1985)), which codes for kanamycin resistance and can be selected for using kanamycin, RptII, G418, hpt; a bar gene which codes for bialaphos resistance; a mutant EPSP synthase gene (Hinchee et al., *Bio/Technology* 6:915-922 (1988); Reynaerts et al., Selectable and Screenable Markers. In Gelvin and Schilperoort. Plant Molecular Biology Manual, Kluwer, Dordrecht (1988); Reynaerts et al., Selectable and screenable markers. In Gelvin and Schilperoort. Plant Molecular Biology Manual, Kluwer, Dordrecht (1988)), aadA (Jones et al., *Mol. Gen. Genet.* (1987)),) which encodes glyphosate resistance; a nitrilase gene which confers resistance to bromoxynil (Stalker et al., *J. Biol. Chem.* 263:6310-6314 (1988)); a mutant acetolactate synthase gene (ALS) which confers imidazolinone or sulphonylurea resistance (European Patent Application 154,204 (Sep. 11, 1985)), ALS (D'Halluin et al., Bio/Technology 10:309-314 (1992)), and a methotrexate resistant DHFR gene (Thillet et al., *J. Biol. Chem.* 263:12500-12508 (1988)).

A vector or construct may also include a screenable marker. Screenable markers may be used to monitor expression. Exemplary screenable markers include: a β-glucuronidase or uidA gene (GUS) which encodes an enzyme for which various chromogenic substrates are known (Jefferson, *Plant Mol. Biol, Rep.* 5:387-405 (1987); Jefferson et al., *EMBO J.* 6:3901-3907 (1987)); an R-locus gene, which encodes a product that regulates the production of anthocyanin pigments (red color) in plant tissues (Dellaporta et al., Stadler Symposium 11:263-282 (1988)); a β-lactamase gene (Sutcliffe et al., *Proc. Natl. Acad. Sci. (U.S.A.)* 75:3737-3741 (1978)), a gene which encodes an enzyme for which various chromogenic substrates are known (e.g., PADAC, a chromogenic cephalosporin); a luciferase gene (Ow et al., *Science* 234:856-859 (1986)); a xylE gene (Zukowsky et al., *Proc. Natl. Acad. Sci. (U.S.A)* 80:1101-1105 (1983)) which encodes a catechol dioxygenase that can convert chromogenic catechols; an (α-amylase gene (Ikatu et al., *Bio/Technol.* 8:241-242 (1990)); a tyrosinase gene (Katz et al., *J. Gen. Microbiol.* 129:2703-2714 (1983)) which encodes an enzyme capable of oxidizing tyrosine to DOPA and dopaquinone which in turn condenses to melanin; an α-galactosidase, which will turn a chromogenic (α-galactose substrate.

Included within the terms "selectable or screenable marker genes" are also genes that encode a secretable marker whose secretion can be detected as a means of identifying or selecting for transformed cells. Examples include markers that encode a secretable antigen that can be identified by antibody interaction, or even secretable enzymes that can be detected catalytically. Secretable proteins fall into a number of classes, including small, diffusible proteins that are detectable, (e.g., by ELISA), small active enzymes that are detectable in extracellular solution (e.g., α-amylase, β-lactamase, phosphinothricin transferase), or proteins that are inserted or trapped in the cell wall (such as proteins that include a leader sequence such as that found in the expression unit of extension or tobacco PR-S). Other possible selectable and/or screenable marker genes will be apparent to those of skill in the art.

It is understood that two or more nucleic molecules of the present invention may be introduced into a plant using a single construct and that construct can contain more than one promoter. In embodiments where the construct is designed to express two nucleic acid molecules, it is preferred that the two promoters are (i) two constitutive promoters, (ii) two seed-specific promoters, or (iii) one constitutive promoter and one seed-specific promoter. Preferred seed-specific and constitutive promoters are a napin and a CaMV promoter, respectively. Illustrative combinations are set forth in Example 8. It is understood that two or more of the nucleic molecules may be physically linked and expressed utilizing a single promoter, preferably a seed-specific or constitutive promoter.

It is further understood that two or more nucleic acids of the present invention may be introduced into a plant using two or more different constructs. Alternatively, two or more nucleic acids of the present invention may be introduced into two different plants and the plants may be crossed to generate a single plant expressing two or more nucleic acids. In an RNAi embodiment, it is understood that the sense and antisense strands may be introduced into the same plant on one construct or two constructs. Alternatively, the sense and antisense strands may be introduced into two different plants and the plants may be crossed to generate a single plant expressing both sense and antisense strands.

Any of the nucleic acid molecules and constructs of the invention may be introduced into a plant or plant cell in a permanent or transient manner. Preferred nucleic acid molecules and constructs of the present invention are described above in the Detailed Description, and in the Examples. Another embodiment of the invention is directed to a method of producing transgenic plants which generally comprises the steps of selecting a suitable plant or plant cell, transforming the plant or plant cell with a recombinant vector, and obtaining a transformed host cell.

In a preferred embodiment the plant or cell is, or is derived from, a plant involved in the production of vegetable oils for edible and industrial uses. Especially preferred are temperate oilseed crops. Plants of interest include, but are not limited to, rapeseed (canola and High Erucic Acid varieties), maize, soybean, crambe, mustard, castor bean, peanut, sesame, cotton, linseed, safflower, oil palm, flax, sunflower, and coconut. The invention is applicable to monocotyledonous or dicotyledonous species alike, and will be readily applicable to new and/or improved transformation and regulatory techniques.

Methods and technology for introduction of DNA into plant cells are well known to those of skill in the art, and virtually any method by which nucleic acid molecules may be introduced into a cell is suitable for use in the present invention. Non-limiting examples of suitable methods include: chemical methods; physical methods such as microinjection, electroporation, the gene gun, microprojectile bombardment, and vacuum infiltration; viral vectors; and receptor-mediated mechanisms. Other methods of cell transformation can also be used and include but are not limited to introduction of DNA into plants by direct DNA transfer into pollen, by direct injection of DNA into reproductive organs of a plant, or by direct injection of DNA into the cells of immature embryos followed by the rehydration of desiccated embryos.

*Agrobacterium*-mediated transfer is a widely applicable system for introducing genes into plant cells. See, e.g., Fraley et al., *Bio/Technology* 3:629-635 (1985); Rogers et al., *Methods Enzymol.* 153:253-277 (1987). The region of DNA to be transferred is defined by the border sequences and intervening DNA is usually inserted into the plant genome. Spielmann et al., *Mol. Gen. Genet.* 205:34 (1986). Modem *Agrobacterium* transformation vectors are capable of replication in *E. coli* as well as *Agrobacterium*, allowing for convenient manipulations. Klee et al., In: *Plant DNA Infectious Agents*, Hohn and Schell (eds.), Springer-Verlag, N. Y., pp. 179-203 (1985).

The regeneration, development and cultivation of plants from single plant protoplast transformants or from various transformed explants is well known in the art. See generally, Maliga et al., *Methods in Plant Molecular Biology*, Cold Spring Harbor Press (1995); Weissbach and Weissbach, In: *Methods for Plant Molecular Biology*, Academic Press, San Diego, Calif. (1988). Plants of the present invention can be part of or generated from a breeding program, and may also be reproduced using apomixis. Methods for the production of apomictic plants are known in the art. See, e.g., U.S. Pat. No. 5,811,636.

Cosuppression is the reduction in expression levels, usually at the level of RNA, of a particular endogenous gene or gene family by the expression of a homologous sense construct that is capable of transcribing mRNA of the same strandedness as the transcript of the endogenous gene (Napoli et al., *Plant Cell* 2:279-289 (1990); van der Krol et al., *Plant Cell* 2:291-299 (1990)). Cosuppression may result from stable transformation with a single copy nucleic acid molecule that is homologous to a nucleic acid sequence found with the cell (Prolls and Meyer, *Plant J.* 2:465-475 (1992)) or with multiple copies of a nucleic acid molecule that is homologous to a nucleic acid sequence found with the cell (Mittlesten et al., *Mol. Gen. Genet.* 244:325-330 (1994)). Genes, even though different, linked to homologous promoters may result in the cosuppression of the linked genes (Vaucheret, *C.R. Acad. Sci. III* 316:1471-1483 (1993); Flavell, *Proc. Natl. Acad. Sci. (U.S.A.)* 91:3490-3496 (1994)); van Blokland et al, *Plant J.* 6:861-877 (1994); Jorgensen, *Trends Biotechnol.* 8:340-344 (1990); Meins and Kunz, In: *Gene Inactivation and Homologous Recombination in Plants*, Paszkowski (ed.), pp. 335-348, Kluwer Academic, Netherlands (1994)) (Kinney, Induced Mutations and Molecular Techniques for Crop Improvement, Proceedings of a Symposium 19-23 Jun. 1995 (jointly organized by IAEA and FA)), pages 101-113 (IAEA-SM 340-49).

It is understood that one or more of the nucleic acids of the invention may be introduced into a plant cell and transcribed using an appropriate promoter with such transcription resulting in the cosuppression of an endogenous protein. Such nucleic acid molecules may be operably linked to the same promoter in polycistronic configuration or to different promoters.

Antisense approaches are a way of preventing or reducing gene function by targeting the genetic material (Mol et al., *FEBS Lett.* 268:427-430 (1990)). The objective of the antisense approach is to use a sequence complementary to the target gene to block its expression and create a mutant cell line or organism in which the level of a single chosen protein is selectively reduced or abolished. Antisense techniques have several advantages over other 'reverse genetic' approaches. The site of inactivation and its developmental effect can be manipulated by the choice of promoter for antisense genes or by the timing of external application or microinjection. Antisense can manipulate its specificity by selecting either unique regions of the target gene or regions where it shares homology to other related genes (Hiatt et al., In: *Genetic Engineering*, Setlow (ed.), Vol. 11, New York: Plenum 49-63 (1989)).

Antisense RNA techniques involve introduction of RNA that is complementary to the target mRNA into cells, which results in specific RNA:RNA duplexes being formed by base pairing between the antisense substrate and the target mRNA (Green et al., *Annu. Rev. Biochein.* 55:569-597 (1986)). Under one embodiment, the process involves the introduction and expression of an antisense gene sequence. Such a sequence is one in which part or all of the normal gene sequences are placed under a promoter in inverted orientation so that the 'wrong' or complementary strand is transcribed into a noncoding antisense RNA that hybridizes with the target mRNA and interferes with its expression (Takayama and Inouye, *Crit. Rev. Biochem. Mol. Biol.* 25:155-184 (1990)). An antisense vector is constructed by standard procedures and introduced into cells by methods including but not limited to transformation, transfection, electroporation, microinjection, and infection. The type of transformation and choice of vector will determine whether expression is transient or stable. The promoter used for the antisense gene may influence the level, timing, tissue, specificity, or inducibility of the antisense inhibition.

It has been reported that the introduction of double-stranded RNA into cells may also be used to disrupt the function of an endogenous gene. (Fire et al., *Nature* 391: 806-811 (1998)). Such disruption has been demonstrated, for example, in *Caenorhabditis elegans* and is often referred to as RNA interference, or RNAi. (Fire et al., *Nature* 391: 806-811 (1998)). The disruption of gene expression in *C. elegans* by double-stranded RNA has been reported to induce suppression by a post-transcriptional mechanism. (Montgomery et al., Proc. Natl. Acad. Sci. 95:15502-15507 (1998)). Evidence of gene silencing by double-stranded RNA has also been reported for plants. (Waterhouse et al., *Proc. Natl. Acad. Sci.* 95: 13959-13964 (1998)).

An intron-spliced hairpin structure reportedly may also be used to effect post-transcriptional gene suppression. (Smith et al., *Nature* 407: 319-320 (2000)). Reports indicate that post-transcriptional gene silencing can be induced with almost 100% efficiency by the use of intron-spliced RNA with a hairpin structure. (Smith et al., *Nature* 407: 319-320 (2000)).

It is understood that one or more of the nucleic acids of the invention may be modified in order to effect RNAi or another mode of post-transcriptional gene suppression.

The present invention also provides for parts of the plants, particularly reproductive or storage parts. Plant parts, without limitation, include seed, endosperm, ovule, pollen, roots, tubers, stems, leaves, stalks, fruit, berries, nuts, bark, pods, seeds and flowers. In a particularly preferred embodiment of the present invention, the plant part is a seed.

The present invention also provides a container of over 10,000, more preferably 20,000, and even more preferably 40,000 seeds where over 10%, more preferably 25%, more preferably 50% and even more preferably 75% or 90% of the seeds are seeds derived from a plant of the present invention.

The present invention also provides a container of over 10 kg, more preferably 25 kg, and even more preferably 50 kg seeds where over 10%, more preferably 25%, more preferably 50% and even more preferably 75% or 90% of the seeds are seeds derived from a plant of the present invention.

Any of the plants or parts thereof of the present invention may be processed to produce a feed, meal, protein, or oil preparation. A particularly preferred plant part for this purpose is a seed. In a preferred embodiment the feed, meal, protein or oil preparation is designed for livestock animals or humans, or both. Methods to produce feed, meal, protein and oil preparations are known in the art. See, for example, U.S. Pat. Nos. 4,957,748, 5,100,679, 5,219,596, 5,936,069, 6,005,076, 6,146,669, and 6,156,227. In a preferred embodiment, the protein preparation is a high protein preparation. Such a high protein preparation preferably has a protein content of greater than 5% w/v, more preferably 10% w/v, and even more preferably 15% w/v. In a preferred oil preparation, the oil preparation is a high oil preparation with an oil content derived from a plant or part thereof of the present invention of greater than 5% w/v, more preferably 10% w/v, and even more preferably 15% w/v. In a preferred embodiment the oil preparation is a liquid and of a volume greater than 1, 5, 10 or 50 liters. The present invention provides for oil produced from plants of the present invention or generated by a method of the present invention. Such an oil may exhibit enhanced oxidative stability. Also, such oil may be a minor or major component of any resultant product. Moreover, such oil may be blended with other oils. In a preferred embodiment, the oil produced from plants of the present invention or generated by a method of the present invention constitutes greater than 0.5%, 1%, 5%, 10%, 25%, 50%, 75% or 90% by volume or weight of the oil component of any product. In another embodiment, the oil preparation may be blended and can constitute greater than 10%, 25%, 35%, 50% or 75% of the blend by volume. Oil produced from a plant of the present invention can be admixed with one or more organic solvents or petroleum distillates.

In one embodiment, an oil of the present invention has an oil composition that is 50% or greater oleic acid and 10% or less linolenic acid. In another embodiment, an oil of the present invention has an oil composition that is 60% or greater oleic acid and 7% or less linolenic acid. In another embodiment, an oil of the present invention has an oil composition that is 65% or greater oleic acid and 5% or less linolenic acid, preferably 4% or less linolenic acid, and more preferably 3% or less linolenic acid.

In another embodiment, an oil of the present invention has an oil composition that is between 50% and 90% oleic acid and 10% or less linolenic acid. In another embodiment, an oil of the present invention has an oil composition that is between 60% and 80% oleic acid and 7% or less linolenic acid. In another embodiment, an oil of the present invention has an oil composition that is between 65% and 75% oleic acid and 5% or less linolenic acid, preferably 4% or less linolenic acid, and more preferably 3% or less linolenic acid.

In another embodiment, an oil of the present invention has an oil composition that is 80% or greater, more preferably 90% or greater oleic acid and 5% or less linolenic acid, preferably 4% or less linolenic acid, and more preferably 3% or less linolenic acid. In another embodiment, an oil of the present invention has an oil composition that is 50% or greater oleic acid, more preferably 60% or greater, 70% or greater, 80% or greater, or 90% or greater oleic acid. In another embodiment, an oil of the present invention has an oil composition that is 10% or less linolenic acid, preferably 5% or less, 4% or less, or 3% or less linolenic acid.

Plants of the present invention can be part of or generated from a breeding program. The choice of breeding method depends on the mode of plant reproduction, the heritability of the trait(s) being improved, and the type of cultivar used commercially (e.g., $F_1$ hybrid cultivar, pureline cultivar, etc). Selected, non-limiting approaches, for breeding the plants of the present invention are set forth below. A breeding program can be enhanced using marker assisted selection of the progeny of any cross. It is further understood that any commercial and non-commercial cultivars can be utilized in a breeding program. Plants of the present invention can be part of or generated from a breeding program. The choice of breeding method depends on the mode of plant reproduction, the heritability of the trait(s) being improved, and the type of cultivar used commercially (e.g., $F_1$ hybrid cultivar, pureline cultivar, etc). Selected, non-limiting approaches, for breeding the plants of the present invention are set forth below. A breeding program can be enhanced using marker assisted selection of the progeny of any cross. It is further understood that any commercial and non-commercial cultivars can be utilized in a breeding program.

In a non-limiting example of breeding, a soybean FAD2-1A intron suppressed line can be used to pollinate a low linolenic soybean FAD3 mutant line derived from a spontaneous mutation, or derived from but not limited to methods such as Targeted Induced Local Lesions in Genomes (TILLING) (McCallum et al., Nature Biotech, 18:455-457 (2000)), gene replacement via RNA/DNA chimeric oligonucleotides, homologous recombination, T-DNA or transposan mutagenesis. RNA from soybean seeds containing both one or more expressed FAD2 intron regions and FAD3 mutations, including knock out, can be screened using Northern blots (as described in Example 5) to determine the levels of FAD2-1, FAD2-2, FAD3-1A, FAD3-1C and FAD3-1B transcripts. The resulting plant is expected to have the attributes of both parents. Soybean plants with undetectable or low levels of FAD2 or FAD3 transcripts can be screened for fatty acid composition.

Plants of the present invention can be part of or generated from a breeding program, for example, where a soybean FAD3-1A, FAD3-1B, and/or FAD3-1 C intron suppressed line is used to pollinate soybean plants with elevated levels of oleic acid containing a FAD2 mutant line derived from a spontaneous mutation, or derived from non-limiting methods such as, for example, TILLING, gene replacement via RNA/DNA chimeric oligonucleotides, homologous recombination, T-DNA or transposan mutagenesis. RNA from soybean seeds containing both one or more expressed FAD3 intron regions and FAD2 mutations, including knock out, can be screened using Northern blotting (as described in Example 5) to determine the levels of FAD2-1, FAD2-2, FAD3-1A, FAD3-1B, and FAD3-1C transcripts. Soybean plants with undetectable or low levels of FAD2 or FAD3 transcripts can be screened for fatty acid composition. Resulting plants are expected to have the attributes of both parents.

The development of new cultivars requires the development and selection of varieties, the crossing of these varieties and the selection of superior hybrid crosses. The hybrid seed can be produced by manual crosses between selected male-fertile parents or by using male sterility systems. Hybrids are selected for certain single gene traits such as pod color, flower color, seed yield, pubescence color, or herbicide resistance, which indicate that the seed is truly a hybrid. Additional data on parental lines, as well as the phenotype of the hybrid, influence the breeder's decision whether to continue with the specific hybrid cross. The parents in such hybrid production can be, for example, a soybean FAD2-1A intron suppressed line, a soybean FAD3-1A, FAD3-1B and/or FAD3-1C intron suppressed line or an intron suppressed line containing FAD2-1A, FAD3-1A, FAD3-1B and/or FAD3-1C in any desired combination. Any of these parents may be crossed with, for example, any naturally occurring or manmade mutant line with increased levels of oleic acid and/or decreased levels of linolenic acid.

Backcross breeding has been used to transfer genes for a simply inherited, highly heritable trait, such as transgenes, into a desirable homozygous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting parent is expected to have the attributes of the recurrent parent (e.g., cultivar) and the desirable trait transferred from the donor parent. The donor parent in such a backcross production may be, for example, a soybean FAD2-1A intron suppressed line or a soybean FAD3-1A, FAD3-1B and/or FAD3-1C intron suppressed line or an intron suppressed line containing FAD2-1A, FAD3-1A, FAD3-1B and/or FAD3-1C in any desired combination. The recurrent parent can be for example any naturally occurring or manmade mutant line with increased levels of oleic acid and/or decreased levels of linolenic acid.

Computer Readable Medium

The nucleotide sequence provided in SEQ ID NO: 1 through 15, 18, 19, 22, 23, or fragment thereof or complement thereof, or a nucleotide sequence at least 50%, 60%, or 70% identical, preferably 80%, 85% identical, or especially preferably 90%, or 95% identical, or particularly highly preferably 97%, 98%, or 99% identical to the sequence provided in SEQ ID NO: 1 through 15, 18, 19, 22, 23, or fragment thereof or complement thereof, can be "provided" in a variety of media to facilitate use. Such a medium can also provide a subset thereof in a form that allows a skilled artisan to examine the sequences.

In one application of this embodiment, a nucleotide sequence of the present invention can be recorded on computer readable media. As used herein, "computer readable media" refers to any medium that can be read and accessed directly by a computer. Such media include, but are not llinited to: magnetic storage media, such as floppy disk, hard disc, storage medium, and magnetic tape; optical storage media such as CD-ROM; electrical storage media such as RAM and ROM; and hybrids of these categories such as magnetic/optical storage media. A skilled artisan can readily appreciate how any of the presently known computer readable media can be used to create a manufacture comprising a computer readable medium having recorded thereon a nucleotide sequence of the present invention.

As used herein, "recorded" refers to a process for storing information on computer readable medium. A skilled artisan can readily adopt any of the presently known methods for recording information on computer readable media to generate media comprising the nucleotide sequence information of the present invention. A variety of data storage structures are available to a skilled artisan for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable media. The sequence information can be represented in a word processing text file, formatted in commercially-available software such as Word Perfect and Microsoft Word, or represented in the form of an ASCII file, stored in a database application, such as DB2, Sybase, Oracle, or the like. A skilled artisan can readily adapt any number of data processor structuring formats (e.g. text file or database) in order to obtain computer readable media having recorded thereon the nucleotide sequence information of the present invention.

By providing one or more nucleotide sequences of the present invention, a skilled artisan can routinely access the sequence information for a variety of purposes. Computer software is publicly available which allows a skilled artisan to access sequence information provided in a computer readable medium. Software which implements the BLAST (Altschul et al., *J. Mol. Biol.* 215: 403-410 (1990)) and BLAZE (Brutlag et al., *Comp. Chem.* 17:203-207 (1993)) search algorithms on a Sybase system can be used to identify non-coding regions and other nucleic acid molecules of the present invention within the genome that contain homology to non-coding regions from other organisms. Such non-coding regions may be utilized to affect the expression of commercially important proteins such as enzymes used in amino acid biosynthesis, metabolism, transcription, translation, RNA processing, nucleic acid and protein degradation, protein modification, and DNA replication, restriction, modification, recombination, and repair.

The present invention further provides systems, particularly computer-based systems, which contain the sequence information described herein. Such systems are designed to identify commercially important fragments of the nucleic acid molecules of the present invention. As used herein, "a computer-based system" refers to the hardware means, software means, and data storage means used to analyze the nucleotide sequence information of the present invention. The minimum hardware means of the computer-based systems of the present invention comprises a central processing unit (CPU), input means, output means, and data storage means. A skilled artisan can readily appreciate that any one of the currently available computer-based systems is suitable for use in the present invention.

As indicated above, the computer-based systems of the present invention comprise a data storage means having stored therein a nucleotide sequence of the present invention and the necessary hardware means and software means for supporting and implementing a search means. As used herein, "data storage means" refers to memory that can store nucleotide sequence information of the present invention, or a memory access means which can access manufactures having recorded thereon the nucleotide sequence information of the present invention. As used herein, "search means" refers to one or more programs which are implemented on the computer-based system to compare a target sequence or target structural motif with the sequence information stored within the data storage means. Search means are used to identify fragments or regions of the sequence of the present invention that match a particular target sequence or target motif. A variety of known algorithms are disclosed publicly and a variety of commercially available software for conducting search means are available and can be used in the computer-based systems of the present invention. Examples of such software include, but are not limited to, MacPattern (EMBL), BLASTIN, and BLASTIX (NCBIA). One of the available algorithms or implementing software packages for conducting homology searches can be adapted for use in the present computer-based systems.

The most preferred sequence length of a target sequence is from about 10 to 100 amino acids or from about 30 to 300 nucleotide residues. However, it is well recognized that during searches for commercially important fragments of the nucleic acid molecules of the present invention, such as sequence fragments involved in gene expression and protein processing, the target sequence may be of shorter length.

As used herein, "a target structural motif," or "target motif" refers to any rationally selected sequence or combination of sequences in which the sequences are chosen based on a three-dimensional configuration which is formed upon the folding of the target motif. There are a variety of target motifs known in the art. Protein target motifs include, but are not limited to, enzymatic active sites and signal sequences. Nucleic acid target motifs include, but are not limited to, promoter sequences, cis elements, hairpin structures, and inducible expression elements (protein binding sequences).

Thus, the present invention further provides an input means for receiving a target sequence, a data storage means for storing the target sequences of the present invention sequence identified using a search means as described above, and an output means for outputting the identified homologous sequences. A variety of structural formats for the input and output means can be used to input and output information in the computer-based systems of the present invention. A preferred format for an output means ranks fragments of the sequence of the present invention by varying degrees of homology to the target sequence or target motif. Such presentation provides a skilled artisan with a ranking of sequences which contain various amounts of the target sequence or target motif and identifies the degree of homology contained in the identified fragment.

A variety of comparing means can be used to compare a target sequence or target motif with the data storage means to identify sequence fragments sequence of the present invention. For example, implementing software that implement the BLAST and BLAZE algorithms (Altschul et al., *J. Mol. Biol.* 215:403-410 (1990)) can be used to identify non-coding regions within the nucleic acid molecules of the present invention. A skilled artisan can readily recognize that any one of the publicly available homology search programs can be used as the search means for the computer-based systems of the present invention.

The following examples are illustrative and not intended to be limiting in any way.

EXAMPLES

Example 1

Cloning of Desaturase Genomic Sequences

1A. Soybean Δ12 Desaturase (FAD2-1)

A soybean FAD2-1A sequence is identified by screening a soybean genomic library using a soybean FAD2-1 cDNA probe. Three putative soy FAD2-1 clones are identified and plaque purified. Two of the three soy FAD2-1 clones are ligated into pBluescript II KS+ (Stratagene) and sequenced. Both genomic clones (14-1 and 11-12) are the same and matched the corresponding sequence in the soy FAD2-1 cDNA exactly. A sequence of the entire FAD2-1A clone is provided in SEQ ID NO:15.

Prior to obtaining a full length clone, a portion of the FAD2-1A genomic clone is PCR amplified using PCR primers designed from the 5' untranslated sequence (Primer 12506, 5'-ATACAA GCCACTAGGCAT-3', SEQ ID NO:16) and within the cDNA (Primer 11698: 5'-GATTGGCCATG-CAATGAGGGAAAAGG-3', SEQ ID NO:17). The resulting PCR product is cloned into the vector pCR 2.1 (Invitrogen, Carlsbad, Calif.) and sequenced. A soy FAD2-1A partial genomic clone (SEQ ID NO:18) with an intron region (SEQ ID NO:1) is identified by comparison to the soybean cDNA sequence using the Pustell comparison program in Macvector. The FAD2-1A intron sequence (SEQ ID NO:1) begins after the ATG start codon, and is 420 bases long.

A second FAD2-1 gene family member is also identified and cloned, and is referred to herein as FAD2-1B. The soy FAD2-1B partial genomic clone (SEQ ID NO:19) has a coding region (base pairs 1783-1785 and 2191-2463) and an intron region (base pairs 1786-2190) which are identified by comparison to the soybean cDNA sequence using the Pustell comparison program in Macvector. The FAD2-1B intron sequence (SEQ ID NO:2) begins after the ATG start codon and is 405 bases long. Other regions in the FAD2-1B partial genomnic clone (SEQ ID NO:19) include a promoter (base pairs 1-1704) (SEQ ID NO:22) and 5'UTR (base pairs 1705-1782).

1B. Soybean Δ15 Desaturase (FAD3)

A partial soybean FAD3-1A genomic sequence is PCR amplified from soybean DNA using primers 10632, 5'-CUACUACUACUACTCGAGACAAAGCCTT-TAGCCTATG-3' (SEQ ID NO:20), and 10633: 5'-CAUCAU-CAUCAUGGATCCCATGTCTCTCTATGCAAG-3' (SEQ ID NO:21). The Expand Long Template PCR system (Roche Applied Sciences, Indianapolis) is used according to the manufacturer's directions. The resulting PCR products are cloned into the vector pCR 2.1 (Invitrogen) and sequenced. A soy FAD3-1A partial genomic clone sequence (SEQ ID NO: 23) and intron regions are confirmed by comparisons to the soybean FAD3-1A cDNA sequence using the Pustell program in Macvector.

From the identified partial genomic soybean FAD3-1A sequence (SEQ ID NO:23), seven introns are identified: FAD3-1A intron #1(SEQ ID NO:5), FAD3-1A intron #2 (SEQ ID NO:6), FAD3-1A intron #3A (SEQ ID NO:7), FAD3-1A intron #4 (SEQ ID NO:8), FAD3-1A intron #5 (SEQ ID NO:9), FAD3-1A intron #3B (SEQ ID NO:10), and FAD3-1A intron #3C (SEQ ID NO:11). FAD3-1A intron #1 is 191 base pairs long and is located between positions 294 and 484, FAD3-1A intron #2 is 346 base pairs long and is located between positions 577 and 922, FAD3-1A intron #3A is 142 base pairs long and is located between positions 991 and 1132, FAD3-1A intron #3B is 98 base pairs long and is located between positions 1224 and 1321, FAD3-1A intron #3C is 115 base pairs long and is located between positions 1509 and 1623, FAD3-1A intron #4 is 1228 base pairs long and is located between positions 1707 and 2934, and FAD3-1A intron #5 is 625 base pairs long and is located between positions 3075 and 3699.

A partial soybean FAD3-1B genomic sequence is PCR amplified from soybean DNA using primers 19386, 5'-GG- TAACAGAGAAAGAAACATTTGAGC-3' and 19369: 5'-GCATGCTAACAAAAGTAAGTGC-3'. The Expand Long Template PCR system (Roche Applied Sciences, Indianapolis) is used according to the manufacturer's directions. The resulting PCR products are cloned into the vector pCR 2.1 TOPO (Invitrogen) and sequenced. A soy FAD3-1B partial genomic clone sequence and intron regions are confirmed by comparisons to the soybean FAD3-1B cDNA sequence using the Pustell program in Sequencher. From the identified partial genomic soybean FAD3-1B sequence, seven introns are identified: FAD3-1B intron #1, FAD3-1B intron #2, FAD3-1B intron #3A, FAD3-1B intron #4 (SEQ ID NO:13), FAD3-1B intron #5, FAD3-1B intron #3B, and FAD3-1B intron #3C (SEQ ID NO:12).

Example 2

Expression Constructs

2A. Construction of pCGN5468, pCGN5469, pCGN5471, pCGN5485, and pCGN5486

Figure 2:
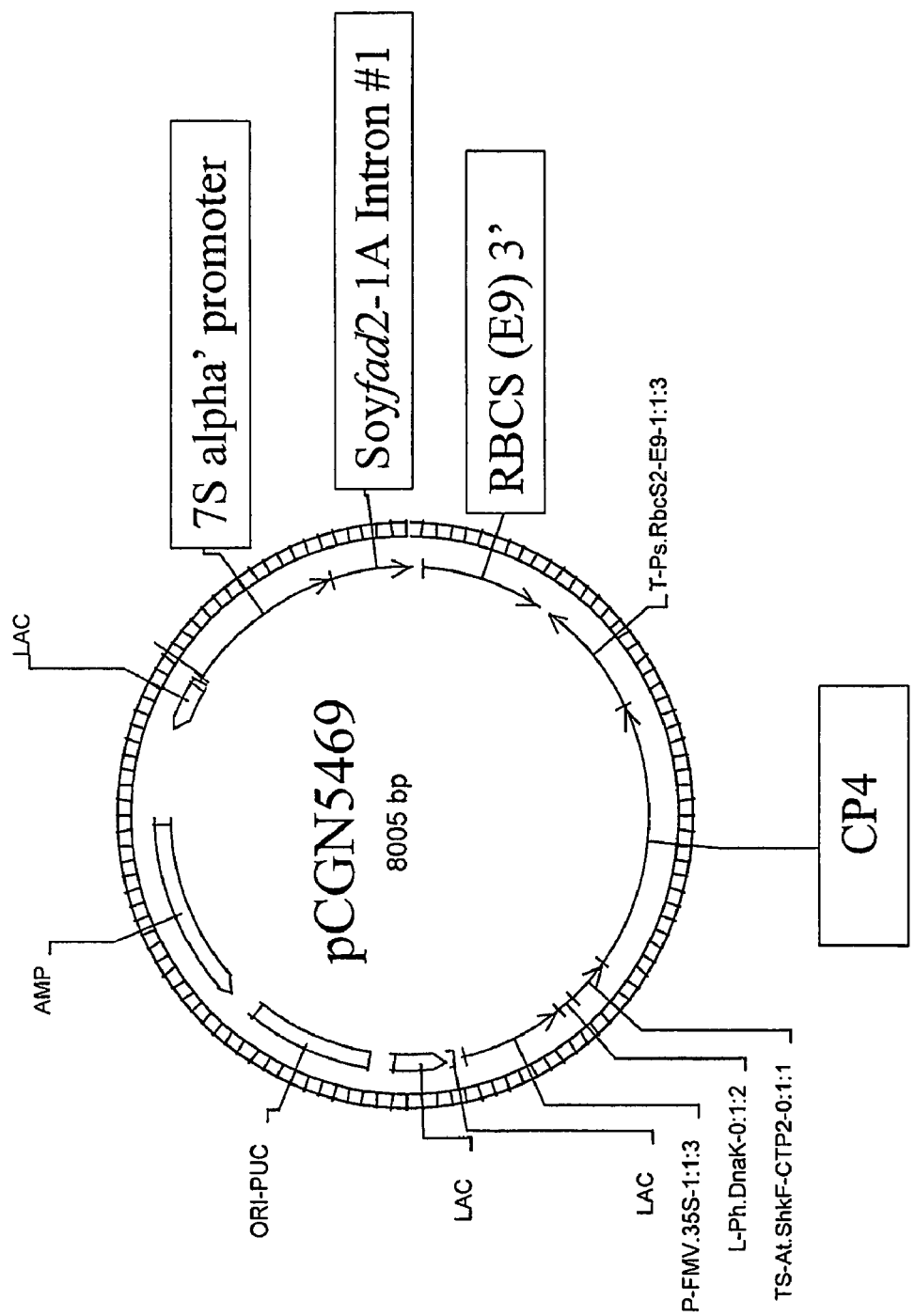
FIG. 2 is a schematic of construct pCGN5469.
Figure 3:
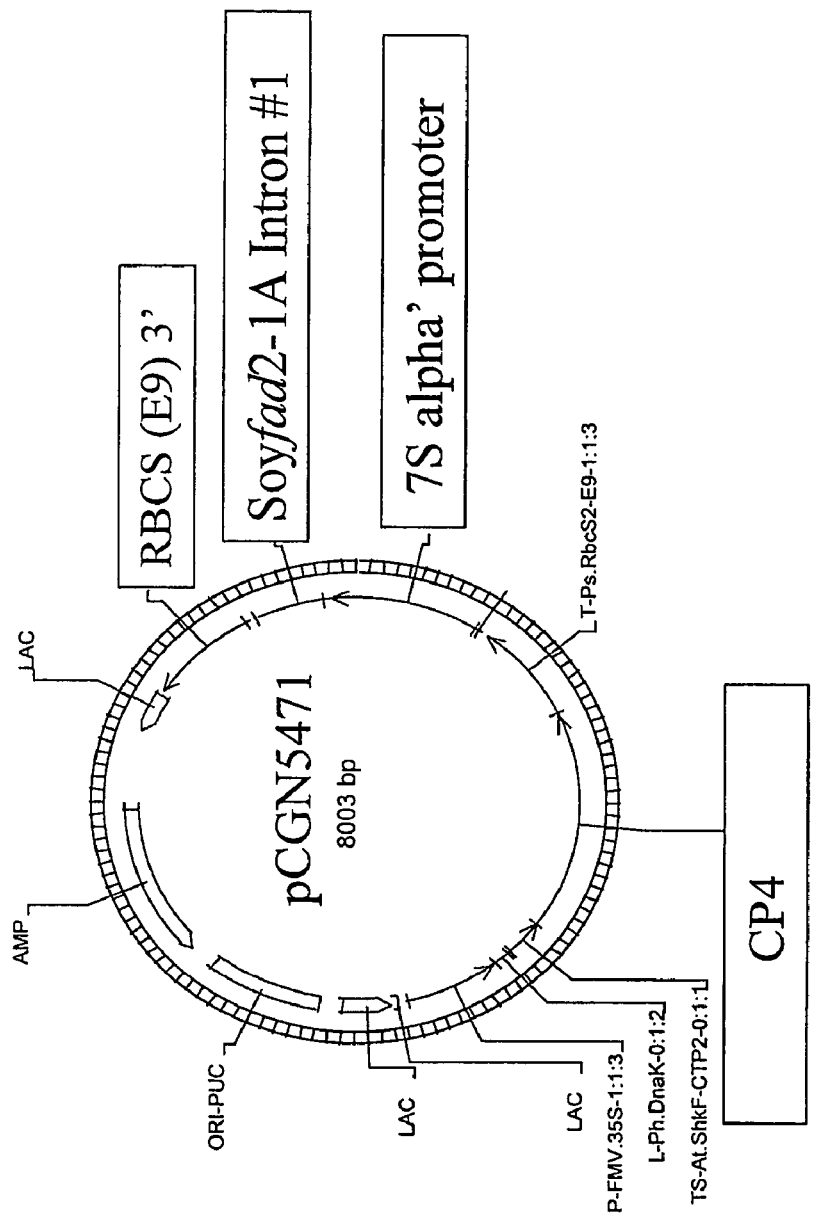
FIG. 3 is a schematic of construct pCGN5471.

The FAD2-1A intron sequence (SEQ ID NO: 1) is amplified via PCR using the FAD2-1A partial genomic clone (SEQ ID NO:18) as a template and primers 12701 (5'-ACGAAT-TCCTCGAGGTAAA TTAAATTGTGCCTGC-3' (SEQ ID NO:24)) and 12702 (5'-GCGAGATCTATCG ATCTGTGT-CAAAGTATAAAC-3' (SEQ ID NO:25)). The resulting amplification products are cloned into the vector pCR 2.1 (Invitrogen) and sequenced. The FAD2-1A intron (SEQ ID NO: 1) is then cloned into the expression cassette, pCGN3892, in sense and antisense orientations. The vector pCGN3892 contains the soybean 7S promoter and a pea RBCS 3'. Both gene fusions are then separately ligated into pCGN9372, a vector that contains the CP4 gene regulated by the FMV promoter. The resulting expression constructs (pCGN5469 sense (FIG. 2) and pCGN5471 antisense (FIG. 3)) are used for transformation of soybean using biolistic methods described below.

Figure 4:
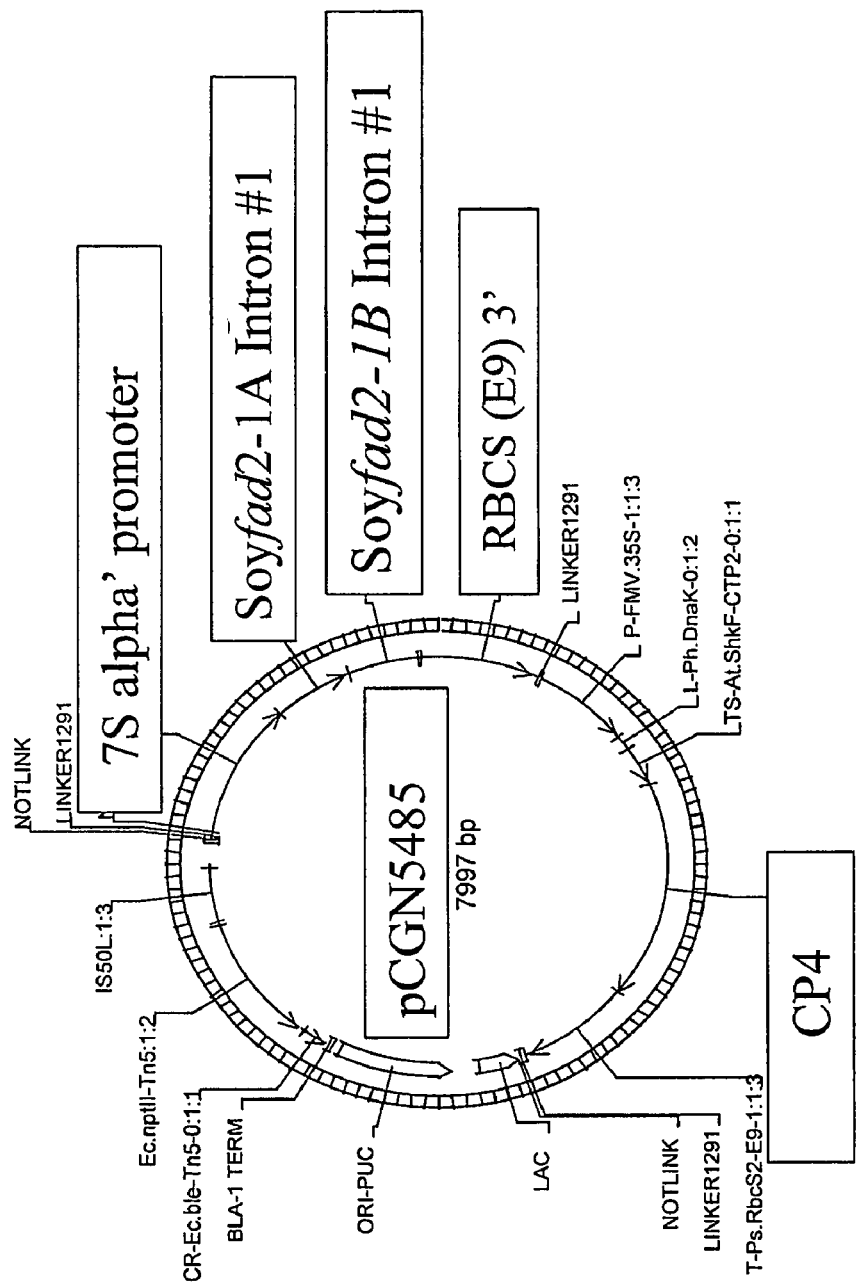
FIG. 4 is a schematic of construct pCGN5485.
Figure 5:
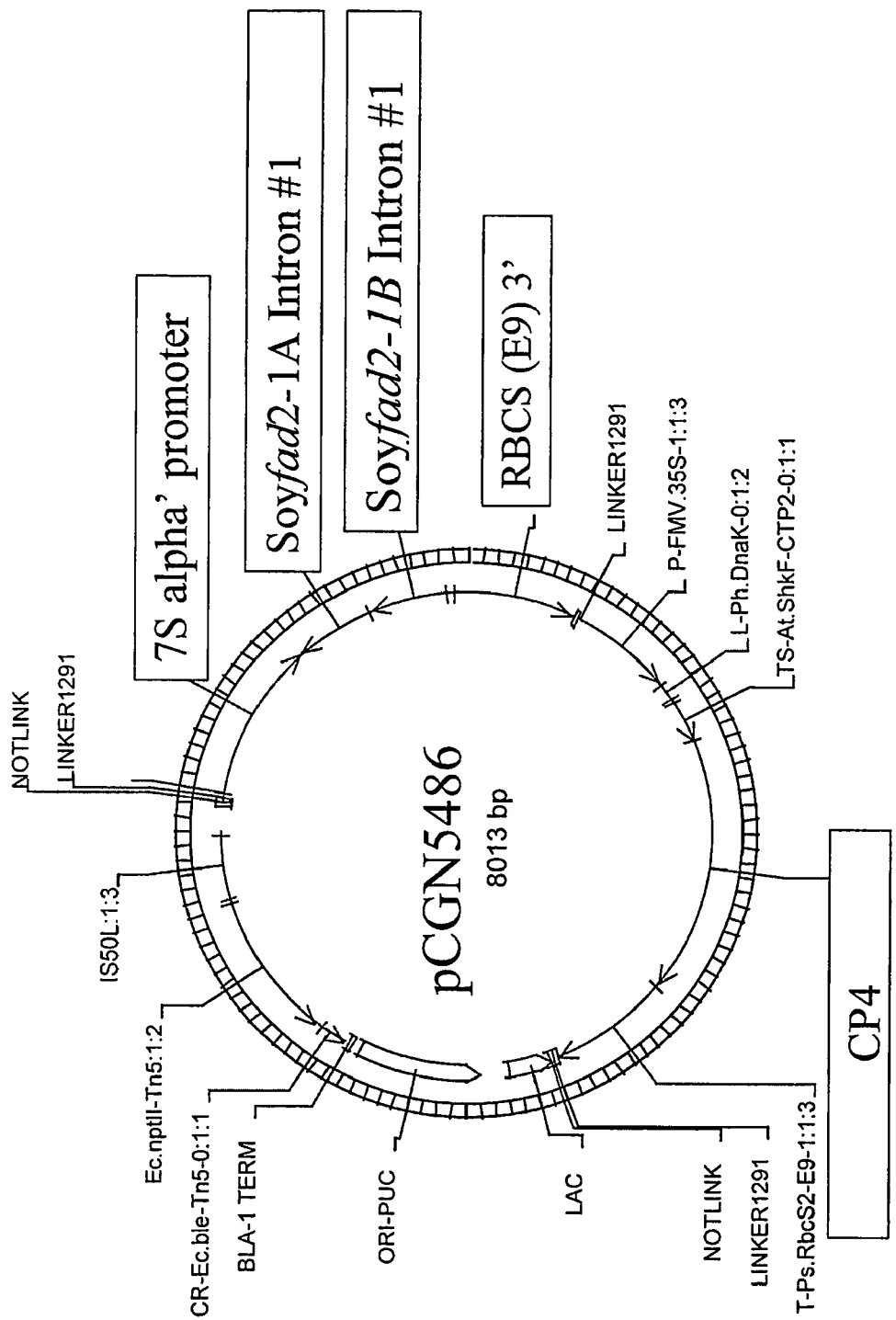
FIG. 5 is a schematic of construct pCGN5486.
Figure 6:
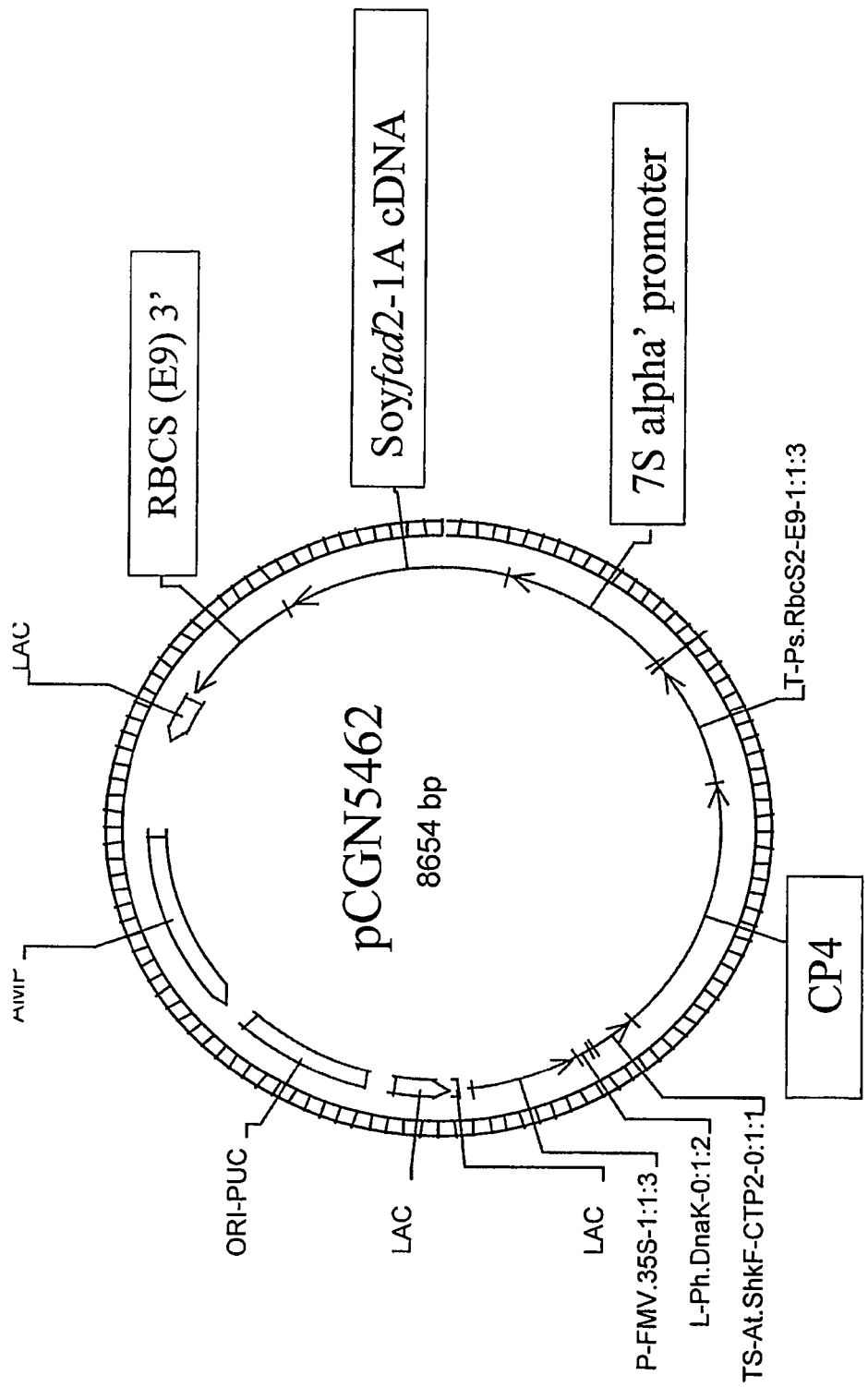
FIG. 6 is a schematic of construct pCGN5462.

The FAD2-1B intron sequence (SEQ ID NO: 2) is amplified via PCR using the FAD2-1B partial genomic clone (SEQ ID NO: 19) as a template and primers 13883 (5'-GCGATC-GATGTATGATGCTAAATTAAATTGTGCCTG-3' (SEQ ID NO:28)) and 13876 (5'-GCGGAATTCCTGTGT-CAAAGTATAAAGAAG-3' (SEQ ID NO:29)). The resulting amplification products are cloned into the vector pCR 2.1 (Invitrogen) and sequenced. The FAD2-1B intron is fused to the 3' end of the FAD2-1A intron in plasmids pCGN5468 (FIG. 1) (containing the soybean 7S promoter fused to the FAD2-1A intron (sense) and a pea RBCS 3') or pCGN5470 (containing the soybean 7S promoter fused to the FAD2-1A intron (antisense) and a pea RBCS 3') in sense or antisense orientation, respectively. The resulting intron combination fusions are then ligated separately into pCGN9372, a vector that contains the CP4 gene regulated by the FMV promoter. The resulting expression constructs (pCGN5485 (FIG. 4), FAD2-1A & FAD2-1B intron sense; and pCGN5486 (FIG. 5), FAD2-1A & FAD2-1B intron antisense) are used for transformation of soybean using biolistic methods described below.

2B. PCR Amplification of FAD3-1A Introns

Four of the seven introns identified from the soybean FAD3-1A genomic clone are PCR amplified using the FAD3-1A partial genomic clone as template and primers as follows: FAD3-1A intron #1, primers 12568: 5'-GATCGATGC-CCGGGGTAATAATTTTTGTGT-3' (SEQ ID NO:30) and 12569: 5'-CACGCCTCGAGTGTTCAATTCAATCAATG-3' (SEQ ID NO:31); FAD3-1A intron #2, primers 12514: 5'-CACTCGAGTTAGTTCATACTGGCT-3' (SEQ ID NO:32) and 12515: 5'-CGCATCGATTGCAAAATCCAT-CAAA-3' (SEQ ID NO:33); FAD3-1A intron #4, primers 10926: 5'-CUACUACUACUACTCGAGCGTAAAT-AGTGGGTGAACAC-3' (SEQ ID NO:34) and 10927: 5'-CAUCAUCAUCAUCTCGAGGAATTCGTC-CATTTTAGTACACC-3' (SEQ ID NO:35); FAD3-1A intron #5, primers 10928: 5'-CUACUACUACUACTCGAG-GCGCGT ACATTTTATTGCTTA-3' (SEQ ID NO:36) and 10929: 5'-CAUCAUCAUCAUCT CGAGGAATTCTG-CAGTGAATCCAAATG-3' (SEQ ID NO:37). The resulting PCR products for each intron are cloned into the vector pCR 2.1 (Invitrogen) and sequenced.

2C. Construction of pCGN5455, pCGN5459, pCGN5456, pCGN5460, pCGNS466, and pCGN5473

Figure 7:
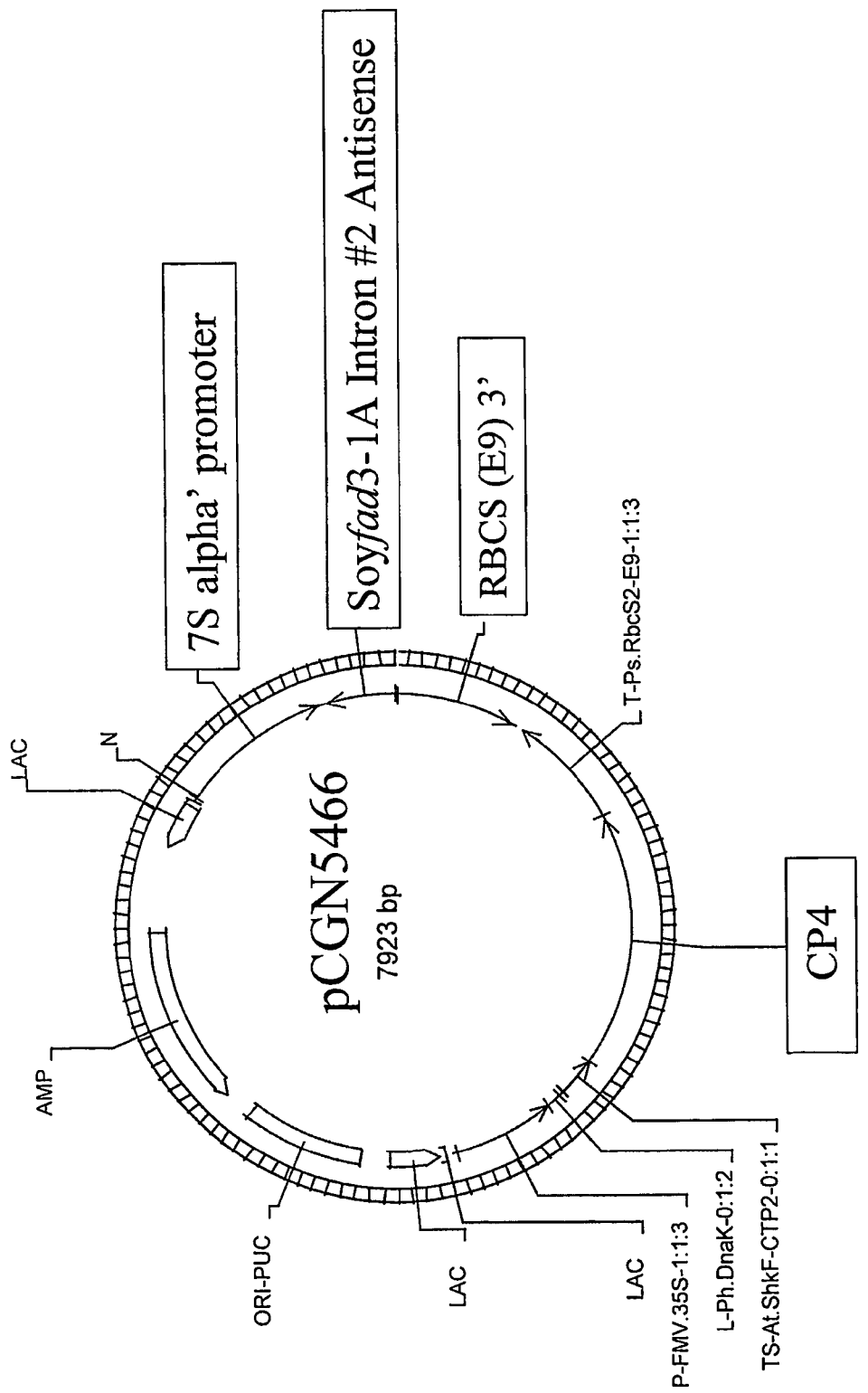
FIG. 7 is a schematic of construct pCGN5466.
Figure 8:
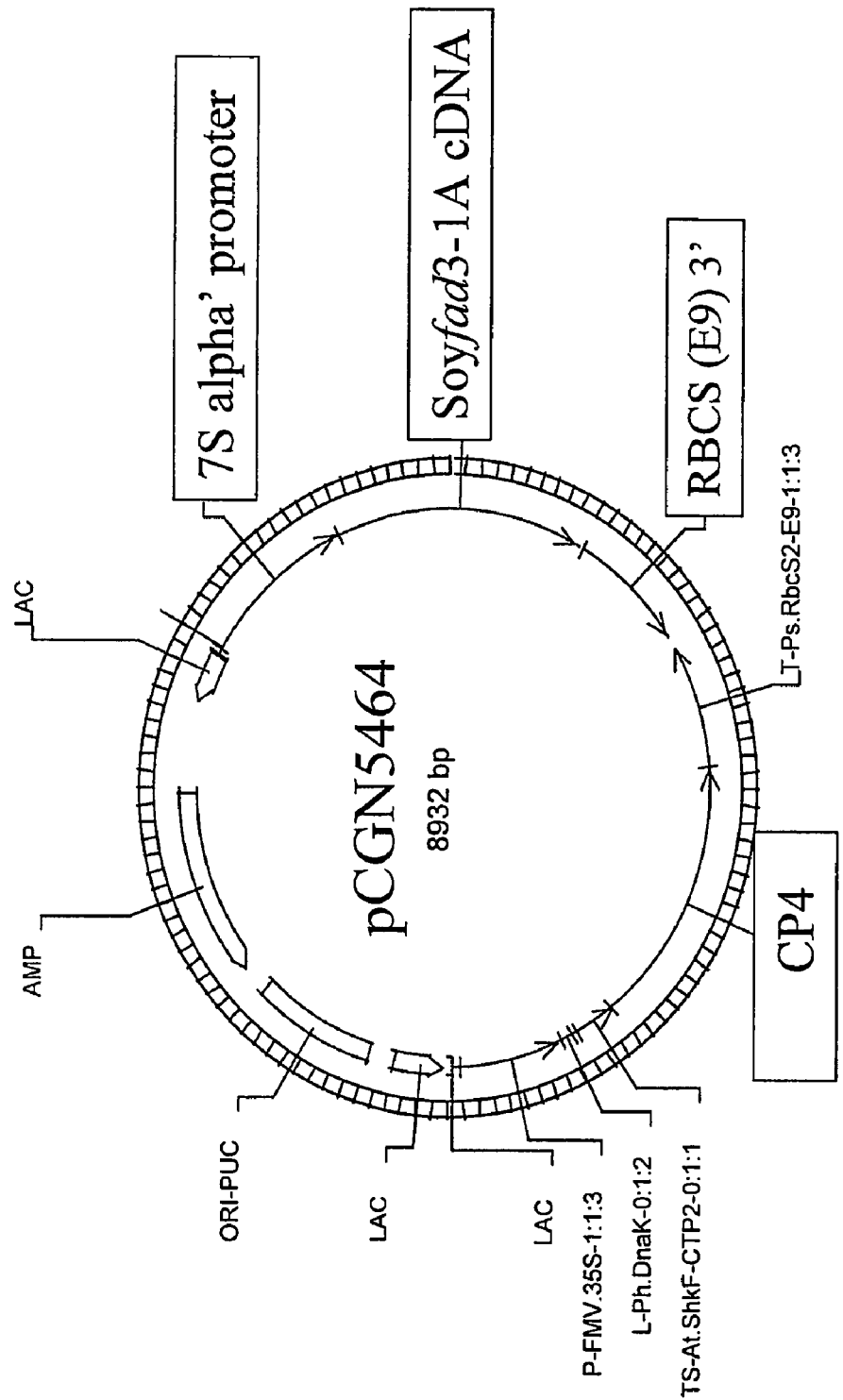
FIG. 8 is a schematic of construct pCGN5464.
Figure 9:
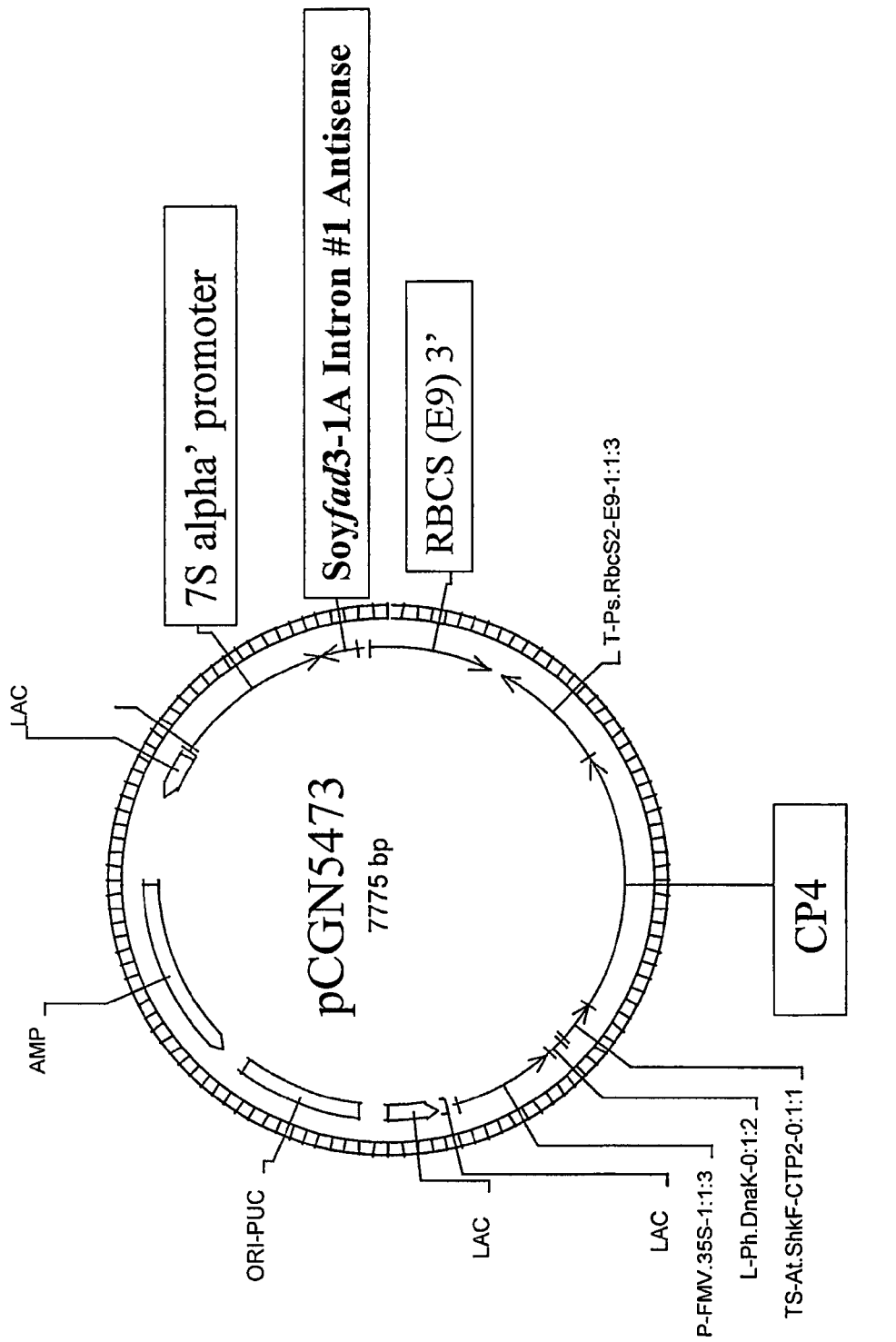
FIG. 9 is a schematic of construct pCGN5473.
Figure 12:
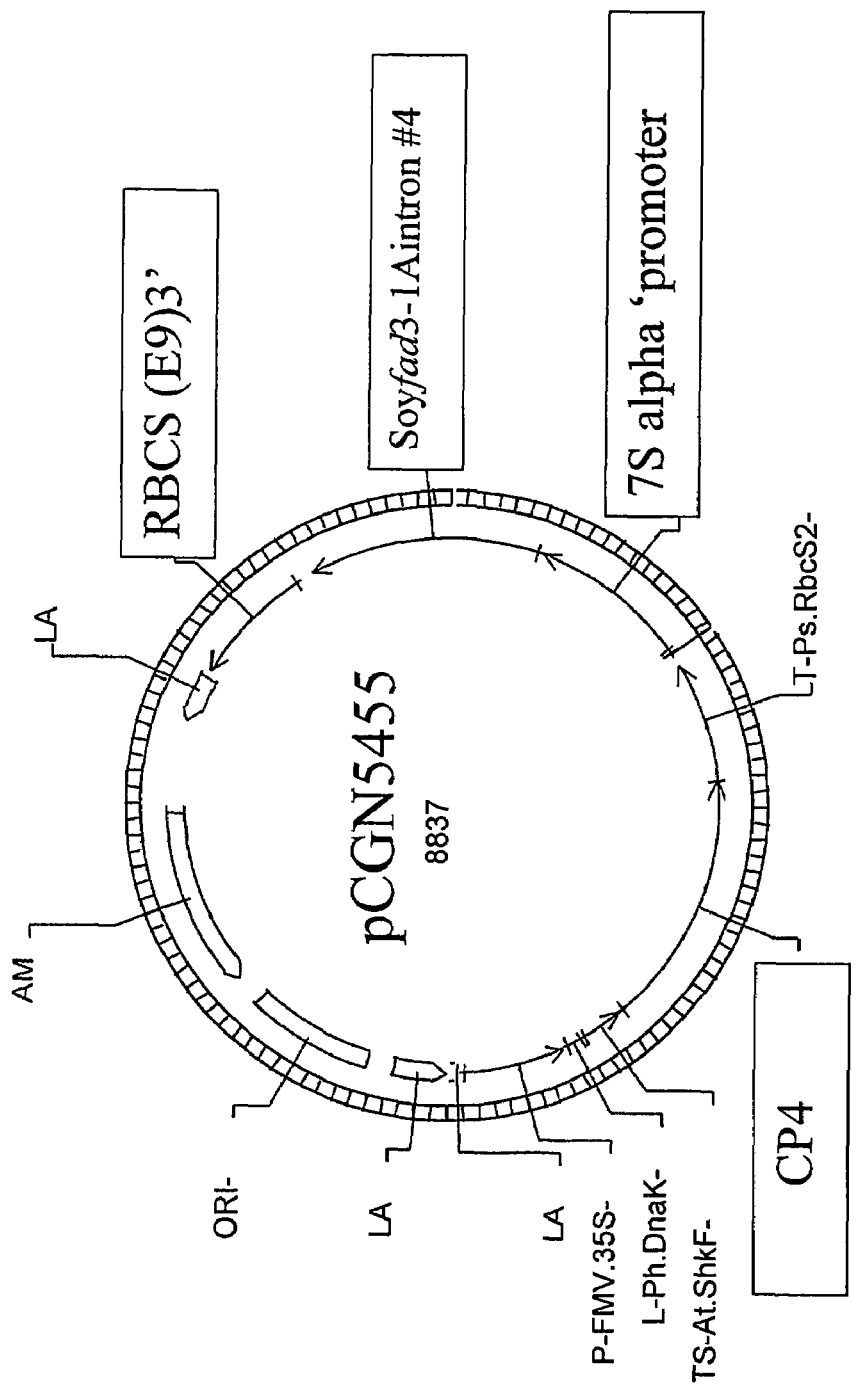
FIG. 12 is a schematic of construct pCGN5455.
Figure 13:
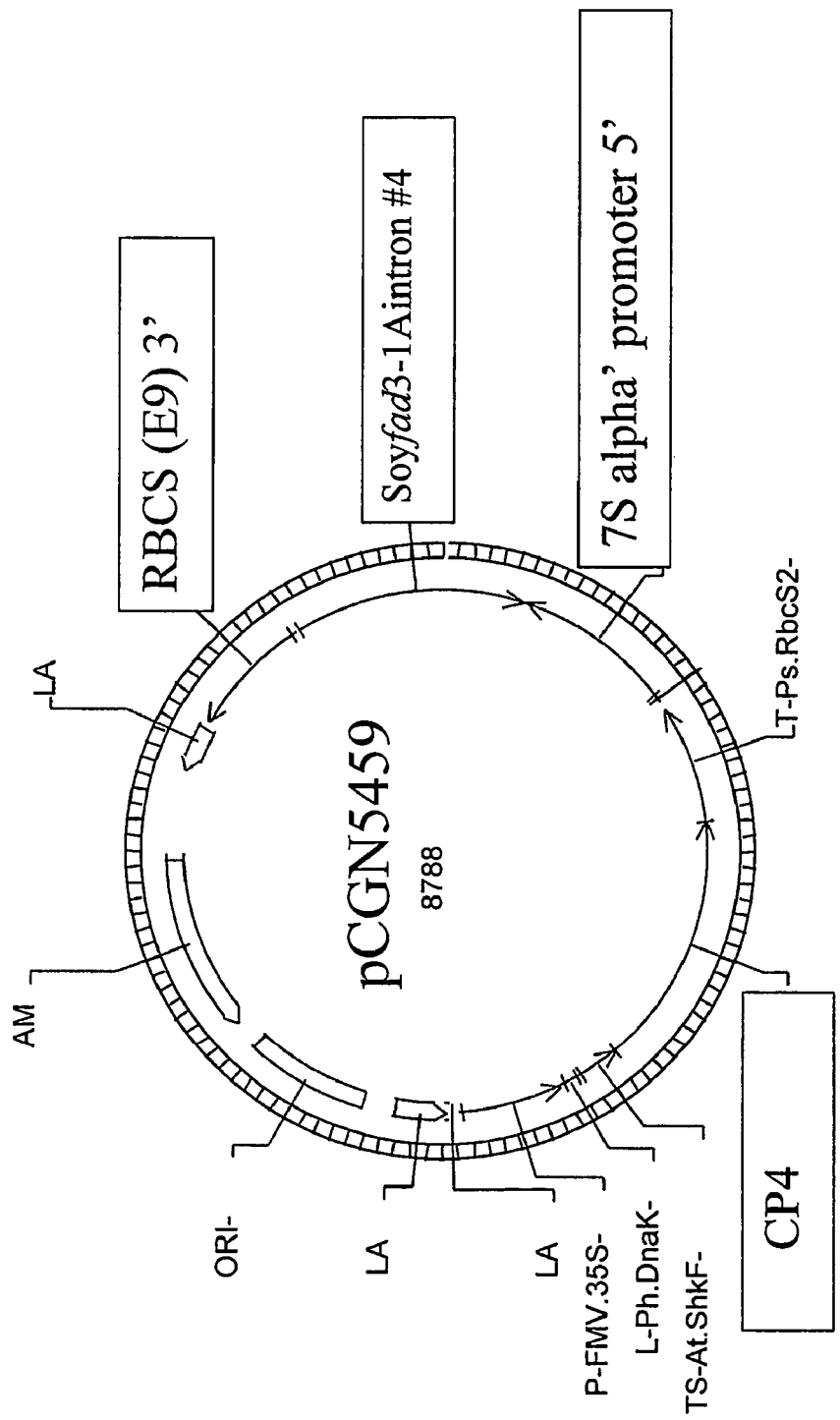
FIG. 13 is a schematic of construct pCGN5459.

FAD3-1A introns #1, #2, #4 and #5 are each ligated separately into pCGN3892, in sense or antisense orientations. pCGN3892 contains the soybean 7S promoter and a pea RBCS 3'. These fusions are ligated into pCGN9372, a vector that contains the CP4 gene regulated by the FMV promoter for transformation into soybean. The resulting expression constructs (pCGN5455 (FIG. 12), FAD3-1A intron #4 sense; pCGN5459 (FIG. 13), containing FAD3-1A intron #4 antisense; pCGN5456, FAD3 intron #5 sense; pCGN5460, FAD3-1A intron #5 antisense; pCGN5466 (FIG. 7), containing FAD3-1A intron #2 antisense; pCGN5473 (FIG. 9), containing FAD3-1A intron #1 antisense) are used for transformation of soybean using biolistic methods described below.

Introns #3C and #4 are also PCR amplified from a second FAD3 gene family member (FAD3-1B). Soybean FAD3-1B introns #3C and #4 are PCR amplified from soybean DNA using the following primers, 5' CATGCTTTCTGTGCT-TCTC 3' (SEQ ID NO:26) and 5' GTTGATCCAACCAT-AGTCG 3' (SEQ ID NO:27). The PCR products are cloned into the vector pCR 2.1 (Invitrogen) and sequenced. Sequences for FAD3-1B introns #3C and #4 are provided in SEQ ID NOs:12 and 13, respectively.

Intron #4 from three soybean FAD3 gene family members, FAD3-1A, FAD3-1B and FAD3-1C is PCR amplified. Intron #4 from the FAD3-1A gene is PCR amplified using the FAD3-1A partial genomic clone as template and primers 10926: 5'-CUACUACUACUACTCGAGCG-TAAATAGTGGGTGAACAC-3' (SEQ ID NO:34) and 10927: 5'-CAUCAUCAUCAUCTCGAGGAATTCGTC-CATTTTAGTACACC-3' (SEQ ID NO:35). Intron #4 from the FAD3-1B gene is PCR amplified using the soybean genomic DNA as template and primers #17823: GTATC-CCATTTAACAC and #17824: CTGTGAAATTA-CATATAG. Intron #4 from the FAD3-1C gene is PCR amplified using the soybean genomic DNA as template and primers #17826: GCGCCGCTCGAGCTGTCCATTTTTGTACAC and #17825: CCGGCGCTCGAGGTAA-CAAAAATAAATAGAAAATAGTGAGTG. The resulting PCR products for each intron were cloned into the vector pCR 2.1 (Invitrogen) and sequenced. FAD3-1A intron, #4 was ligated into the pCGN3892 in sense orientation. The resulting expression cassette, pCGN5453, contained the 7S alpha' promoter fused to the FAD3-1A intron #4, with a pea RBCS 3'.

2D. Construction of pMON68521

Figure 10:
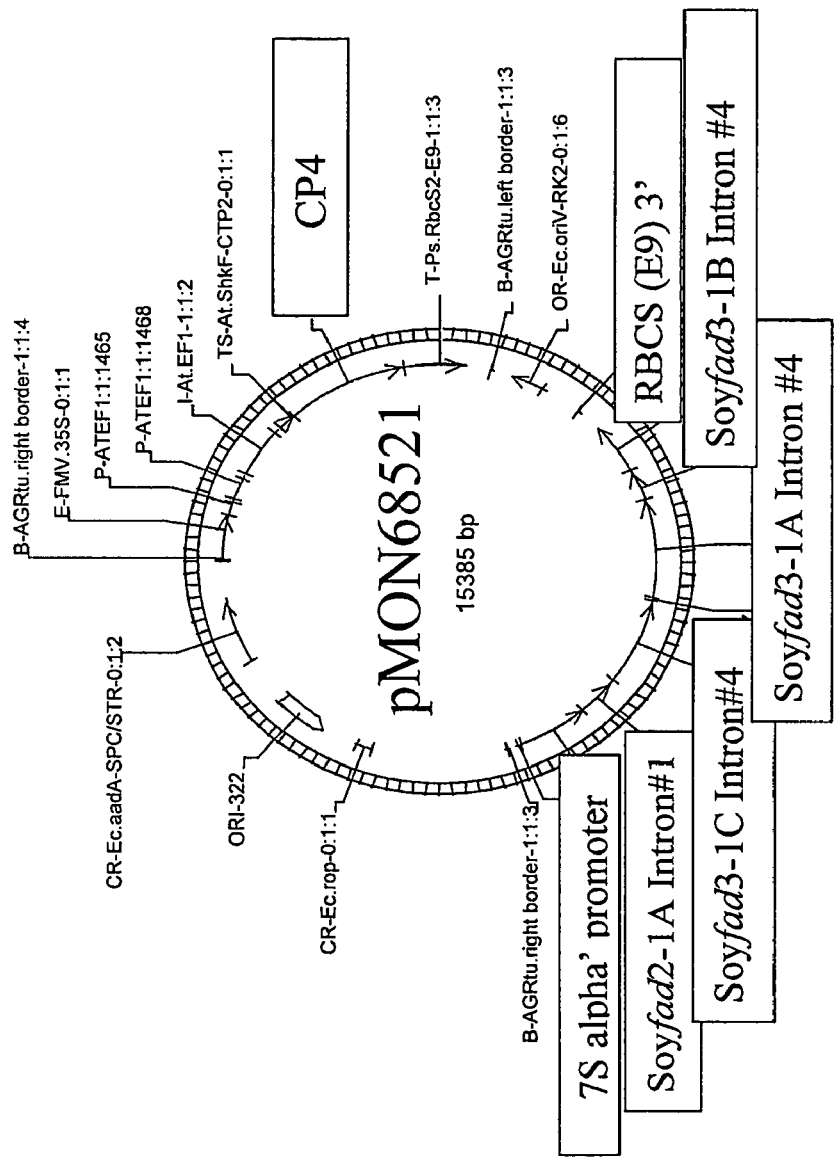
FIG. 10 is a schematic of construct pMON68521.

To construct pMON68521 (FIG. 10), pCGN5453 (7S alpha' promoter fused to the FAD3-1 A intron #4, with a pea RBCS 3') and KWHIT032858 (PCR2.1 containing the FAD3-1B intron #4) are digested with EcoRI and ligated together to form KWHIT03004 (7Salpha' promoter fused to the FAD3-1A intron #4 and FAD3-1B intron #4, with a pea RBCS 3'). KWHIT03004 is digested with XhoI and KAWHIT032980 (FAD3-1C intron #4 in PCR2.1) is digested with EcoRI and the ends of both digested plasmids are filled and subsequently ligated. The resulting plasmid is KAWHIT030005 (7Salpha' promoter fused to the FAD3-1A intron #4, FAD3-1B intron #4, and FAD3-1B intron #4, with a pea RBCS 3'). KAWHIT030005 is digested with SacI and the ends are filled using the Klenow fragment of T4 polymerase to create blunt ends. pCGN5468 (FIG. 1, containing 7S alpha' promoter fused to the FAD2-1A intron, with a pea RBCS 3') is digested with EcoRI and the ends are filled with Klenow fragment of T4 polymerase to form blunt ends. The blunt ends of plasmids KAWHIT030005 and pCGN5468 are ligated together to form KWHIT03001 (7S alpha' promoter fused to the FAD2-1A intron, the FAD3-1A intron #4, FAD3-1B intron #4, FAD3-1C intron #4, with a pea RBCS 3'). KWHIT03001 and pMON 70276 (FMV-EF-1/CP4) are both digested with NotI, ligated together to form pMON68521 (FIG. 10, 7S alpha' promoter fused to the FAD2-1A intron, the FAD3-1A intron #4, FAD3-1B intron #4, FAD3-1C intron #4, with a pea RBCS 3' and FMV-EF-1/CP4, with a pea RBCS 3'). pMON68521 was transformed into the ABI strain of *Agrobacterium tumefaciens* and cocultivated into soybean.

2E. Construction of pMON68519

Figure 11:
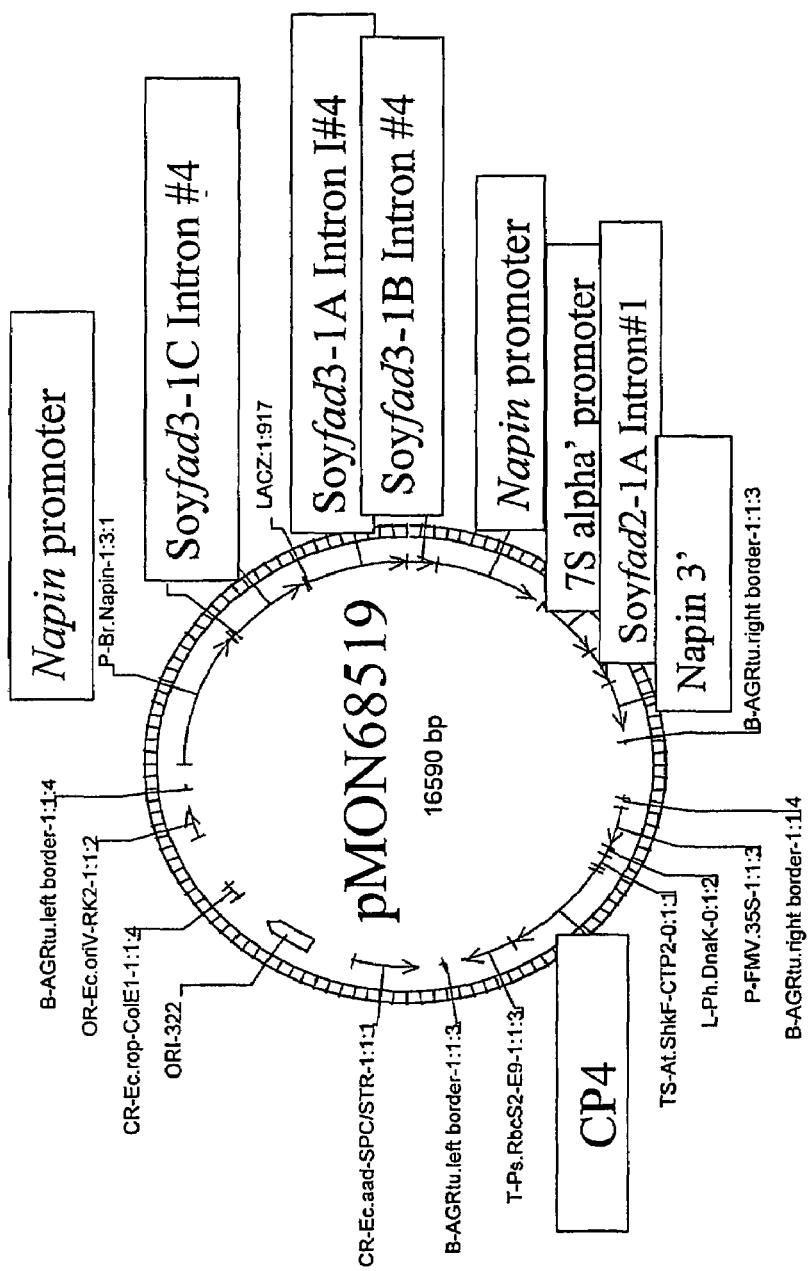
FIG. 11 is a schematic of construct pMON68519.

In constructing the plasmid pMON68519 (FIG. 11), pCGN5453 (containing 7Salpha' promoter fused to the FAD3-1A intron #4, with a pea RBCS 3') and KWHIT 032858 (pCR2.1 containing the FAD1B intron #4) are digested with EcoRI and ligated together to form KWHIT03004 (containing 7Salpha' promoter fused to the FAD3-1A intron #4 and FAD3-1B intron #4, with a pea RBCS 3'). KWHIT03004 is digested with XhoI and KAWHIT032980 (containing FAD3-1C intron #4 in PCR2.1) is digested with EcoRI. The ends of both digested plasmids are filled and the plasmids are subsequently ligated. The resulting plasmid is named KAWHIT030005 (containing 7Salpha' promoter fused to the FAD3-1A intron #4, FAD3-1B intron #4, and FAD3-1B intron #4, with a pea RBCS 3'). KAWHIT030005 is digested with SacI and then the DNA is treated with the Klenow fragment of T4 polymerase to create blunt ends. pCGN7770 (containing the Napin promoter and Napin 3') is digested with XhoI and blunt-ended with Kienow fragment of T4 polymerase. The blunt ends of plasmids KAWHIT030005 and pCGN7770 are ligated together to form KWHIT03007 (containing a Napin promoter fused to the FAD2-1A intron, the FAD3-1A intron #4, FAD3-1B intron #4, FAD3-1C intron #4, with a Napin 3').

KWHIT03007 is then digested with NotI and the ends are filled with the Klenow fragment of T4 polymerase, forming blunt ends. The Napin promoter fused to the FAD2-1 A intron, the FAD3-1A intron #4, FAD3-1B intron #4, FAD3-1C intron #4, with a Napin3' (KWHIT03007) is blunt end ligated into pMON68504 which is digested with EcoRV. pMON68504 contains the Soy FAD2-1A intron fused to the 7s Alpha' promoter within the 2 tDNA vector pMON41162, which contains the CP4 gene regulated by the FMV promoter, with the pea RBCS 3'. The blunt end ligation between KWHIT03007 and pMON6850 results in the plasmid, pMON68519. pMON68519 is transformed into the ABI strain of *Agrobacterium tumefaciens* and cocultivated into soybean.

Example 3

Plant Transformation and Analysis

Linear DNA fragments containing the expression constructs for sense and antisense suppression of the Δ12 and Δ15 desaturase genes are stably introduced into soybean (Asgrow variety A3244 or A4922A32) by the particle bombardment method of McCabe et al. (1988), *Bio/Technology*, 6:923-926 or via cocultivation with *Agrobacterium tumefaciens*, strain ABI. (Martinell, U.S. Pat. No. 6,384,310). Transformed soybean plants are identified by selection on media containing glyphosate.

Fatty acid compositions are analyzed from seed of soybean lines transformed with the intron expression constructs using gas chromatography. R1 pooled seed and R1 single seed oil compositions demonstrate that the mono- and polyunsaturated fatty acid compositions were altered in the oil of seeds from transgenic soybean lines as compared to that of the seed from non-transformed soybean. Tables I, II, and III provide summaries of results which were obtained using the described constructs. These data show that sense and antisense expression of non-coding regions of a desaturase gene result in the modification of the fatty acid compositions. The data also shows that introns can be used to obtain a variety of lines with varying fatty acid compositions. Selections can be made from such lines depending on the desired relative -fatty acid composition. Because each intron is able to modify the levels of each fatty acid to varying extents, it is contemplated that combinations of introns can be used depending on the desired compositions.

TABLE I

|  | Orientation | Event | Oleic | Linoleic | Linolenic |
|---|---|---|---|---|---|
| FAD2 |  |  |  |  |  |
| wildtype (control) |  | 5469-5 null R1 pool | 18.15% | 55.59% | 7.97% |
|  |  | 10 seed average | 13.89% | 55.89% | 9.067% |
|  |  | 5469-27 null R1 pool | 19.15% | 54.62% | 9.32% |
|  |  | A4922 | 15.75% | 56.1% | 8.75% |
|  |  | 5471-13 null R1 pool | 17.02% | 56.49% | 9.08% |
|  |  | 10 seed average | 13.86% | 56.14% | 9.49% |
|  |  | A4922 | 14.95% | 55.95% | 9.07% |
| full length cDNA (control) | sense | 5462-133 R1 pool | 84% | 2.17% | 1.55% |
|  | sense | best 5462-133 R1 seed | 84% | 0.59% | 1.76% |
| intron 1 | sense | 5469-6 R1 pool | 29.93% | 46.53% |  |
|  |  | 5469-8 R1 pool | 36.5% | 42.11% | 5.98% |
|  |  | best 5469-6 R1 seed | 44.41% | 29.34% | 6.68% |
|  |  | best 5469-8 R1 seed | 41.26% | 33.16% | 5.74% |
|  |  | 5469-14 R1 pool | 61.06% | 16.42% | 7.75% |
|  |  | 5469-20 R1 pool | 48.89% | 31.61% | 4.89% |
|  |  | 5469-22 R1 pool | 80% | 2.97% | 4.78% |
|  |  | best 5469-14 R1 seed | 62.21% | 11.97% | 8.81% |
|  |  | 5485-3 R1 pool | 63.54% | 14.09% | 7.32% |
|  |  | 5485-53 R1 pool | 47.58% | 27.64% | 7.81% |

TABLE I-continued

| | Orientation | Event | Oleic | Linoleic | Linolenic |
|---|---|---|---|---|---|
| | antisense | 5471-8 R1 pool | 31.05% | 43.62% | 7.07% |
| | | 5471-2 R1 pool | 27.98% | 48.88% | 6.83% |
| | | 5471-26 R1 pool | 32.66% | 44.54% | 6.76% |
| | | best 5471-8 R1 seed | 57.4% | 23.37% | 5.73% |
| | | best 5471-2 R1 seed | 28.08% | 46.14% | 6.52% |
| | | best 5471-26 R1 seed | 43.3% | 34.15% | 5.6% |
| | | 5486-33 R1 pool | 32.37% | 43.66% | 6.87% |
| | | 5486-12 R1 pool | 27.32% | 46.97% | 6.4% |
| | | 5486-40 R1 pool | 26.79% | 48.72% | 6.55% |
| FAD3 | | | | | |
| wildtype (control) | | 5473-7 null R1 pool | 15.65% | 56.74% | 9.55% |
| | | A4922 R1 pool | 19.84% | 56.79% | 7.48% |
| full length cDNA (control) | sense | 5464-50 R1 pool | 18.06% | 62.03% | 2.75% |
| | | best 5464-50 R1 seed | 17.08% | 62.44% | 1.72% |
| intron 1 | antisense | 5473-8 R1 pool | 33.47% | 45.97% | 5.54% |
| | | 5473-1 R1 pool | 33.34% | 42.67% | 7.59% |
| intron 2 | antisense | 5466-20 R1 pool | 28.43% | 48.83% | 6.37% |
| | | 5466-16 R1 pool | 27.61% | 49.92% | 5.96% |
| intron 4 | sense | 5455-19 R1 pool | 40.35% | 39.97% | 4.61% |
| | | 5455-10 R1 pool | 35.14% | 43.59% | 5.53% |
| | | 5455-57 R1 pool | 38.04% | 42.44% | 5.24% |
| | | 5455-76 R1 pool | 37.24% | 42.42% | 5.37% |
| | | 5455-107 R1 pool | 36.44% | 42.72% | 5.62% |
| | | best 5455-57 R1 seed | 45.36% | 35.55% | 4.92% |
| | | best 5455-76 R1 seed | 35.3% | 43.54% | 5.53% |
| | | best 5455-107 R1 seed | 45.56% | 34.85% | 5.12% |
| | antisense | 5459-2 R1 pool | 34.5% | 43.87% | 5.59% |
| | | 5459-6 R1 pool | 33.78% | 44.12% | 5.62% |
| | | 5459-20 R1 pool | 28.26% | 49.48% | 5.5% |
| | | best 5459-2 R1 seed | 61.45% | 23.45% | 3.38% |
| | | best 5459-6 R1 seed | 53.51% | 29.68% | 3.53% |
| | | best 5459-20 R1 seed | 30 | 50.55% | 4.15% |
| intron 5 | sense | 5456-38 R1 pool | 28.23% | 49.59% | 6.74% |
| | | 5456-62 R1 pool | 28.94% | 48.66% | 6.25% |
| | | best 5456-62 R1 seed | 29.5% | 43.69% | 5.4% |
| | antisense | 5460-9 R1 pool | 29.78% | 48.57% | 5.54% |
| | | 5460-21 R1 pool | 28.37% | 49.79% | 5.54% |
| | | best 5460-21 R1 seed | 35.18% | 40.52% | 5.33% |

TABLE II

Oil Composition data for seeds containing pMON68521
R1 single seed data

| Construct | Strain ID | 16:0 | 18:0 | 18:1 | 18:2 | 18:3 |
|---|---|---|---|---|---|---|
| PMON68521 | GM_A32162 | 12.0 | 3.4 | 42.8 | 35.5 | 5.3 |
| PMON68521 | GM_A32162 | 11.5 | 2.6 | 39.4 | 40.0 | 5.2 |
| PMON68521 | GM_A31619 | 10.4 | 2.8 | 39.1 | 40.4 | 5.8 |
| PMON68521 | GM_A32162 | 11.9 | 2.6 | 36.7 | 41.9 | 5.8 |
| PMON68521 | GM_A32162 | 12.2 | 2.5 | 34.9 | 43.0 | 6.3 |
| PMON68521 | GM_A32162 | 13.0 | 2.8 | 30.4 | 46.6 | 6.0 |
| PMON68521 | GM_A31610 | 12.4 | 1.9 | 28.3 | 49.8 | 7.1 |
| PMON68521 | GM_A32162 | 11.9 | 2.9 | 26.5 | 51.6 | 6.1 |
| PMON68521 | GM_A31792 | 13.2 | 3.3 | 25.3 | 50.2 | 7.2 |
| PMON68521 | GM_A31395 | 12.5 | 3.7 | 25.1 | 50.2 | 6.7 |
| PMON68521 | GM_A31393 | 13.1 | 3.5 | 24.1 | 51.9 | 5.6 |
| PMON68521 | GM_A31615 | 14.0 | 2.2 | 24.0 | 52.5 | 6.7 |
| PMON68521 | GM_A32209 | 12.5 | 3.5 | 23.7 | 51.5 | 7.6 |
| PMON68521 | GM_A31612 | 11.8 | 3.0 | 23.7 | 51.1 | 9.5 |
| PMON68521 | GM_A32209 | 12.6 | 3.3 | 23.6 | 52.2 | 7.2 |
| PMON68521 | GM_A32209 | 12.4 | 3.2 | 23.0 | 53.1 | 7.2 |
| PMON68521 | GM_A31489 | 12.3 | 3.2 | 22.5 | 54.0 | 6.9 |
| PMON68521 | GM_A32252 | 12.7 | 4.4 | 22.3 | 52.4 | 7.1 |
| PMON68521 | GM_A32162 | 12.6 | 3.1 | 22.2 | 54.9 | 6.2 |
| PMON68521 | GM_A32089 | 13.5 | 3.2 | 22.2 | 52.4 | 7.9 |
| PMON68521 | GM_A31393 | 12.6 | 4.3 | 22.2 | 53.0 | 5.7 |
| PMON68521 | GM_A31610 | 12.5 | 2.7 | 21.8 | 55.5 | 6.9 |
| PMON68521 | GM_A31610 | 12.6 | 2.4 | 21.7 | 55.8 | 6.9 |
| PMON68521 | GM_A31656 | 12.7 | 3.6 | 21.6 | 53.2 | 8.0 |
| PMON68521 | GM_A31612 | 12.3 | 3.6 | 21.6 | 54.0 | 7.2 |
| PMON68521 | GM_A31610 | 13.2 | 2.6 | 21.0 | 56.2 | 6.5 |
| PMON68521 | GM_A31604 | 13.5 | 3.1 | 20.4 | 55.3 | 7.0 |
| PMON68521 | GM_A31610 | 13.2 | 2.6 | 20.4 | 56.7 | 6.4 |
| PMON68521 | GM_A31489 | 12.8 | 3.1 | 20.1 | 55.5 | 7.1 |
| PMON68521 | GM_A31525 | 12.2 | 3.0 | 20.1 | 57.2 | 6.3 |
| A3244 | | 13.9 | 4.1 | 15.8 | 56.3 | 9.0 |
| A3244 | | 13.7 | 4.1 | 14.2 | 57.6 | 9.3 |
| A3244 | | 13.6 | 4.3 | 14.1 | 57.4 | 9.7 |
| A3244 | | 13.9 | 4.1 | 14.1 | 56.9 | 10.0 |
| A3244 | | 13.8 | 4.4 | 13.6 | 57.6 | 9.8 |
| A3244 | | 14.2 | 4.8 | 13.6 | 56.8 | 9.5 |
| A3244 | | 14.2 | 4.3 | 13.2 | 56.5 | 10.8 |
| A3244 | | 14.0 | 4.2 | 13.1 | 57.0 | 10.6 |
| A3244 | | 14.0 | 4.5 | 12.9 | 57.3 | 10.3 |

TABLE III

Oil Composition data for seeds containing pMON68519
R1 single seed data

| Construct | Strain ID | 16:0 | 18:0 | 18:1 | 18:2 | 18:3 |
|---|---|---|---|---|---|---|
| PMON68519 | GM_A29911 | 13.0 | 4.8 | 40.7 | 34.4 | 5.2 |
| PMON68519 | GM_A29911 | 12.3 | 3.8 | 38.8 | 37.5 | 5.8 |
| PMON68519 | GM_A29911 | 12.3 | 3.3 | 34.0 | 42.6 | 6.5 |

TABLE III-continued

Oil Composition data for seeds containing pMON68519 R1 single seed data

| Construct | Strain ID | 16:0 | 18:0 | 18:1 | 18:2 | 18:3 |
|---|---|---|---|---|---|---|
| PMON68519 | GM_A32856 | 12.9 | 3.5 | 33.6 | 42.2 | 6.5 |
| PMON68519 | GM_A32856 | 12.6 | 3.1 | 33.3 | 43.4 | 6.4 |
| PMON68519 | GM_A32856 | 13.0 | 3.1 | 31.3 | 45.4 | 6.1 |
| PMON68519 | GM_A32856 | 12.7 | 3.2 | 28.9 | 47.3 | 6.6 |
| PMON68519 | GM_A29911 | 12.9 | 4.0 | 28.7 | 46.5 | 6.7 |
| PMON68519 | GM_A29911 | 12.2 | 3.1 | 28.1 | 47.4 | 6.8 |
| PMON68519 | GM_A32856 | 13.3 | 3.2 | 26.5 | 48.7 | 7.1 |
| PMON68519 | GM_A32856 | 13.2 | 3.2 | 26.5 | 49.3 | 6.8 |
| PMON68519 | GM_A29911 | 13.1 | 3.2 | 26.1 | 49.4 | 7.1 |
| PMON68519 | GM_A32856 | 13.2 | 3.6 | 25.9 | 48.9 | 7.1 |
| PMON68519 | GM_A32857 | 13.3 | 3.1 | 23.3 | 52.2 | 7.4 |
| PMON68519 | GM_A29911 | 12.8 | 3.5 | 23.3 | 52.5 | 6.6 |
| PMON68519 | GM_A29911 | 12.6 | 3.1 | 21.4 | 51.9 | 9.0 |
| PMON68519 | GM_A29911 | 13.4 | 3.6 | 20.1 | 53.6 | 7.9 |
| A3244 | | 13.2 | 4.3 | 16.5 | 55.7 | 9.7 |
| A3244 | | 13.5 | 3.2 | 16.3 | 56.8 | 9.2 |
| A3244 | | 13.7 | 3.4 | 15.4 | 57.7 | 9.2 |
| A3244 | | 13.9 | 3.3 | 15.1 | 57.9 | 9.1 |
| A3244 | | 13.8 | 3.6 | 14.3 | 58.3 | 9.2 |
| A3244 | | 13.5 | 3.4 | 13.6 | 58.2 | 10.4 |
| A3244 | | 13.5 | 3.9 | 12.5 | 58.4 | 11.2 |
| A3244 | | 14.6 | 3.8 | 12.1 | 58.2 | 10.8 |
| A3244 | | 14.5 | 3.9 | 11.8 | 57.8 | 11.4 |

Example 4

Linear DNA fragments containing dsRNAi constructs for suppression of the Δ12 and Δ15 desaturase genes are stably introduced into soybean (Asgrow variety A3244 or A4922A32) via cocultivation with *Agrobacterium tumefaciens*, strain ABI. (Martinell, U.S. Pat. No. 6,384,301) or by the particle bombardment method of McCabe et al. (1988), *Bio/Technology*, 6:923-926. Introduced constructs include: (1) 7S promoter-FAD2-1A sense intron-FAD3-1A sense intron-FAD3-1B sense intron-spliceable FAD3 intron #5-FAD3-1B antisense intron-FAD3-1A antisense intron-FAD2-1A antisense intron-pea rbcS; (2) 7S promoter-FAD3-1A sense intron-FAD3-1B sense intron-spliceable FAD3 intron #5-FAD3-1B antisense intron-FAD3-1A antisense intron-pea rbcS; (3) 7S promoter-FAD2-1A sense intron-FAD3-1A sense intron-spliceable FAD3 intron #5-FAD3-1A antisense intron-FAD2-1A antisense intron-pea rbcS. Representative sequences for FAD2-1A, FAD2-1B, FAD2-2B, FAD3-1A, FAD3-1B, and FAD3-1C introns may be found, without limitation, in U.S. application Ser. No. 10/176,149, filed Jun. 21, 2002, and U.S. application Ser. No. 09/638,508, filed Aug. 11, 2000, and U.S. Provisional Application Ser. No. 60/151,224, filed Aug. 26, 1999, and U.S. Provisional Application Ser. No. 60/172,128, filed Dec. 17, 1999. Transformed soybean plants are identified by selection on media containing glyphosate.

Fatty acid compositions are analyzed from transformed soybean seeds containing iron RNAi suppression constructs. Particular lines are selected depending on the desired relative fatty acid composition.

Example 5

5A.

RNA is isolated from homozygous R2 seed from two FAD2-1 intron suppressed lines (5469-14 and 5469-22), from two FAD2-1 cDNA suppressed lines (positive controls) (5462-87 and 5462-133), and from negative controls (wild type seed and seed from null segregants from each intron suppressed event). Northern gels containing these RNA samples are probed with the FAD2-1 cDNA. FAD2-1A transcript levels are significantly reduced in both the intron suppressed lines and the cDNA suppressed lines relative to the negative controls. The same Northern blot is probed with the constitutive FAD2-2 cDNA and no significant differences in the FAD2-2 transcript levels are observed between the FAD2-1 intron suppressed lines and the controls. In contrast, the FAD2-2 transcript in the cDNA suppressed lines, is significantly reduced. This Northern data indicates that the FAD2-1A intron is specifically inhibiting the accumulation of the FAD2-1 transcript but not the FAD2-2 transcript. A partial FAD2-2 genomic clone (SEQ ID NO: 3) is PCR amplified and sequence analysis reveals a 4.7 KB intron in the 5' untranslated region of the gene. The sequence of the FAD2-2 intron (SEQ ID NO: 4) shares no homology with the FAD2-1 intron.

5B.

RNA is isolated from homozygous R2 seed from four FAD3-1A intron #4 suppressed lines, from three FAD3-1B intron #4 suppressed lines, from negative control seed (non transformed wild type seed) and from seed from null segregants from each intron suppressed event). Northern gels containing these RNA samples are probed with the FAD3-1A 3'UTR region. Endogenous FAD3-1A transcript levels are significantly reduced in the FAD3-1A intron #4 suppressed lines relative to the wildtype or null controls. The same Northern blot is probed with the FAD3-1B 3' UTR region and no significant differences in the endogenous FAD3-1B transcript levels are observed relative to the FAD3-1A intron #4 suppressed lines, the wildtype or null controls. The sequence of the FAD3-1A intron #4 (SEQ ID NO: 8) shares no homology with the FAD3-1B intron #4 (SEQ ID NO: 13)

Example 6

Southern blot data indicate that there are at least two FAD3 gene family members. To determine the sequence of the other FAD3 gene family member and to determine if other members exist, a FAD3-1A gene sequence is used for a query Blast search against the Monsanto soybean DNA sequences database. Candidate ESTs from different FAD3 gene family members are used to design primers. Using this strategy, 2 primer sets are designed based on putative FAD3 sequences. Intron #4 regions from two other FAD3 gene family members are isolated. Primers are designed from the 211565_1.r1040 EST (designated FAD3-1B), (5' primer #15024: 5'-CATGCTTTCTGTGCTTCTC-3' (SEQ ID NO:26) and 3' primer #15027: 5'-GTTGATCCAACCATAGTCG-3' (SEQ ID NO:27)) in the region corresponding to the position of intron #4 of the FAD3-1A gene. These primers are used to PCR amplify the FAD3-1B intron #4 (SEQ ID NO:13), which when sequenced shared no sequence homology with the FAD3-1A intron #4 (SEQ ID NO: 8). The FAD3-1B gene also contains an intron #3C (SEQ ID NO: 12), which also did not share any homology with the FAD3-1A intron #3C (SEQ ID NO:11).

Another additional intron #4 is PCR amplified from a second EST, gsv701051989.H1 (designated FAD3-1C) using the following set of primers: 5' primer #16241: 5'-CACCATGGTCATCATCAGAAAC (SEQ ID NO:38) and the 3' primer #16242: TCACGATCCACAGTTGTGAGAC (SEQ ID NO:39). The FAD3-1C intron #4 (SEQ ID NO:14) shares 50% homology with the FAD3-1A intron #4 (SEQ ID NO: 8) and shares no homology with the FAD3-1B intron #4 (SEQ ID NO: 13). The FAD3-1C EST, like the FAD3-1B EST, also contains an intron #4 splice site in the same region of the gene.

Example 7

FAD2-1A/FAD3-1A Transformed Plants

7A.

A soybean FAD2-1A intron suppressed line is used to pollinate a soybean FAD3-1A intron suppressed line that is generated according to the methodology set forth in Example 3. RNA from soybean seeds containing both an expressed FAD2-1A intron region and FAD3-1A intron region is screened using Northern blotting (as described in Example 5) to determine the levels of FAD2-1, FAD2-2, FAD3-1A and FAD3-1B transcripts. Soybean plants with undetectable or low levels of FAD2-1 and FAD3-1A transcripts are screened for fatty acid composition as set forth in Example 3.

7B.

A soybean FAD2-1A intron suppressed line is also used to pollinate a low linolenic soybean FAD3 mutant line derived from a mutation. RNA from soybean seeds containing both one ore more expressed FAD2 intron regions and FAD3 mutations, including knock out, are screened using Northern blots (as described in Example 5) to determine the levels of FAD2-1, FAD2-2, FAD3-1A, FAD3-1C and FAD3-1B transcripts. Soybean plants with undetectable or low levels of FAD2 and FAD3 transcripts are screened for fatty acid composition as set forth in Example 3.

7C.

A soybean line with FAD3-1A, FAD3-1B, and FAD3-1C intron suppression is used to pollinate soybean plants with elevated levels of oleic acid containing a FAD2 mutant line derived from a spontaneous mutation. Soybean lines with FAD3-1A and FAD3-1B intron suppression, lines with FAD3-1A and FAD3-1C intron suppression, lines with FAD3-1B and FAD3-1C intron suppression, lines with FAD3-1A intron suppression, lines with FAD3-1B intron suppression and lines with FAD3-1C intron suppression are each used individually to pollinate soybean plants with elevated levels of oleic acid containing a FAD2 mutant line derived from a spontaneous mutation. RNA from soybean seeds containing both one or more expressed FAD3 intron regions and FAD2 mutations, including knock out, are screened using Northern blots as described in Example 5 to determine the levels of FAD2-1, FAD2-2, FAD3-1A, FAD3-1B and FAD3-1C transcripts. Soybean plants with undetectable or low levels of FAD2 or FAD3 transcripts are screened for fatty acid composition as set forth in Example 3.

Example 8

Single FAD2/FAD3 Constructs

Linear DNA fragments containing sense and antisense FAD2 and FAD3 introns, as well as FAD2 and FAD3 introns capable of producing a dsRNA, are constructed as set forth in Table IV.

TABLE IV

| Construct No. | Promoter 1 | Structural Nucleic Acid 1 (sense, antisense, dsRNA) | Promoter 2 | Structural Nucleic Acid 2 (sense, antisense, dsRNA) |
| --- | --- | --- | --- | --- |
| 1 | CaMV | FAD2-1A intron 1 | CaMV | FAD3-1A intron 1 |
| 2 | CaMV | FAD2-1B intron 1 | CaMV | FAD3-1A intron 1 |
| 3 | CaMV | FAD2-1A intron 1 | CaMV | FAD3-1A intron 4 |
| 4 | CaMV | FAD2-1B intron 1 | CaMV | FAD3-1A intron 4 |
| 5 | CaMV | FAD2-1A intron 1 | CaMV | FAD3-1B intron 4 |
| 6 | CaMV | FAD2-1B intron 1 | CaMV | FAD3-1B intron 4 |
| 7 | CaMV | FAD2-1A intron 1 | CaMV | FAD3-1C intron 4 |
| 8 | CaMV | FAD2-1B intron 1 | CaMV | FAD3-1C intron 4 |
| 9 | CaMV | FAD2-1A intron 1 | CaMV | FAD2-2B intron 1 |
| 10 | CaMV | FAD2-1B intron 1 | CaMV | FAD2-2B intron 1 |
| 11 | napin | FAD2-1A intron 1 | napin | FAD3-1A intron 1 |
| 12 | napin | FAD2-1B intron 1 | napin | FAD3-1A intron 1 |
| 13 | napin | FAD2-1A intron 1 | napin | FAD3-1A intron 4 |
| 14 | napin | FAD2-1B intron 1 | napin | FAD3-1A intron 4 |
| 15 | napin | FAD2-1A intron 1 | napin | FAD3-1B intron 4 |
| 16 | napin | FAD2-1B intron 1 | napin | FAD3-1B intron 4 |
| 17 | napin | FAD2-1A intron 1 | napin | FAD3-1C intron 4 |
| 18 | napin | FAD2-1B intron 1 | napin | FAD3-1C intron 4 |
| 19 | napin | FAD2-1A intron 1 | napin | FAD2-2B intron 1 |
| 20 | napin | FAD2-1B intron 1 | napin | FAD2-2B intron 1 |
| 21 | 7S | FAD2-1A intron 1 | CaMV | FAD3-1A intron 1 |
| 22 | 7S | FAD2-1B intron 1 | CaMV | FAD3-1A intron 1 |
| 23 | 7S | FAD2-1A intron 1 | CaMV | FAD3-1A intron 4 |
| 24 | 7S | FAD2-1B intron 1 | CaMV | FAD3-1A intron 4 |
| 25 | 7S | FAD2-1A intron 1 | CaMV | FAD3-1B intron 4 |
| 26 | 7S | FAD2-1B intron 1 | CaMV | FAD3-1B intron 4 |
| 27 | 7S | FAD2-1A intron 1 | CaMV | FAD3-1C intron 4 |
| 28 | 7S | FAD2-1B intron 1 | CaMV | FAD3-1C intron 4 |
| 29 | 7S | FAD2-1A intron 1 | CaMV | FAD2-2B intron 1 |
| 30 | 7S | FAD2-1B intron 1 | CaMV | FAD2-2B intron 1 |
| 31 | CaMV | FAD2-1A intron 1 | 7S | FAD3-1A intron 1 |
| 32 | CaMV | FAD2-1B intron 1 | 7S | FAD3-1A intron 1 |
| 33 | CaMV | FAD2-1A intron 1 | 7S | FAD3-1A intron 4 |
| 34 | CaMV | FAD2-1B intron 1 | 7S | FAD3-1A intron 4 |
| 35 | CaMV | FAD2-1A intron 1 | 7S | FAD3-1B intron 4 |
| 36 | CaMV | FAD2-1B intron 1 | 7S | FAD3-1B intron 4 |
| 37 | CaMV | FAD2-1A intron 1 | 7S | FAD3-1C intron 4 |

TABLE IV-continued

| Construct No. | Promoter 1 | Structural Nucleic Acid 1 (sense, antisense, dsRNA) | Promoter 2 | Structural Nucleic Acid 2 (sense, antisense, dsRNA) |
|---|---|---|---|---|
| 38 | CaMV | FAD2-1B intron 1 | 7S | FAD3-1C intron 4 |
| 39 | CaMV | FAD2-1A intron 1 | 7S | FAD2-2B intron 1 |
| 40 | CaMV | FAD2-1B intron 1 | 7S | FAD2-2B intron 1 |

As shown, each construct listed in the table can have several configurations depending on the nature and orientation of the structural nucleic acids in the construct. For example, construct 30 may be configured as follows: (1) 7S promoter-FAD2-1B intron 1 (sense)-CaMV -promoter-FAD2-2B intron 1 (sense); (2) 7S promoter-FAD2-1B intron 1 (sense)-CaMV promoter-FAD2-2B intron 1 (antisense); (3) 7S promoter-FAD2-1B intron 1 (sense)-CaMV promoter-FAD2-2B intron 1 (dsRNA); (4) 7S promoter-FAD2-1B intron 1 (antisense)-CaMV promoter-FAD2-2B intron 1 (sense); (5) 7S promoter-FAD2-1B intron 1 (antisense)-CaMV promoter-FAD2-2B intron 1 (antisense); (6) 7S promoter-FAD2-1B intron 1 (antisense)-CaMV promoter-FAD2-2B intron 1 (dsRNA); (7) 7S promoter-FAD2-1B intron 1 (dsRNA)-CaMV promoter-FAD2-2B intron 1 (sense); (8) 7S promoter-FAD2-1B intron 1 (dsRNA)-CaMV promoter-FAD2-2B intron 1 (antisense); or (9) 7S promoter-FAD2-1B intron 1 (dsRNA)-CaMV promoter-FAD2-2B intron 1 (dsRNA).

These constructs can be stably introduced into soybean (for example, Asgrow variety A4922 or Asgrow variety A3244) by the methods described earlier, including the particle bombardment method of McCabe et al. (1988), *Bio/Technology,* 6:923-926 or *Agrobacterium*-mediated transformation (Martinell, U.S. Pat. No. 6,384,301). Transformed soybean plants are identified by selection on media containing glyphosate. Fatty acid compositions are analyzed from seed of soybean lines transformed with the constructs using gas chromatography.

Example 9

Linear DNA fragments containing expression constructs for sense and antisense expression of the FAD2-1 and FAD2-2 introns are stably introduced into soybean (for example, Asgrow variety A4922 or Asgrow variety A3244) by the methods described earlier, including the particle bombardment method of McCabe et al. (1988), *Bio/Technology,* 6:923-926 or *Agrobacterium*-mediated transformation (Martinell, U.S. Pat. No. 6,384,301). The following constructs are introduced: (1) FAD2-1A intron (sense)-FAD2-2 intron (antisense); (2) FAD2-1A intron (sense)-FAD2-2 intron (sense); (3) FAD2-1A intron (antisense)-FAD2-2 intron (antisense); (4) FAD2-1A intron (antisense)-FAD2-2 intron (sense); (5) FAD2-1B intron (sense)-FAD2-2 intron (antisense); (6) FAD2-1B intron (sense)-FAD2-2 intron (sense); (7) FAD2-1B intron (antisense)-FAD2-2 intron (antisense); and (8) FAD2-1B intron (antisense)-FAD2-2 intron (sense). Transformed soybean plants are identified by selection on media containing glyphosate. Fatty acid compositions are analyzed from seed of soybean lines transformed with the constructs using gas chromatography. Seed of the transformed plants exhibit high levels of oleic acid (over 80%).

Additional linear DNA fragments containing expression constructs for sense and antisense expression of the FAD2-1, FAD2-2, and FAD3 introns are stably introduced into soybean (Asgrow variety A4922) by the method of McCabe et al. (1988), *Bio/Technology,* 6:923-926. Exemplary constructs include: (1) FAD2-1A intron (sense or antisense)-FAD2-2 intron (sense or antisense)-FAD3-1A intron 1 (sense or antisense); (2) FAD2-1A intron (sense or antisense)-FAD2-2 intron (sense or antisense)-FAD3-1A intron 4 (sense or antisense); (3) FAD2-1A intron (sense or antisense)-FAD2-2 intron (sense or antisense)-FAD3-1B intron 4 (sense or antisense); and (4) FAD2-1A intron (sense or antisense)-FAD2-2 intron (sense or antisense)-FAD3-1C intron 4 (sense or antisense). Transformed soybean plants are identified by selection on media containing glyphosate. Fatty acid compositions are analyzed from seed of soybean lines transformed with the constructs using gas chromatography. Seed of the transformed plants exhibit high levels of oleic acid (over 80%).

What is claimed is:

1. A transgenic soybean plant having a nucleic acid molecule comprising a heterologous promoter operably linked to a polynucleotide that is at least 95% identical to about 275 to about 350 contiguous nucleotides of SEQ ID NO: 1, or complete complements thereof, wherein said soybean plant produces seed with more oleic acid than a soybean plant having a similar genetic background but lacking said nucleic acid molecule.

2. The transgenic soybean plant according to claim 1, wherein a seed of said transformed soybean plant exhibits a modified fatty acid composition that is about 60-80% oleic acid.

3. The transgenic soybean plant according to claim 2, wherein said promoter is a seed specific promoter.

4. The transgenic soybean plant according to claim 1, wherein said polynucleotide is at least 98% identical to about 275 to about 350 contiguous nucleotides of SEQ ID NO:1, or complete complements thereof.

5. The transgenic soybean plant according to claim 1, wherein said promoter is a 7S promoter.

6. The transgenic soybean plant according to claim 1, wherein said polynucleotide is at least 99% identical to about 275 to about 350 contiguous nucleotides of SEQ ID NO:1, or complete complements thereof.

7. The transgenic soybean plant according to claim 1, wherein said polynucleotide is 100% identical to about 275 to about 350 contiguous nucleotides of SEQ ID NO:1, or a complete complement thereof.

8. The transgenic soybean plant according to claim 1, wherein said nucleic acid molecule is transcribed and is capable of selectively reducing the level of a transcript encoded by a FAD2-1 gene while leaving the level of a transcript encoded by a FAD2-2 gene partially unaffected.

9. The transgenic soybean plant according to claim 1, wherein said nucleic acid molecule is transcribed and is capable of selectively reducing the level of a transcript encoded by a FAD2-1 gene while leaving the level of a transcript encoded by a FAD2-2 gene substantially unaffected.

10. The transgenic soybean plant according to claim 1, wherein a seed of said transformed soybean plant exhibits a modified fatty acid composition that is about 65-75% oleic acid.

11. A transgenic soybean plant having a nucleic acid molecule comprising a heterologous promoter operably linked to a nucleic acid sequence that is at least 95% identical to about 275 to about 350 contiguous nucleotides of SEQ ID NO: 1, or complete complements thereof wherein a seed of said transformed soybean plant exhibits a modified fatty acid composition that is about 50-90% oleic acid.

12. The transgenic soybean plant according to claim 11, wherein said nucleic acid sequence is transcribed and is capable of selectively reducing the level of a transcript encoded by a FAD2-1 gene while leaving the level of a transcript encoded by a FAD2-2 gene partially unaffected, substantially unaffected or essentially unaffected.

13. A method of producing a soybean plant having a seed with increased oleic acid content comprising: transforming a soybean plant with a nucleic acid molecule comprising a heterologous promotor operably linked to a polynucleotide that is 95% identical to about 275 to about 350 contiguous nucleotides of SEQ ID NO: 1, or complete complements thereof; and growing said soybean plant, wherein said soybean plant produces seed with increased oleic acid content compared to a soybean plant having a similar genetic background but lacking said nucleic acid molecule.

14. The transgenic soybean plant according to claim 11, wherein said nucleic acid sequence is at least 98% identical to about 275 to about 350 contiguous nucleotides of SEQ ID NO:1, or complete complements thereof.

15. The transgenic soybean plant according to claim 11, wherein said nucleic acid sequence is at least 99% identical to about 275 to about 350 contiguous nucleotides of SEQ ID NO:1, or complete complements thereof.

16. The transgenic soybean plant according to claim 11, wherein said nucleic acid sequence is 100% identical to about 275 to about 350 contiguous nucleotides of SEQ ID NO:1.

17. The transgenic soybean plant according to claim 1, herein a seed of said transformed soybean plant exhibits a modified fatty acid composition that is about 50% or greater of oleic acid.

* * * * *